(12) United States Patent
Whittaker et al.

(10) Patent No.: US 12,145,981 B2
(45) Date of Patent: *Nov. 19, 2024

(54) METHODS AND COMPOUNDS FOR THE TREATMENT OR PREVENTION OF SEVERE INFLUENZA

(71) Applicant: Orph Pharma IP Company Limited, London (GB)

(72) Inventors: Paul Andrew Whittaker, Hertfordshire (GB); Neil Edward Torbett, Hertfordshire (GB)

(73) Assignee: POOLBEG PHARMA (UK) LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,539

(22) Filed: May 6, 2022

(65) Prior Publication Data

US 2022/0275062 A1 Sep. 1, 2022

Related U.S. Application Data

(63) Continuation of application No. 16/312,784, filed as application No. PCT/GB2017/051865 on Jun. 26, 2017, now Pat. No. 11,339,207.

(30) Foreign Application Priority Data

Jul. 2, 2016 (GB) ...................... 1611712

(51) Int. Cl.
| | |
|---|---|
| *C07K 16/10* | (2006.01) |
| *A61K 38/00* | (2006.01) |
| *A61K 38/19* | (2006.01) |
| *A61K 38/20* | (2006.01) |
| *C12N 9/12* | (2006.01) |

(52) U.S. Cl.
CPC ........ *C07K 16/1018* (2013.01); *A61K 38/005* (2013.01); *A61K 38/191* (2013.01); *A61K 38/204* (2013.01); *A61K 38/2066* (2013.01); *C12N 9/12* (2013.01); *C12Y 207/11024* (2013.01)

(58) Field of Classification Search
None
See application file for complete search history.

(56) References Cited

U.S. PATENT DOCUMENTS

| | | | |
|---|---|---|---|
| 8,536,194 | B2 | 9/2013 | Almansa Rosales |
| 8,697,627 | B2 | 4/2014 | Alam |
| 2010/0151042 | A1 | 6/2010 | Liang et al. |
| 2011/0003848 | A1 | 1/2011 | Butcher |

FOREIGN PATENT DOCUMENTS

| | | |
|---|---|---|
| JP | 2003-516314 | 5/2003 |
| JP | 2006-519205 | 8/2006 |
| JP | 2017-515910 | 6/2017 |
| WO | WO 01/19322 A2 | 3/2001 |
| WO | WO 01/38313 A1 | 5/2001 |
| WO | WO 02/059083 A2 | 8/2002 |
| WO | WO 2004/076450 A1 | 9/2004 |
| WO | WO 2010/029167 A2 | 3/2010 |
| WO | WO 2010/038085 A2 | 4/2010 |
| WO | WO 2015/173788 A1 | 11/2015 |
| WO | WO 2016/154329 A2 | 9/2016 |
| WO | WO 2017/151409 A1 | 9/2017 |
| WO | WO 2018/007788 A1 | 1/2018 |

OTHER PUBLICATIONS

Y. Borgeling et al., "Inhibition of p38 Mitogen-activated Protein Kinase Impairs Influenza Virus-induced Primary and Secondary Host Gene Responses and Protects Mice from Lethal H5N1 Infection", Journal of Biological Chemistry, vol. 289, No. 1, Nov. 4, 2013 (Nov. 4, 2013), pp. 13-27, XP55161048, ISSN: 0021-9258, DOI: 10.1074/jbc.M113.469239 p. 23; figure 7. Acta Virologica, vol. 58, 2014, pp. 374-379.

Wei et al., "Roles of p38 MAPK in the regulation of the inflammatory response to swine influenza virus-induced acute lung injury in mice". Journal of Virology, vol. 84, No. 21, 2010, pp. 11359-11373.

Marchant et al. "Toll-like receptor 4-mediated activation of p38 mitogen-activated protein kinase is a determinant of respiratory virus entry and tropism". Biochemical and Biophysical Research Communications, vol. 477, No. 3, 2016, pp. 311-316.

Choi et al., "A novel p38 mitogen activated protein kinase (MAPK) specific inhibitor suppresses respiratory syncytial virus and influenza. A virus replication by inhibiting virus-induced p38 MAPK activation".

International Search Report and Written Opinion mailed Aug. 30, 2017 in corresponding International Application No. PCT/GB2017/051865.

Search Report issued in corresponding Application No. GB 1611712.9 Neuroscience Letters, 2015, vol. 604, pp. 69-74.

English Translation of the Office Action mailed on Jun. 1, 2021 in corresponding Japanese Patent Application No. JP2018-569081.

Jian-Ping Dai et al., Identification of 23-(S)-2 Amino-3-Phenylpropanoyl-Silybin as an Antiviral Agent for Influenza a Virus Infection In Vitro and In Vivo, Antimicrobial Agents and Chemotherapy, Sep. 2013, vol. 57, No. 9, p. 4433-4443.

Cuenda et al. (Mar. 24, 2007) "p38 MAP-Kinases pathway regulation, function and role in human diseases", Biochimica et Biophysica Acta.

Lee et al. (Aug. 2005) "p38 Mitogen-Activated Protein Kinase-Dependent Hyperinduction of Tumor Necrosis Factor Alpha Expression in Response to Avian Influenza Virus H5N1", Journal of Virology.

(Continued)

*Primary Examiner* — Benjamin P Blumel
(74) *Attorney, Agent, or Firm* — Jon E. Gordon; Haug Partners LLP

(57) ABSTRACT

A p38 MAPK inhibitor for use in the treatment or prevention of severe influenza in a human patient. In some embodiments, the severe influenza may be characterised by hypercytokinemia involving elevated levels of one or more pro-inflammatory cytokines. The p38 MAP kinase inhibitor may act to inhibit the release of such pro-inflammatory mediators from endothelial cells. In some embodiments, the p38 MAP kinase inhibitor may inhibit the release of IP 10 from endothelial cells, preferably in a dose-dependent manner.

19 Claims, 16 Drawing Sheets

(56) References Cited

OTHER PUBLICATIONS

Figure 1:
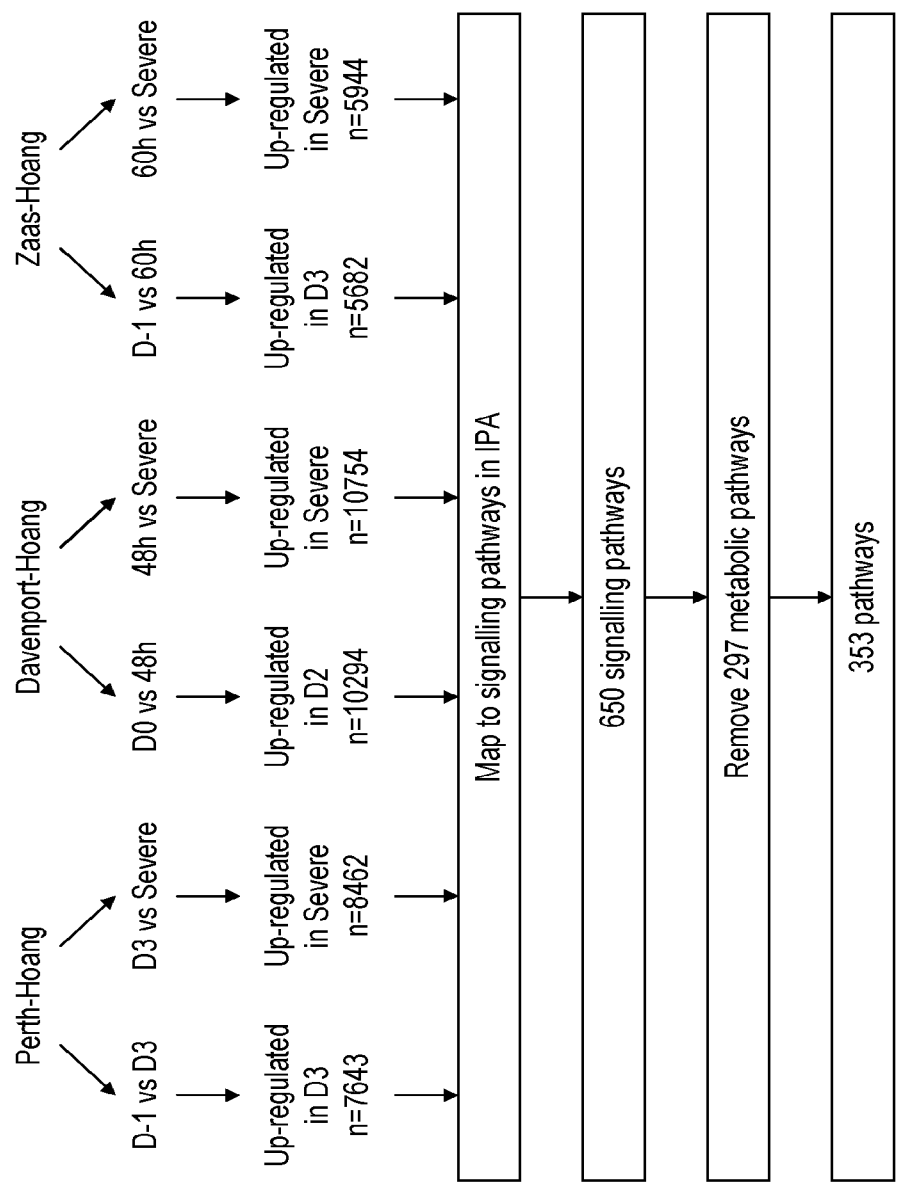

Geiler et al. (Sep. 24, 2010) "Comparison of pro-inflammatory cytokine expression and cellular signal transduction in human macrophages infected with different influenza A viruses", Med Microbiol Immunol.
Hui et al. (Jan. 15, 2009) "Induction of Proinflammatory Cytokines in Primary Human Macrophages by Influenza A Virus (H5N1) is Selectively Regulated by IFN Regulatory Factor 3 and p38 Mark", The Journal of Immunology.
Geiler et al. (Sep. 2, 2009) "N-acetyl-L-cysteine (NAC) inhibits virus replication and expression of pro-inflammatory molecules in A549 cells infected with highly pathogenic H5N1 influenza A virus", Biochemical Pharmacology.
Wu et al. (Jan. 20, 2010) "Innate immune response to H3N2 and H1N1 influenza virus infection in a human lung organ culture model", Virology.
Liu et al. (May 26, 2015) "Mouse lung slices: An ex vivo model for the evaluation of antiviral and anti-inflammatory agents against influenza viruses", Antiviral Research.
Paquette et al. (Jun. 5, 2012) "Interleukin-6 is a Potential Biomarker for Severe Pandemic H1N1 Influenza A Infection", PLoS One.
Ramos et al. (Jul. 20, 2015) "Modulating the innate immune response to influenza A virus: potential therapeutic use of anti-inflammatory drugs", Frontiers in Immunology.
CDC website for Influenza—What you should know about Flu Antiviral Drugs, accessed on Jun. 8, 2020.
Rui Liu et al: "Mouse Lung Slices: An ex vivo model for the evaluation of antiviral and anti-inflammatory agents against influenza viruses", Antiviral Research, vol. 120, Aug. 1, 2015, (Aug. 1, 2015), pp. 101-111, XP055355559. Critical Care Medicine, vol. 43, No. 9, 2015, pp. 1859-1869.
Christie et al. "A randomized dose-escalation study of the safety and anti-inflammatory activity of the p38 mitogen-activated protein kinase inhibitor dilmapimod in severe trauma subjects at risk for acute respiratory distress syndrome". International Journal of Molecular Sciences, vol. 14, 2013, pp. 7327-7340 [available via https://www.ncbi.nlm.nih.gov/pmc/articles/PMC3645688/].
Law et al. "A role for protein phosphatase 2A in regulating p38 mitogen activated protein kinase activation and tumor necrosis factor-alpha expression during influenza virus infection". The Journal of Immunology, vol. 164, 2000, pp. 3222-3228 [available via http://www.jimmunol.org/content/164/6/3222.long].
Kujime et al. "p38 mitogen-activated protein kinase and c-Jun-$NH_2$-terminal kinase regulates Rantes production by influenza virus-infected human bronchial epithelial cells". Turkish Archives of Pediatrics, vol. 51, 2016, pp. 63-71 [available via https://www.ncbi.nlm.nih.gov/pmc/articles/PMC4959743/].
Ciftci et al. "Influenza and the use of oseltamivir in children".
International Search Report and Written Opinion mailed on Mar. 13, 2019 in corresponding International Application No. PCT/GB2018/053732.
Search Report issued in corresponding United Kingdom Application No. GB1721793.6.
An SC et al., Triple combinations of neuraminidase inhibitors, statins and fibrates benefit the survival of patients with lethal avian influenza pandemic, Medical Hypotheses, 2011; 77(6): 1054-157.
Armstrong SM et al., Endothelial activation and dysfunction in the pathogenesis of influenza A virus infection, Virulence, 2013; 4(6): 537-542.
Bermejo-Martin JF, et al., Macrolides for the treatment of severe respiratory illness caused by novel H1N1 swine influenza viral strains, J Infect Developing Countries, 2009; 3(3): 159-161.
Brun-Buisson et al., Early corticosteroids in severe influenza A/H1N1 pneumonia and acute respiratory distress syndrome, Am J Respir Crit Care Med. May 1, 2011;183(9):1200-6.

Croft, M., The role of TNF superfamily members in T-cell function and diseases, Nat Rev Immunol, 2009; 9: 271-85.
Darwish et al., Immunomodulatory Therapy for Severe Influenza, Expert Rev Anti Infect Ther., Jul. 2011; 9(7): 807-22, doi: 10.1586/eri.11.56.
Fedson DS, Confronting the next influenza pandemic with anti-inflammatory and immunomodulatory agents: why they are needed and how they might work, Influenza and Other Respiratory Viruses, 2009; 3(4): 129-142.
Fedson DS, Confronting an influenza pandemic with inexpensive generic agents: can it be done?, Lancet Infect. Dis., 2008; 8: 571-76.
Fedson DS, Treating influenza with statins and other immunomodulatory agents, Antiviral Research, 2013; 99(3): 417-435.
Galan-Arriero I, et al. Early treatment with UR13870, a novel inhibitor of p38a mitogenous activated protein kinase, prevents hyperreflexia and anxiety behaviors, in the spared nerve injury model of neuropathic pain. Neurosci. Lett. Sep. 14, 2015;604:69-74.
Hoang et al. (Patient-based transcriptome-wide analysis identify interferon and ubiquitination pathways as potential predictors of influenza A disease severity, PloS One 2014, 9: e111640e).
Hui et al., Adjunctive Therapies and Immunomodulatory Agents in the Management of Severe Influenza, Antiviral Research, 2013; 98: 410-416.
Hui & Lee, Adjunctive Therapies and Immunomodulatory Agents for Severe Influenza, Influenza and Other Respiratory Viruses, 2013; 7 (suppl. 3): 52-59.
Lee, N. et al., Cytokine response patterns in severe pandemic 2009 H1N1 and seasonal influenza among hospitalised adults, PloS One, 2011; 6: e26050.
Lee, N. et al., Outcomes of adults hospitalised with severe influenza, Thorax, 2010; 65: 510-515.
Lee N. et al., Viral clearance and inflammatory response patterns in adults hospitalised for pandemic 2009 influenza A (H1N1) virus pneumonia, Antiviral Therapy, 2011; 16: 237-47.
Liu et al., Cellular & Molecular Immunology, 2015; 1-8, doi: 10.1038/cmi.2015.74.
Mihara K, et al. A potent and selective p38 inhibitor protects against bone damage in murine collagen-induced arthritis: a comparison with neutralization of mouse TNFalpha., Br. J. Pharmacol., May 2008; 154(1):153-64.
Sato K et al., Therapeutic Effect of Erythromycin on Influenza Virus-induced Lung Injury in Mice, Am J Respir Crit Care Med, 1998; 157: 853-857.
Teijaro JR et al., Endothelial Cells are Central Orchestrators of Cytokine Amplification during Influenza Virus Infection, Cell, 2011; 146: 980-991.
Xing, L., MAP Kinase 2015, vol. 4:5508.
Zarubin and Han, Cell Research (2005) 15, 11-18. doi:10.1038/sj.cr.7290257.
WHO factsheet No. 211: https://web.archive.org/web/20160613040907/http://www.who.int/mediacentre/factsheets/fs211/en/.
WHO Guidelines for Pharmacological Management of Pandemic Influenza A(H1N1) 2009 and other Influenza Viruses, Revised Feb. 2010, Part I Recommendations, p. 5.
Soliva et al., Journal of Medicinal Chemistry (2007), 50(2), 283-293.
Bagley et al., Future Medicinal Chemistry (2010), 2(2), 193-201.
Wang et al., Journal of Chemical Information and Modeling (2011), 51(11), 2821-2828.
Office Action dated Dec. 12, 2022 issued in co-pending Israeli Patent Application No. 275573, and its' English Translation.
Office Action issued in co-pending Japanese Patent Application No. 2020-534928, and its' English Translation.
HH Kwok et al., Anti-inflammatory effects of indirubin derivatives on influenza A virus-infected human pulmonary microvascular endothelial cells:, Scientic Reports, 2016, vol. 6, article 18941, DOI: 10.1038/srep18941.
Examination Report issued in corresponding European Application No. 18 829 950.7 dated Nov. 21, 2023.
Examination Report No. 2 issued in corresponding Australian Application No. 2018390132 dated Dec. 18, 2023.

METHODS AND COMPOUNDS FOR THE TREATMENT OR PREVENTION OF SEVERE INFLUENZA

CROSS-REFERENCE TO RELATED APPLICATIONS

This application is a continuation of U.S. application Ser. No. 16/312,784, filed on Jun. 21, 2018 and titled Methods and Compounds for the Treatment or Prevention of Severe Influenza, which is a national stage entry under 35 U.S.C. § 371 of international application no. PCT/GB2017/051865, which was filed on Jun. 26, 2017 and published on Jan. 11, 2018 under publication no. WO 2018/007788, and which claims the benefit of priority under 35 U.S.C. § 119 of Great Britain patent application no. 1611712.9, which was filed on Jul. 2, 2016, the entireties of which are incorporated herein by reference.

FIELD OF THE INVENTION

The present invention relates to methods and compounds for the treatment or prevention of severe influenza. The invention also provides pharmaceutical compositions for the treatment or prevention of severe influenza.

BACKGROUND TO THE INVENTION

Influenza occurs globally with an annual attack rate estimated at 5%-10% in adults and 20%-30% in children. Illnesses can result in hospitalization and death mainly among high-risk groups (the very young, elderly or chronically ill). Worldwide, these annual epidemics are estimated to result in about 3 to 5 million cases of severe illness, and about 250,000 to 500,000 deaths. (See WHO factsheet number 211: A version of this document can be retrieved from the Internet Archive Wayback Machine, at web*archive*org, from the archive of 13 Jun. 2016 of the domain www*who*int, of the page at the path/mediacentre/factsheets/fs211/en/)

In North America, seasonal influenza causes excess hospitalisations in 230-1670 per 100,000 persons aged >65 years, 32,000 respiratory/cardiovascular deaths and 43,000 all-cause deaths annually. Persons with chronic medical conditions (e.g. pulmonary, cardiovascular, liver, renal and neurological diseases, diabetes or immunosuppression) have a >30-fold increase in risk of hospitalisation and death. Among the circulating seasonal influenza subtypes, H3N2 is usually a more frequent cause of severe illness and hospitalisation. (See Lee, N. et al., Outcomes of adults hospitalised with severe influenza, *Thorax,* 2010; 65: 510-515).

The situation can be even worse during influenza pandemics. In early 2009, a novel influenza A/H1N1 virus (pH1N1) emerged and rapidly caused a pandemic. It has been estimated that in some populations, up to 20-40% of individuals were affected and resulted in excessive hospitalizations and deaths. In the United States, 195,000-403,000 people were hospitalized for severe pH1N1 infection and 8,870-18,300 died by April 2010. The pH1N1 virus has continued to co-circulate with the seasonal influenza viruses in the community.

While most patients develop mild upper respiratory-tract infection with pH1N1, some progress to develop severe lower respiratory-tract complications, such, for example, as pneumonia, or transition to experiencing symptoms that do not resolve or improve after several days (>2 days). In contrast to seasonal influenza, young adults and previously healthy individuals may also develop severe respiratory complications such, for example, as pneumonia and acute respiratory distress syndrome (ARDS). Among hospitalized adults, between 9-34% may require intensive care because of progressive respiratory failure, which can be associated with high mortality (14-46%); notably, some of the manifestations (e.g. pneumonia, ARDS, multi-organ failure) are quite similar to those of H5N1 avian influenza. (See Lee, N. et al., Cytokine response patterns in severe pandemic 2009 H1N1 and seasonal influenza among hospitalised adults, PloS One, 2011; 6: e26050).

WO 01/19322 A2 (SmithKline Beecham Corp) claims a method of treating influenza-induced pneumonia which method comprises administering to the human an effective amount of a CBSP/p38 inhibitor.

p38 MAP kinases comprise a mitogen-activated protein kinase subfamily that regulates a variety of cellular processes including cell growth processes, cell differentiation, apoptosis and cellular responses to inflammation. The p38 MAP kinases are regulated by cytokine receptors and can be activated in response to bacterial or viral pathogens.

WO 2004/076450 A1 discloses the use of certain pyrazolopyridine derivatives for the treatment or prevention of diseases mediated by TNF-α, IL-1, IL-6 and/or IL-8, including immune, autoimmune and inflammatory diseases, cardiovascular diseases, infectious diseases, bone resorption disorders, neurodegenerative diseases, proliferative diseases and processes associated with the induction of cyclooxygenase-2.

WO 02/059083 A2 (SmithKline Beecham Corp) claims the use of substituted 2,4,8-trisubstituted-8H-pyrido[2,3-d]pyrimidin-7-one compounds and compositions for treating a wide range of CBSP/p38 kinase mediated diseases, including ARDS, chronic obstructive pulmonary disease and influenza-induced pneumonia.

US 2011/003848 A1 (Butcher) discloses the use of polymorphic form of the p38 MAP kinase inhibitor, N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea, for treating obstructive, restrictive or inflammatory airways diseases of whatever type, etiology or pathogenesis.

Meanwhile, WO 2015/173788 A1 (Westfälische Wilhelms-Universität Münster) claims a MEK inhibitor, p38 inhibitor and/or NF-κB inhibitor for use in a method for the prophylaxis and/or treatment of a co-infection comprising a bacterial infection and an influenza virus infection or a bacterial infection alone.

Generally, as discussed in more detail below, a number of different anti-inflammatory agents have been proposed in the art for treating inflammation associated with influenza infection.

The World Health Organisation (WHO) defines severe influenza as: Influenza in patients who present clinical and/or radiological signs of lower respiratory tract disease, central nervous system (CNS) involvement, severe dehydration or present secondary complications, such as renal failure, multi-organ failure and septic shock (other complications can include rhabdomyolysis and myocarditis); influenza where there is exacerbation of underlying chronic disease; influenza where there is any other condition or clinical presentation that requires hospital admission for clinical management; and influenza where there are any of the following signs and symptoms of progressive disease:

Symptoms and signs suggesting oxygen impairment or cardiopulmonary insufficiency: Shortness of breath (with activity or at rest), difficulty in breathing, tachypnoea, presence of cyanosis, bloody or coloured sputum, chest pain, and low blood pressure; in children, fast or laboured breathing; and hypoxia, as indicated by pulse oximetry or arterial blood gases;

Symptoms and signs suggesting CNS complications: Altered mental status, unconsciousness, drowsiness, or difficult to awaken and recurring or persistent convulsions (seizures), confusion, severe weakness, or paralysis;

Evidence of sustained or spreading virus replication or invasive secondary bacterial infection based on laboratory testing or clinical signs (e.g. persistent or recurrent high fever and other symptoms beyond 2 or 3 days without signs of resolution); and Severe dehydration, manifested as decreased physical or mental activity, dizziness, decreased urine output, and lethargy. (See WHO Guidelines for Pharmacological Management of Pandemic Influenza A(H1N1) 2009 and other Influenza Viruses, Revised February 2010, Part I Recommendations, p. 5).

Uncomplicated influenza is a mild inflammation of the upper respiratory tract. Inflammation is part of the complex biological response of body tissues to harmful stimuli damaging cells, such as viruses, toxins or irritants; it is a protective response that involves the immune system, blood vessels and numerous proteins. The purpose of inflammation is to eliminate the initial cause of cell injury, clear out dead and dying cells and to initiate tissue repair. In uncomplicated influenza the inflammation is short lived and repair to the damaged epithelial cell lining of the upper airways starts about 2-3 days after onset of symptoms.

In contrast to uncomplicated influenza, the inflammatory response in severe influenza is exaggerated or extended respectively. Rather than being protective, the response becomes destructive. High levels of pro-inflammatory proteins (cytokines) in the blood are an early indication of poor clinical outcomes in influenza patients (Lee, N. et al. 2011). In these patients the exaggerated inflammatory response can lead to damage of the blood vessels in the lung and other tissues resulting in leakage of liquid into the tissue (oedema). Accumulation of fluid and immune cells in the lungs can lead to pneumonia, acute lung injury and ARDS and respiratory failure in severe cases. The exaggerated inflammatory response in severe influenza can be viewed as a non-linear process where there is a critical point—a phase transition, or tipping point—when the normal inflammatory response becomes an abnormal or more destructive response. In severe influenza, rather than going down a resolution path after peak symptoms at around day 3 after infection, patients progress to develop other respiratory complications, a process driven by an exaggerated inflammatory response.

Hypercytokinemia is defined as a sudden surge in the circulating levels of pro-inflammatory cytokines, such as IL-1, IL-6 and TNF (Croft, M., The role of TNF superfamily members in T-cell function and diseases, *Nat Rev Immunol,* 2009; 9: 271-85). Hypercytokinemia is seen in severe infections with three major influenza viruses: the pandemic 1918-19 Spanish H1N1 influenza; H5N1 avian influenza and; the pandemic H1N1 influenza of 2009. When compared to human H1N1, H5N1 viruses are more potent inducers of pro-inflammatory cytokines in primary human respiratory epithelial cells, and this hyperinduction of cytokines is likely to contribute to the disease severity of H5N1. The exact mechanism of hypercytokinemia in influenza is unknown, but endothelial cells have been identified as central regulators of "cytokine storm" (Teijaro J R et al., Endothelial Cells are Central Orchestrators of Cytokine Amplification during Influenza Virus Infection, *Cell,* 2011; 146: 980-991).

Armstrong S M et al., Endothelial activation and dysfunction in the pathogenesis of influenza A virus infection, *Virulence,* 2013; 4(6): 537-542, review evidence in support of endothelial activation and dysfunction as a central feature preceding the development of severe influenza.

Using gene expression microarrays to compare the transcriptomic profiles of influenza-infected patients with severe, moderate and mild symptoms with febrile patients of unknown etiology, Hoang et al. (Patient-based transcriptome-wide analysis identify interferon and ubiquination pathways as potential predictors of influenza A disease severity, PloS One 2014, 9: e111640e) reported that influenza-infected patients, regardless of their clinical outcomes, had a stronger induction of antiviral and cytokine responses and a stronger attenuation of NK and T cell responses in comparison with those with unknown etiology and that interferon and ubiquitination signalling were strongly attenuated in patients with the most severe outcomes in comparison with those with moderate and mild outcomes. This agrees with the inventors' own data, which show elevated cytokine levels in serum from patients hospitalised for severe influenza relative to influenza-infected individuals without severe influenza (see Example 5 below).

Hoang et al., 2014 found p38 MAPK signalling to be up-regulated in moderate as well as severe patients. MMP9, SOCS3, IFITMs, TLR10, RIG-I, CD244 and NCR3 were proposed as candidate genes for further studies. However, targeting individual cytokines is unlikely to have broad anti-inflammatory effects that are required, and redundancy in the inflammatory response system means that knocking out multiple cytokines simultaneously is likely to be required for a therapy to be effective.

US 2010/0151042 A1 (Liang et al.) claims a method for reducing the severity, intensity or duration of complications or symptoms associated with an influenza infection, wherein the method comprises diagnosing a subject with the influenza infection; and concurrently administering to the subject an effective amount of a cysteamine compound and a second viral therapeutic. The complications associated with the influenza viral infection may comprise rhinitis, bacterial infections, cardiac complications, neurologic complications, myositis, renal failure, pulmonary fibrosis, exacerbations of asthma, exacerbations of chronic obstructive pulmonary disease, empyema or heart failure. The second viral therapeutic may be selected from the group consisting of: amantadine, rimantadine, ribavirin, idoxuridine, trifluridine, vidarabine, acyclovir, ganciclovir, foscarnet, zidovudine, didanosine, zalcitabine, stavudine, famciclovir, oseltamivir phosphate, zanamivir, valaciclovir, antitussives, mucolytics, expectorants, antipyretics, analgesics and nasal decongestants.

Immunomodulatory therapy for severe influenza has been reviewed by Hui et al., Adjunctive Therapies and Immunomodulatory Agents in the Management of Severe Influenza, *Antiviral Research,* 2013; 98: 410-416; Hui & Lee, Adjunctive Therapies and Immunomodulatory Agents for Severe Influenza, *Influenza and Other Respiratory Viruses,* 2013; 7 (suppl. 3): 52-59; and Liu et al., *Cellular & Molecular Immunology,* 2015; 1-8, doi:10.1038/cmi.2015.74.

Darwish et al., Immunomodulatory Therapy for Severe Influenza, *Expert Rev Anti Infect Ther.,* 2011 (July); 9(7): 807-22, doi:10.1586/eri.11.56, describe the influenza viral and host pathogenicity determinants, present the evidence supporting the use of immunomodulatory therapy to target the host inflammatory response as a means to improve clinical outcome in severe influenza, and review the experimental data on investigational immunomodulatory agents targeting the host inflammatory response in severe influenza, including anti-TNF therapy, statins, glucocorticoids, cyclooxygenase-2 inhibitors, macrolides, peroxisome proliferator-activated receptor agonists, AMP-activated protein kinase agonists and high mobility group box 1 antagonists, concluding with a rationale for the use of mesenchymal stromal (stem) cells and angiopoietin-1 therapy against deleterious influenza-induced host responses that mediate end-organ injury and dysfunction.

Fedson D S, Confronting an influenza pandemic with inexpensive generic agents: can it be done?, *Lancet Infect. Dis.,* 2008; 8: 571-76, proposes research to determine whether statins, fibrates, chloroquines and other generic agents could mitigate the effects of an H5N1 avian influenza A pandemic. See also Fedson D S, Confronting the next influenza pandemic with anti-inflammatory and immunomodulatory agents: why they are needed and how they might work, *Influenza and Other Respiratory Viruses,* 2009; 3(4): 129-142, and Fedson D S, Treating influenza with statins and other immunomodulatory agents, *Antiviral Research,* 2013; 99(3): 417-435.

An S C et al., Triple combinations of neuraminidase inhibitors, statins and fibrates benefit the survival of patients with lethal avian influenza pandemic, *Medical Hypotheses,* 2011; 77(6): 1054-157, hypothesise that statins and fibrates, both of which have anti-inflammatory and immunomodulatory effects and other multiple biologic activities, may exhibit synergistic effects when they were combined to neuraminidase inhibitors to treat the A (H5N1) viruses infections via inhibiting the production of either the early inflammatory mediators (e.g., many cytokine/chemokine) or the late mediator (e.g., High Mobility Group Box Protein 1), even showing the anti-viral activities with the prevention of the development of antiviral resistance.

As described by Bermejo-Martin J F, et al., Macrolides for the treatment of severe respiratory illness caused by novel H1N1 swine influenza viral strains, *J Infect Developing Countries,* 2009; 3(3): 159-161, macrolides are molecules with antibacterial activity that also have remarkably anti-inflammatory properties. They exert both stimulatory and inhibitory effects on leukocytes. These effects seem to be related to the activation state of the leukocytes, facilitating bacterial killing as well as resolving local inflammation. The use of macrolides in the treatment of severe disease caused by the novel H1N1 swine flu reassortment influenza viruses is proposed, particularly in combination with antivirals, in order to diminish the systemic inflammatory response leading to pneumonia and fatal outcome.

Sato K et al., Therapeutic Effect of Erythromycin on Influenza Virus-induced Lung Injury in Mice, *Am J Respir Crit Care Med,* 1998; 157: 853-857, evaluated the use of erythromycin (EM), an antibiotic with potent anti-inflammatory effects that is used for treating chronic lower respiratory tract infections, on influenza-virus-induced pneumonia in mice. It was found that the administration of EM at a dose of 3.3 mg/kg/d (intraperitoneally, from Days 1-6 after infection) significantly improved the survival rate of mice infected with influenza virus, and the survival rate of the virus-infected mice at Day 20 of infection increased in a dose-dependent fashion with EM administered to the animals, from 14% among controls to 42% among animals given EM at 1.0 mg/kg/d and 57% amongst those given EM at 3.3 mg/kg/d.

At the time of the present invention, however, there remains an unmet need for a treatment for severe influenza.

SUMMARY OF THE INVENTION

As described below, especially with reference to the Examples, the inventors have discovered that p38 MAP kinase is upregulated in a number of cellular signalling pathways that are very active in patients with severe influenza in comparison with patients with mild or moderate influenza. In particular, it has been found that p38 MAP kinase is involved in a number of different non-metabolic signalling pathways comprising more than three nodes, in which 100% of the nodes are upregulated in patients with severe influenza versus patients with mild influenza, and at least 75% of the nodes are upregulated in patients with severe influenza versus patients with H1N1 infection or moderate influenza.

p38 MAP kinase is a node that is located high in a signalling cascade in a range of cell types (epithelial, endothelial and immune) which are all important in the pathology of severe influenza Because of the rapid and progressive nature of severe influenza, targeting a protein high in a signalling cascade is required to attenuate inflammatory mediator production quickly and reduce disease progression.

However, while numerous other targetable nodes in 95 pathway routes were identified by the inventors as potential targets for the treatment of severe influenza, it was unexpectedly found that p38 MAP kinase inhibitors exhibit a dose-dependent knockdown effect on the release of cytokines, particularly IP10, from endothelial cells treated with a viral conditioned medium that simulates the action of inflammatory mediators produced from influenza-infected epithelial cells, while other promising potential targets do not show the same effect. In particular, as disclosed by Example 4 below, while p38 MAP kinase inhibitors exhibit dose-dependent inhibition of IP10 in endothelial cells, as well as inhibitory effects on the release of inflammatory mediators from immune cells that are comparable with corticosteroids and macrolides, the next most promising target, namely mitogen-activated protein kinase (MEK), is not effective in inhibiting IP10 release from endothelial cells and actually appears to increase levels of IP10 at higher drug concentrations.

According to one aspect of the present invention therefore there is provided a p38 MAPK inhibitor for use in the treatment or prevention of severe influenza in a human patient.

In another aspect of the present invention there is provided a method of treating or preventing severe influenza in a human patient in need thereof comprising administering to the patient a pharmaceutically effective amount of a p38 MAPK inhibitor.

In particular, the p38 MAPK inhibitor may be used for the treatment or prevention of severe influenza in a human patient by inhibiting the release of pro-inflammatory mediators from endothelial cells.

More specifically, the p38 MAP kinase inhibitor may be used for the treatment or prevention of severe influenza in a human patient by inhibiting the release of pro-inflammatory cytokines from endothelial cells.

In some embodiments, the p38 MAP kinase inhibitor may be used, in accordance with the present invention, for the treatment or prevention of severe influenza in a human patient by inhibiting the release of IP10 from endothelial cells.

Advantageously, the p38 MAP kinase inhibitor may exhibit dose-dependent inhibition of cytokine release from endothelial cells.

As well as its inhibitory effects on cytokine release from endothelial cells, the p38 MAP kinase inhibitor may also act to inhibit the release of pro-inflammatory cytokines from immune cells, which are typically located close to endothelial cells in the lower respiratory tract.

By "severe influenza" herein is meant an illness caused by any influenza virus and leading to lower respiratory tract clinical disease and/or lower respiratory tract inflammation and/or hypercytokinemia (e.g. lung or systemic). As described above, severe influenza is distinct from uncomplicated (mild or moderate) influenza in which the patient typically has clinically tolerable upper and lower respiratory tract symptoms such, for example, as nasal congestion, sneezing, rhinorrhoea, pyrexia (fever) and cough and sputum production, and from which a patient normally recovers naturally without the need for therapeutic intervention. In severe influenza, the patient's inflammatory response to the viral infection is grossly exaggerated or extended, and the patient develops more severe respiratory tract symptoms or clinical complications that may require hospitalization and sometimes result in death. In such cases, early therapeutic intervention is critically important. As indicated by the WHO definition of severe influenza, a wide range of complications can be caused by influenza virus infection of the upper respiratory tract (nasal passages, sinuses, throat) and lower respiratory tract (lungs). Different patients with severe influenza may therefore present with a wide range of different symptoms or signs of the disease. The various symptoms or signs discussed below that are characteristic of severe influenza may be observable or detectable after 2 days of illness; typically, within 2-9 days of illness.

For instance, the severe influenza may be characterised by hypercytokinemia. Typically, the hypercytokinemia may involve elevated levels of one or more cytokines.

In some embodiments, the cytokines may comprise one or more of IL-8, IL-7, IL-6, Eotaxin, IP10, MCP1, MCP4 and VEGF. In particular, in some embodiments, the cytokines may comprise one or more of IL-8, Eotaxin, IP10 and IL-7.

In some embodiments, the cytokines may comprise one or more of IL-6, IL-8 and IP10 (see Lee N. et al., 2011; Lee N. et al., Viral clearance and inflammatory response patterns in adults hospitalised for pandemic 2009 influenza A (H1N1) virus pneumonia, *Antiviral Therapy,* 2011; 16: 237-47).

In some embodiments, the hypercytokinemia may involve an elevated level of IL-6 of greater than about 1.5 or 2 times its plasma reference range (<3.1 pg/ml)—in some embodiments greater than about 10, 15 or 30 times, up to about 54 times or more. Thus, the hypercytokinemia may involve an elevated level of IL-6 of greater than about 4.7 pg/ml. More particularly, the hypercytokinemia involve an elevated level of IL-6 of greater than about 4.7 pg/ml in the case of seasonal flu, and greater than about 7.8 pg/ml in the case of pandemic flu.

In some embodiments, the hypercytokinemia may involve an elevated level of IL-8 of greater than about 1 or 2 times its plasma reference range (<5.0 pg/ml)—in some embodiments greater than about 4 times, up to about 8, 10 or 12 times or more. Thus, the hypercytokinemia may involve an elevated level of IL-8 greater than about 5.0 pg/ml. More particularly, the hypercytokinemia may involve an elevated level of IL-8 of greater than about 5.0 pg/ml in the case of seasonal flu, and greater than about 11.6 pg/mL in the case of pandemic flu.

In some embodiments, the hypercytokinemia may involve an elevated level of IP-10 of greater than about 1 or 2 times its plasma reference range (202-1480 pg/ml)—in some embodiments greater than 1.1 times, greater than 1.5 times or greater than about 2, 3, 4, 5, 6, 7 or 8 times, up to about 10, 20 or 30 times or more. Thus, the hypercytokinemia may involve an elevated level of IP-10 of greater than about 835 pg/ml. More particularly, the hypercytokinemia may involve an elevated level of IP-10 of greater than about 835 pg/ml in the case of pandemic flu, and greater than about 1476 pg/ml in the case of seasonal flu.

In some embodiments, the hypercytokinemia may involve an elevated level of MCP-1 of greater than about 1 or 2 times its plasma reference range (<10.0-57.0 pg/ml)—in some embodiments greater than about 4 times, up to about 5.5 times or more. Thus, the hypercytokinemia may involve an elevated level of MCP-1 of greater than about 52.9 pg/ml. More particularly, the hypercytokinemia may involve an elevated level of MCP-1 of greater than about 52.9 pg/ml in the case of pandemic flu, and greater than about 64.8 pg/ml in the case of seasonal flu.

In some embodiments, the hypercytokinemia may involve an elevated level of sTNFR-1 of greater than about 1 or 2 times its plasma reference range (484-1407 pg/ml), up to about 2.5 times or more. Thus, the hypercytokinemia may involve an elevated level of sTNFR-1 of greater than about 1099.4 pg/ml. More particularly, the hypercytokinemia may involve an elevated level of sTNFR-1 of greater than about 1099.4 pg/ml in the case of seasonal flu, and greater than about 1250.7 pg/ml in the case of pandemic flu.

In some embodiments, the hypercytokinemia may involve an elevated level of MIG of greater than about 1 or than 2 times its plasma reference range (48.0-482.0 pg/ml)—in some embodiments greater than 1.1 times, greater than 1.5 times or greater than 2 times, up to about 15, 40 or 50 times or more. Thus, the hypercytokinemia may involve an elevated level of MIG of greater than about 103.8 pg/ml. More particularly, the hypercytokinemia may involve an elevated level of MIG of greater than about 103.8 pg/ml in the case of seasonal flu, and greater than about 118.7 pg/ml in the case of pandemic flu.

In some embodiments, the hypercytokinemia may involve an elevated level of IL-17A of greater than about 1, 1.5 or 2 times its plasma reference range (<10.0 pg/ml)—in some embodiments greater than 4 times, greater than 5 times or greater than 6 times, up to about 7 times or more. Thus, the hypercytokinemia may involve an elevated level of IL-17A of greater than about 5.0 pg/ml. More particularly, the hypercytokinemia may involve an elevated level of IL-17A of greater than about 5.0 pg/ml in the case of pandemic flu and greater than about 9.3 pg/ml in the case of seasonal flu.

The severe influenza may be characterised in some embodiments by sustained activation of the proinflammatory cytokines (IL-6, IL-8, IP10, MCP-1 and/or sTNFR-1).

Levels of cytokines may be detected in the patient's whole blood, serum, plasma, nasal lavage, nasal secretions or bronchiolar alveolar lavage. Levels of cytokines may be quantified using any suitable technique known to those skilled in the art. Suitably, an enzyme-linked immunosorbent assay (ELISA) or fluorescent automated cell sorting (FACs) may be used. By way of example, a chemiluminescent immunoassay system such, for example, as that which is available from Meso Scale Diagnostics LLC may be employed for its speed and sensitivity. (Information about the system from Meso Scale Diagnostics LLP can be retrieved from the Internet Archive Wayback Machine, at web*archive*org, from the archive of 22 May 2016 of the site at domain www*mesoscale*com.)

Further or alternatively, the severe influenza may be accompanied by significantly higher total white blood cell counts. A patient with severe influenza may have significantly higher absolute neutrophil counts than a patient with mild or moderate influenza. Typically, a patient with severe influenza after 2-9 days of illness may have a neutrophil count in the range $2.1\text{-}24.5 \times 10^3/\mu l$ (as compared with a patient with moderate influenza after 1-9 days of illness who may have a neutrophil count in the range $0.62\text{-}10.88 \times 10^3/\mu l$ or a patient with mild influenza after 3-8 days of illness who may have a neutrophil count in the range $0.5\text{-}6.5 \times 10^3/\mu l$). In some embodiments, the absolute platelet count may be significantly lower in patients with severe disease after 2-9 days of illness, e.g. $27\text{-}250 \times 10^3/\mu l$ (as compared with a patient with moderate influenza after 1-9 days of illness who may have a platelet count in the range $55\text{-}345 \times 10^3/\mu l$ or a patient with mild influenza after 3-8 days of illness who may have a platelet count in the range $79\text{-}370 \times 10^3/\mu l$) (Hoang et al., 2014).

Further, or alternatively, the severe influenza may be characterised by symptoms or signs of hypoxemia or cardiopulmonary insufficiency. In some embodiments, the patient may have an arterial oxygen saturation of ≤92% on room air by a transcutaneous method. Typically, the symptoms or signs of hypoxemia or cardiopulmonary insufficiency may include one or more of dyspnoea, tachypnoea, cyanosis, low blood pressure (designated as below normal range for age and sex) and tachycardia.

In some embodiments, the patient may have tachypnoea (respiratory rate ≥30 for ages ≥12 years, rate ≥40 for ages 6 to 12 years, rate ≥45 for ages 3 to 6 years, rate ≥50 for ages 1 to 3 years).

In some embodiments, the patient may have or show signs of discomfort with breathing or dyspnoea (unable to speak full sentences, appear breathless, using accessory respiratory muscles).

Further, or alternatively, the severe influenza may be characterised by comorbidity with a lower respiratory disorder with or without radiological pulmonary infiltrates.

Further, or alternatively, the severe influenza may be characterised by symptoms or signs suggesting CNS and/or peripheral neuromuscular disorders such, for example, as encephalitis, myelitis or rhabdomyolysis, including altered mental state, unconsciousness, drowsiness, difficult to awaken, recurring convulsions, confusion, muscle pain, severe weakness, paralysis and sensory abnormalities (e.g. tingling in limbs, loss of normal pain sensation).

Still further, or alternatively, the severe influenza may be characterised by severe dehydration. The WHO defines severe dehydration in adults as >9% body weight loss (in children >15%) (K. Sinha and M. Davenport (eds.), Handbook of Pediatric Surgery, doi: 10.1007/978-1-84882-132-3_2.1, Springer-Verlag London Limited 2010). According to the present invention, the severe influenza may involve >9%, for example 10-15%, loss of body fluids.

Further, or alternatively, the severe influenza may be characterised by abnormal levels of fatigue and/or lethargy.

Further, or alternatively, the severe influenza may be characterised by the presence of radiological pulmonary infiltrate.

Still further, or alternatively, the severe influenza involves evidence of sustained viral infection or replication. In some embodiments, the patient may exhibit more than 2 days of constant or increasing viral replication that can be assayed using standard laboratory methods or diagnosed by the identification of persistent or worsening symptoms. In some embodiments, the patient may exhibit 3, 4, 5 or more days of constant or increasing viral replication. Thus, in some embodiments, the severe influenza in accordance with the present invention may be characterized by symptoms that persist or recur for more than 2, 3, 4, 5 or more days without signs of resolution. The symptoms that persist or recur may include fever (i.e. a temperature greater than 100° F./38° C.), lethargy, achiness, congestion, cough, sinus congestion, sinus drainage or upper respiratory congestion or inflammation.

Further, or alternatively, the severe influenza may be characterised by a secondary bacterial infection.

Further, or alternatively, the severe influenza may be characterised by a lower respiratory tract disorder or inflammation.

Further, or alternatively, the severe influenza may be characterised by mono- or multi-organ failure (e.g. respiratory failure or renal failure) or septic shock.

In some embodiments, the patient may be an infant (i.e. less than one year old) or elderly (i.e. 65 years old or more) or may be a pregnant woman.

In some embodiments, the human patient may have one or more underlying comorbidities that predispose the patient to severe influenza. For example, the patient may be immunocompromised, or may suffer from COPD, severe genetic anaemia, asthma or diabetes, chronic hepatic or renal insufficiency, obesity or a cardiovascular disorder or condition.

Thus, in some embodiments, the p38 MAP kinase inhibitor may be administered to the patient prophylactically, especially where the patient is in a "high-risk" or "at-risk" group as mentioned in the preceding paragraphs.

DETAILED DESCRIPTION OF THE INVENTION p38 MAP kinase inhibitors are an established class of active agents (see e.g. Zarubin and Han, *Cell Research* (2005) 15, 11-18. doi:10.1038/sj.cr.7290257). A wide range of p38 MAP kinase inhibitors are available to those skilled in the art (see e.g. Lee, et al., Inhibition of p38 MAP kinase as a therapeutic strategy, *Immunopharmacol.*, 2000; 47(2-3): 185-201. doi:10.1016/S0162-3109(00)00206-X).

Examples of the low molecular p38 MAP kinase inhibitors include pyridinylimidazoles, substituted pyrazoles, pyrazolopyridine derivatives, substituted pyridyls, quinazoline derivatives, aryl ureas, heteroaryl analogues, substituted imidazole compounds and substituted triazole compounds. (See Young P. R. et al., *J. Biol. Chem.*, 1997; 272: 12116-12121 and Bender, P. E., *J. Med. Chem.* 1985, 28; 1169-1177).

Examples of the pyridinylimidazoles capable of inhibiting p38 include 6-(4'-fluorophenyl)-5-(4'-pyridyl)-2,3-dihydro-imidazo(2,1-b)-thiazole and a metabolite thereof (sulfoxide, sulfone), analogue thereof, fragment thereof and mimic thereof. Furthermore, it is proposed that 4-(pyridin-4-yl)-5-phenylimidazole, the smallest structure of the pyridinylimidazoles, could be sufficient to inhibit p38 (see Gallagher, T F et al., *Bio-org. Med. Chem.*, 1997; 5: 49-64).

Particular 1,5-diaryl substituted pyrazole compounds are also proposed as p38 MAP kinase inhibitors. Such substituted pyrazole compounds are disclosed in U.S. Pat. No. 6,509,361 B. Further pyrazole derivatives inhibiting p38 are disclosed in U.S. Pat. No. 6,335,336 B.

Particular pyrazolopyridine derivatives are also proposed as p38 MAP kinase inhibitors. Such pyrazolopyridine derivatives are disclosed in WO 2004/076450 A1. In some embodiments the p38 MAP kinase inhibitor for use in accordance with the present invention may be selected from 4,6-bis(4-fluorophenyl)-5-(4-pyridyl)-1H-pyrazolo[3,4-b] pyridine; 4,6-diphenyl-5-(4-pyridyl)-1H-pyrazolo[3,4-b] pyridine5-(4-pyridyl)-4,6-bis[3-(trifluoromethyl)phenyl]-

1H-pyrazolo[3,4-d]pyridine4,6-bis(4-fluorophenyl)-3-methyl-5-(4-pyridyl)-1H-pyrazolo[3,4-b]pyridine3-methyl-4,6-diphenyl-5-(4-pyridyl)-1H-pyrazolo[3,4-b]pyridine2-ethyl-4,6-bis(4-fluorophenyl)-5-(4-pyridyl)pyrazolo[3,4-b]pyridine1-ethyl-4,6-bis(4-fluorophenyl)-5-(4-pyridyl)pyrazolo[3,4-b]pyridine4,6-bis(4-fluorophenyl)-2-methyl-5-(4-pyridyl)pyrazolo[3,4-b]pyridine4,6-bis(4-fluorophenyl)-1-methyl-5-(4-pyridyl)pyrazolo[3,4-b]pyridine4,6-bis(4-fluorophenyl)-2,3-dimethyl-5-(4-pyridyl)pyrazolo[3,4-b]pyridine4,6-bis(4-fluorophenyl)-1,3-dimethyl-5-(4-pyridyl)pyrazolo[3,4-b]pyridine2-[2-[1-(tert-butoxycarbonyl)piperidin-4-yl]ethyl]-4,6-bis(4-fluorophenyl)-5-(4-pyridyl)pyrazolo[3,4-b]pyridine1-[2-[1-(tert-butoxycarbonyl)piperidin-4-yl]ethyl]-4,6-bis(4-fluorophenyl)-5-(4-pyridyl)pyrazolo[3,4-b]pyridine2-[1-(tert-butoxycarbonyl)piperidin-4-yl]-4,6-bis(4-fluorophenyl)-3-methyl-5-(4-pyridyl)pyrazolo[3,4-b]pyridine1-[1-(tert-butoxycarbonyl)piperidin-4-yl]-4,6-bis(4-fluorophenyl)-3-methyl-5-(4-pyridyppyrazolo[3,4-b]pyridine2-(3-chloropropyl)-4,6-bis(4-fluorophenyl)-5-(4-pyridyl)pyrazolo[3,4-b]pyridine1-(3-chloropropyl)-4,6-bis(4-fluorophenyl)-5-(4-pyridyl)pyrazolo[3,4-b]pyridine3-[4,6-bis(4-fluorophenyl)-5-(4-pyridyl)pyrazolo[3,4-b]pyridin-2-yl]propan-1-ol; 3-[4,6-bis(4-fluorophenyl)-5-(4-pyridyl)pyrazolo[3,4-b]pyridin-1-yl]propan-1-ol2-[1-(tert-butoxycarbonyl)piperidin-4-yl]-4,6-bis(4-fluorophenyl)-5-(4-pyridyl)pyrazolo[3,4-b]pyridine1-[1-(tert-butoxycarbonyl)piperidin-4-yl]-4,6-bis(4-fluorophenyl)-5-(4-pyridyl)pyrazolo[3,4-b]pyridine2-methyl-4,6-diphenyl-5-(4-pyridyl)pyrazolo[3,4-b]pyridine1-methyl-4,6-diphenyl-5-(4-pyridyl)pyrazolo[3,4-b]pyridine4,6-bis(4-fluorophenyl)-5-(4-pyridyl)-2-[2(tetrahydropyran-2-yloxy)ethyl]-pyrazolo[3,4-b]pyridine2-[4,6-bis(4-fluorophenyl)-5-(4-pyridyl)pyrazolo[3,4-b]pyridin-1-yl]ethanol; 4,6-bis(4-fluorophenyl)-2-(4-methylsulfanylbenzyl)-5-(4-pyridyl)pyrazolo[3,4-b]pyridine4,6-bis(4-fluorophenyl)-1-(4-methylsulfanylbenzyl)-5-(4-pyridyl)pyrazolo[3,4-b]pyridine2-[1-(tert-butoxycarbonyl)piperidin-4-ylmethyl]-4,6-bis(4-fluorophenyl)-5-(4-pyridyl)pyrazolo[3,4-b]pyridine1-[1-(tert-butoxycarbonyl)piperidin-4-ylmethyl]-4,6-bis(4-fluorophenyl)-5-(4-pyridyl)pyrazolo[3,4-b]pyridine4,6-bis(4-fluorophenyl)-2-[2-(morpholin-4-yl)ethyl]-5-(4-pyridyl)pyrazolo[3,4-b]pyridine4,6-bis(4-fluorophenyl)-1-[2-(morpholin-4-yl)ethyl]-5-(4-pyridyl)pyrazolo[3,4-b]pyridineethyl 2-[4,6-bis(4-fluorophenyl)-5-(4-pyridyl)pyrazolo[3,4-b]pyridin-2-yl]acetate; ethyl 2-[4,6-bis(4-fluorophenyl)-5-(4-pyridyl)pyrazolo[3,4-b]pyridin-1-yl]acetate; ethyl 3-[4,6-bis(4-fluorophenyl)-5-(4-pyridyl)pyrazolo[3,4-b]pyridin-2-yl]propionate; ethyl 3-[4,6-bis(4-fluorophenyl)-5-(4-pyridyl)pyrazolo[3,4-b]pyridin-1-yl]propionate; 4,6-bis(4-fluorophenyl)-2-(4-piperidyl)-5-(4-pyridyl)pyrazolo[3,4-b]pyridine4,6-bis(4-fluorophenyl)-1-(4-piperidyl)-5-(4-pyridyl)pyrazolo[3,4-b]pyridine4,6-bis(4-fluorophenyl)-2-(4-piperidylmethyl)-5-(4-pyridyl)pyrazolo[3,4-b]pyridine; 4,6-bis(4-fluorophenyl)-1-(4-piperidylmethyl)-5-(4-pyridyl)pyrazolo[3,4-b]pyridine; 4,6-bis(6-chloropyridin-3-yl)-5-(4-pyridyl)-1H-pyrazolo[3,4-b]pyridine4,6-bis(4-fluorophenyl)-3-methyl-2-(4-piperidyl)-5-(4-pyridyl)pyrazolo[3,4-b]pyridine4,6-bis(4-fluorophenyl)-3-methyl-1-(4-piperidyl)-5-(4-pyridyl)pyrazolo[3,4-o]pyridine4l6-bis(4-fluorophenyl)-2-[2-(4-piperidyl)ethyl]-5-(4-pyridyl)pyrazolo[3,4-b]pyridine2-[4,6-bis(4-fluorophenyl)-5-(4-pyridyl)pyrazolo[3,4-b]pyridin-2-yl]acetic acid2-[4,6-bis(4-fluorophenyl)-5-(4-pyridyl)pyrazolo[3,4-b]pyridin-1-yl]acetic acid3-[4,6-bis(4-fluorophenyl)-5-(4-pyridyl)pyrazolo[3,4-b]pyridin-2-yl]propionic acid; 3-[4,6-bis(4-pyridyl)pyrazolo[3,4-b]pyridin-1-yl]propionic acid; 2-[4,6-bis(4-fluorophenyl)-5-(4-pyridyl)pyrazolo[3,4-b]pyridin-2-yl]-1-(morpholin-4 yl)ethanone2-[4,6-bis(4-fluorophenyl)-5-(4-pyridyl)pyrazolo[3,4-b]pyridin-1-yl]acetamide2-[4,6-bis(4-fluorophenyl)-5-(4-pyridyl)pyrazolo[3,4-b]pyridin-1-yl]-1-morpholin-4yl)ethanone3-[4,6-bis(4-fluorophenyl)-5-(4-pyridyl)pyrazolo[3,4-b]pyridin-2-yl]-1-(morpholin-4 yl)propan-1-one3-[4,6-bis(4-fluorophenyl)-5-(4-pyridyl)pyrazolo[3,4-b]pyridin-1-yl]-N-propylpropionamide3-[4,6-bis(4-fluorophenyl)-5-(4-pyridyl)pyrazolo[3,4-b]pyridin-1-yl]-1-(morpholin-4yl)propan-1-one4,6-bis(4-fluorophenyl)-2-(4-methylsulfanylphenyl)-5-(4-pyridyl)pyrazolo[3,4-b]pyridine4,6-bis(4-fluorophenyl)-1-(4-methylsulfanylphenyl)-5-(4-pyridyl)pyrazolo[3,4-b]pyridine4,6-bis(4-fluorophenyl)-2-(4-methylsulfinylphenyl)-5-(4-pyridyl)pyrazolo[3,4-b]pyridine4,6-bis(4-fluorophenyl)-2-(4-methylsulfonylphenyl)-5-(4-pyridyl)pyrazolo[3,4-b]pyridine4,6-bis(4-fluorophenyl)-1-(4-methylsulfinylphenyl)-5-(4-pyridyl)pyrazolo[3,4-b]pyridine4,6-bis(4-fluorophenyl)-2-(4-methylsulfinylbenzyl)-5-(4-pyridyl)pyrazolo[3,4-b]pyridine4,6-bis(4-fluorophenyl)-2-(4-methylsulfonylbenzyl)-5-(4-pyridyl)pyrazolo[3,4-b]pyridine4,6-bis(4-fluorophenyl)-1-(4-methylsulfinylbenzyl)-5-(4-pyridyl)pyrazolo[3,4-b]pyridine4,6-bis(4-fluorophenyl)-1-(4-methylsulfonylbenzyl)-5-(4-pyridyl)pyrazolo[3,4-b]pyridine3-chloro-4,6-bis(4-fluorophenyl)-5-(4-pyridyl)-1H-pyrazolo[3,4-b]pyridine3-bromo-4,6-bis(4-fluorophenyl)-5-(4-pyridyl)-1H-pyrazolo[3,4-b]pyridine4,6-bis(4-fluorophenyl)-5-(4-pyridyl)-1H-pyrazolo[3,4-b]pyridine-3-carbonitrile3-bromo-4,6-bis(4-fluorophenyl)-1-methyl-5-(4-pyridyl)pyrazolo[3,4-b]pyridine4,6-bis(4-fluorophenyl)-5-(4-pyridyl)-1H-pyrazolo[3,4-b]pyridine-3-carboxamide3-aminomethyl-4,6-bis(4-fluorophenyl)-5-(4-pyridyl)-1H-pyrazolo[3,4-b]pyridine4,6-bis(4-fluoro-3-nitrophenyl)-5-(4-pyridyl)-1H-pyrazolo[3,4-b]pyridine3-amino-6-(4-fluorophenyl)-5-(4-pyridyl)-1H-pyrazolo[3,4-b]pyridine3-amino-6-(4-fluorophenyl)-1-methyl-5-(4-pyridyl)pyrazolo[3,4-b]pyridine4-[6-(4-fluorophenyl)-5-(4-pyridyl)-1H-pyrazolo[3,4-b]pyridin-4-yl]phenol2-(2,2-diethoxyethyl)-4,6-bis(4-fluorophenyl)-5-(4-pyridyl)pyrazolo[3,4-b]pyridine1-(2,2-diethoxyethyl)-4,6-bis(4-fluorophenyl)-5-(4-pyridyl)pyrazolo[3,4-b]pyridine; 4,6-bis(4-fluorophenyl)-1-methyl-5-(4-pyridyl)pyrazolo[3,4-b]pyridine-3-carbonitrile3-bromo-6-(4-pyridyl)-1H-pyrazolo[3,4-b]pyridine6-fluorophenyl-5-(4-pyridyl)-1H-pyrazolo[3,4-b]pyridineN-methyl-[3-[4,6-bis(4-fluorophenyl)-5-(4-pyridyl)-pyrazolo[3,4-b]pyridin-2-yl]propyl]amine[4,6-bis(4-fluorophenyl)-5-(4-pyridyl)pyrazolo[3,4-b]pyridin-2-yl]methanol2-[4,6-bis(4-fluorophenyl)-5-(4-pyridyl)pyrazolo[3,4-b]pyridin-2-yl]-N,N-dimethylacetamide2-[4,6-bis(4-fluorophenyl)-5-(4-pyridyl)pyrazolo[3,4-b]pyridin-1-yl]-N,N-dimethylacetamide4,6-bis(4-fluorophenyl)-2-[2-(2-methoxyethoxy)ethyl]-5-(4-pyridyl)pyrazolo[3,4-b]pyridine4,6-bis(4-fluorophenyl)-1-[2-(2-methoxyethoxy)ethyl]-5-(4-pyridyl)pyrazolo[3,4-b]pyridine4,6-bis(4-fluorophenyl)-2-[3-(morpholin-4-yl)propyl]-5-(4-pyridyl)pyrazolo[3,4-b]pyridine4,6-bis(6-chloropyridin-3-yl)-2-methyl-5-(4-pyridyl)pyrazolo[3,4-b]pyridine4,6-bis(6-chloropyridin-3-yl)-1-methyl-5-(4-pyridyl)pyrazolo[3,4-b]pyridine4,6-bis(6-chloropyridin-3-yl)-3-methyl-5-(4-pyridyl)-1H-pyrazolo[3,4-b]pyridine4,6-bis(6-methylpyridin-3-yl)-5-(4-pyridyl)-1H-pyrazolo[3,4-b]pyridine4,6-bis(4-fluorophenyl)-2-(2-phtalimidoethyl)-5-(4-pyridyl)pyrazolo[3,4-b]pyridine2-(2-aminoethyl)-4,6-bis (4-fluorophenyl)-5-(4-pyridyl)pyrazolo[3,4-b]pyridine2-[4,6-bis(4-fluorophenyl)-5-(4-pyridyl)pyrazolo[3,4-b]pyridin-2-yl]ethanol6-(4-fluorophenyl)-2-methyl-5-(4-pyridyl)pyrazolo[3,4-b]pyridine4,6-bis(4-fluorophenyl)-2-(3-phtalimidopropyl)-5-(4-pyridyl)pyrazolo[3,4-b]pyridine2-[4,6-bis(4-fluorophenyl)-5-(4-pyridyl)pyrazolo[3,4-b]pyridin-2-yl]acetaldehyde2-(3-aminopropyl)-4,6-bis(4-fluorophenyl)-5-(4-pyridyl)pyrazolo[3,4-b]pyridine; N-[4,6-bis(4-fluorophenyl)-5-(4-pyridyl)-1H-pyrazolo[3,4-b]pyridin-3-ylmethyl]-1-(tert-butoxycarbonyl)piperidine-4-carboxamideN[4,6-bis(4-fluorophenyl)-5-(4-pyridyl)-1H-pyrazolo[3,4-b]pyridin-3-ylmethyl]-1H-piperidine-4-carboxamidc2-(3-benzyloxypropyl)-4,6-bis(4-fluorophenyl)-5-(4-pyridyl)pyrazolo[3,4-b]pyridine; 1-(3-benzyloxypropyl)-4,6-bis(4-fluorophenyl)-5-(4-pyridyl)pyrazolo[3,4-b]pyridineN,N-diethyl-[2-4,6-bis(4-fluorophenyl)-5-(4-pyridyl)pyrazolo[3,4-b]pyridin-2-yl]ethyl]amineN,N-diethyl-[2-[4,6-bis(4-fluorophenyl)-5-(4-pyridyl)pyrazolo[3,4-b]pyridin-1-yl]ethyl]amine4,6-bis(4-fluorophenyl)-5-(4-pyridyl)-2-(3-pyridylrriethyl)pyrazolo[3,4-b]pyridine4,6-bis(4-fluorophenyl)-5-(4-pyridyl)-1-pyridin-3-ylmethylpyrazolo[3,4-b]pyridineN,N-dimethyl-[3-[4,6-bis(4-fluorophenyl)-5-(4-pyridyl)-pyrazolo[3,4-b]pyridin-2-yl]propyl]amineN,N-dimethyl-[3-[4,6-bis(4-fluorophenyl)-5-(4-pyridyl)-pyrazolo[3,4-b]pyridin-1-yl]propyl]amine1-[2-[4,6-bis(4-fluorophenyl)-5-(4-pyridyl)pyrazolo[3,4-b]pyridin-2-yl]ethyl]piperidin-4-ol3-[4,6-bis(4-fluorophenyl)-5-(4-pyridyl)pyrazolo[3,4-b]pyridin-2-yl]-2-hydroxypropan-1-ol3-[4,6-bis(4-fluorophenyl)-5-(4-pyridyl)pyrazolo[3,4-b]pyridin-1-yl]-2-hydroxypropan-1-ol4,6-bis(4-fluorophenyl)-5-(4-pyridyl)-2-(4-pyridylmethyl)pyrazolo[3,4-b]pyridine; 4,6-bis(4-fluorophenyl)-5-(4-pyridyl)-1-(4-pyridylmethyl)pyrazolo[3,4-b]pyridineN-(tert-butoxycarbonyl)-[1-[3-[4,6-bis(4-fluorophenyl)-5-(4-pyridyl)pyrazolo[3,4-b]pyridin-2-yl]propyl]piperidin-4-yl]amine2-[1-(tert-butoxycarbonyl)piperidin-4-yl]-6-(4-fluorophenyl)-5-(4-pyridyl)pyrazolo[3,4-b]pyridine1-[1-(tert-butoxycarbonyl)piperidin-4-yl]-6-(4-fluorophenyl)-5-(4-pyridyl)pyrazolo[3,4-b]pyridine3-methyl-4,6-bis(6-methylpyridin-3-yl)-5-(4-pyridyl)-1H-pyrazolo[3,4-b]pyridine1-[3-[4,6-bis(4-fluorophenyl)-5-(4-pyridyl)pyrazolo[3,4-b]pyridin-2-yl]-propyl]piperidin-4-oneN-(tert-butoxycarbonyl)-[1-[2-[4,6-bis(4-fluorophenyl)-5-(4-pyridyl)pyrazolo[3,4-b]pyridin-2-yl]ethyl]piperidin-4-yl]amineN-methyl-[1-[2-[4,6-bis(4-fluorophenyl)-5-(4-pyridyl)-pyrazolo[3,4-b]pyridin-2-yl]ethyl]piperidin-4-yl]amine[1-[3-[4,6-bis(4-fluorophenyl)-5-(4-pyridyl)pyrazolo[3,4-b]pyridin-2-yl]propyl]piperidin-4-yl]amine2-[1-[2-[4,6-bis(4-fluorophenyl)-5-(4-pyridyl)pyrazolo[3,4-b]pyridin-2-yl]ethyl]piperidin-4-yl]ethanol1-[2-[4,6-bis(4-fluorophenyl)-5-(4-pyridyl)pyrazolo[3,4-b]pyridin-2-yl]ethyl]piperidin-4-yl]amine6-(4-fluorophenyl)-2-(4-piperidyl)-5-(4-pyridyl)pyrazolo[3,4-b]pyridine6-(4-fluorophenyl)-1-(4-piperidyl)-5-(4-pyridyl)pyrazolo[3,4-b]pyridine3-amino-5-[2-(methylsulfanyl)pyrimidin-4-yl]-6-[3-(trifluoromethyl)phenyl]-1H-pyrazolo[3,4-b]pyridine2-[3-[1-(4-tert-butoxycarbonyl)piperazin-1-yl]propyl3-4,6-bis(4-fluorophenyl)-5-(4-pyridyl)pyrazolo[3,4-b]pyridine4,6-bis(4-fluorophenyl)-2-[3-(1-piperazin-1-yl)propyl]-5-(4-pyridyl)pyrazolo[3,4-b]pyridine5-[2-(methylsulfanyl)pyrimidin-4-yl]-6-[3-(trifluoromethyl)phenyl]-1H-pyrazolo[3,4-b]pyridine5-[2-(methylsulfonyl)pyrimidin-4-yl]-6-[3-(trifluoromethyl)phenyl]-1H-pyrazolo[3,4-b]pyridine(1S)—N-(1-phenylethyl)-[4-[6-[3-(trifluoromethyl)phenyl]-1H-pyrazolo[3,4-b]pyridin-5-yl]pyrimidin-2-yl]amine1-[3-[4,6-bis(4-fluorophenyl)-5-(4-pyridyl)pyrazolo[3,4-b]pyridin-2-yl]propyl]piperidin-4-ol2-[1-[3-[4,6-bis(4-fluorophenyl)-5-(4-pyridyppyrazolo[3,4-b]pyridin-2-yl]propyl]piperidin-4-yl]ethanol4,6-bis(4-fluorophenyl)-3-(4-piperidyl)-5-(4-pyridyl)-1H-pyrazolo[3,4-b]pyridine6-(4-fluorophenyl)-5-(4-pyridyl)-1H-pyrazolo[3,4-b]pyridine-3-carbonitrile2-[2-[[1-(tert-butoxycarbonyl)piperidin-4-yl]amino]ethyl]-4,6-bis(4-fluorophenyl)-5-(4-pyridyl)pyrazolo[3,4-b]pyridine4,6-bis(4-fluorophenyl)-2-[2-[2-[(4-piperidyl)amino]ethyl]-5-(4-pyridyl)pyrazolo[3,4-b]pyridineN-(2-methoxyethyl)-[2-[4,6-bis(4-fluorophenyl)-5-(4-pyridyl)pyrazolo[3,4-b]pyridin-2-yl]ethyl]amine1-[4-[2-[4,6-bis(4-fluorophenyl)-5-(4-pyridyl)pyrazolo[3,4-b]pyridin-2-yl]ethyl]piperazin-1-yl]ethanone3-[4,6-diphenyl-5-(4-pyridyl)pyrazolo[3,4-b]pyridin-2-yl]propan-1-ol3-[4,6-diphenyl-5-(4-pyridyl)pyrazolo[3,4-b]pyridin-1-yl]propan-1-ol2-ethyl-4,6-diphenyl-5-(4-pyridyl)pyrazolo[3,4-b]pyridine1-ethyl-4,6-diphenyl-5-(4-pyridyl)pyrazolo[3,4-b]pyridine4,6-diphenyl-2-(2-phtalimidoethyl)-5-(4pyridyl)pyrazolo[3,4-b]pyridine2-(2-aminoethyl)-4,6-diphenyl-5-(4-pyridyl)pyrazolo[3,4-b]pyridine2-allyl-4,6-bis(4-fluorophenyl)-5-(4-pyridyl)pyrazolo[3,4-b]pyridine1-allyl-4,6-bis(4-fluorophenyl)-5-(4-pyridyl)pyrazolo[3,4-b]pyridine1-2-[4,6-bis(4-fluorophenyl)-5-(4-pyridyl)pyrazolo[3,4-b]pyridin-2-yl]ethyl]piperidin-4-one3-aminomethyl-6-(4-fluorophenyl)-5-(4-pyridyl)-1H-pyrazolo[3,4-b]pyridine3-amino-6-(4-fluorophenyl)-4-methyl-5-(4-pyridyl)-1H-pyrazolo[3,4-b]pyridine; 3-[N-[2-[4,6-bis(4-fluorophenyl)-5-(4-pyridyl)pyrazolo[3,4-b]pyridin-2-yl]ethyl]amino]propan-1-olN-ethyl-[2-[4,6-bis(4-fluorophenyl)-5-(4-pyridyl)pyrazolo[3,4-b]pyridin-2-yl]ethyl]amine2[N/-[2-[4,6-bis(4-fluorophenyl)-5-(4-pyridyl)pyrazolo[3,4-b]pyridin-2-yl]ethyl]amino]ethanolN-[(2-pyridyl)methyl]-[2-[4,6-bis(4-fluorophenyl)-5-(4-pyridyl)pyrazolo[3,4-b]pyridin-2-yl]ethyl]amineN-[(2-thienyl)methyl]-[2-[4,6-bis(4-fluorophenyl)-5-(4-pyridyl)pyrazolo[3,4-b]pyridin-2-yl]ethyl]amine1-[2-[4,6-bis(4-fluorophenyl)-5-(4-pyridyl)pyrazolo[3,4-b]pyridin-2-yl]ethyl]piperidine-4-carboxamide4,6-bis(4-fluorophenyl)-2-[2-(pyrrolidin-1-yl)ethyl]-5-(4-pyridyl)pyrazolo[3,4-b]pyridine(3R)-1-[2-[4,6-bis(4-fluorophenyl)-5-(4-pyridyl)pyrazolo[3,4-b]pyridin-2-yl]ethyl]pyrrolidin-3-ol2-[N-[2-[4,6-bis(4-fluorophenyl)-5-(4-pyridyl)pyrazolo[3,4-b]pyridin-2-yl]ethyl]-N-methylamino]ethanol4,6-bis(4-fluorophenyl)-5-(4-pyridyl)-2-[2-(1,2,3,4-tetrahydroisoquinolin-2-yl)ethyl]pyrazolo[3,4-b]pyridine4,6-bis(4-fluorophenyl)-2-[2-(4-phenylpiperazin-1-yl)ethyl]-5-(4-pyridyl)pyrazolo[3,4-b]pyridine4,6-bis(4-fluorophenyl)-2-[2-[4-(1-piperidyl)piperidin-1-yl]ethyl]-5-(4-pyridyl)pyrazolo[3,4-b]pyridine3-[N-[2-[4,6-bis(4-fluorophenyl)-5-(4-pyridyl)pyrazolo[3,4-b]pyridin-2-yl]ethyl]-N-methylamino]propiononitrileN-methyl-[2-[4,6-bis(4-fluorophenyl)-5-(4-pyridyl)pyrazolo[3,4-b]pyridin-2-yl]ethyl]amine2-[2-[4-(tert-butoxycarbonyl)piperazin-1-yl]ethyl]-4,6-bis(4-fluorophenyl)-5-(4-pyridyl)pyrazolo[3,4-b]pyridine4,6-bis(4-fluorophenyl)-2-[2-(piperazin-1-yl)ethyl]-5-(4-pyridyl)pyrazolo[3,4-b]pyridine4,6-bis(4-fluorophenyl)-5-(4-pyridyl)-2-vinylpyrazolo[3,4-b]pyridine2-[N-2-[4,6-bis(4-fluorophenyl)-5-(4-pyridyppyrazolo[3,4-b]pyridin-2-yl]ethyl]-N-(2-hydroxyethyl)amino]ethanolN-cyclopropyl-[2-[4,6-bis(4-fluorophenyl)-5-(4-pyridyl)pyrazolo[3,4-b]pyridin-2-yl]ethyl]amineN-[2-[4,6-bis(4-fluorophenyl)-5-(4-pyridyl)pyrazolo[3,4-b]pyridin-2-yl]ethyl]acetamideN-[2-[4,6-bis(4-fluorophenyl)-5-(4-pyridyl)pyrazolo[3,4-b]pyridin-2-yl]ethyl]-n'-isopropylureaN-[2-[4,6-bis(4-fluorophenyl)-5-(4-pyridyl)pyrazolo[3,4-b]pyridin-2-yl]ethyl]methanesulfonamide6-(4-fluorophenyl)-4-(4-piperidyl)-5-(4-pyridyl)-1H-pyrazolo[3,4-b]pyridine6-(4-fluorophenyl)-

4-(2-furyl)-5-(4-pyridyl)-1H-pyrazolo[3,4-b]pyridine6-(4-fluorophenyl)-4-(1H-imidazol-4-yl)-5-(4-pyridyl)-1H-pyrazolo[3,4-b]pyridine4-(5-bromothien-2-yl)-6-(4-fluorophenyl)-5-(4-pyridyl)-1H-pyrazolo[3,4-b]pyridine; 4,6-bis(4-fluorophenyl)-5-(2-methylsulfanylpyrimidin-4-yl)-1H-pyrazolo[3,4-b]pyridine5-(2-chloropyridin-4-yl)-4,6-bis(4-fluorophenyl)-1H-pyrazolo[3,4-b]pyridine6-(4-fluorophenyl)-4-(2-phenylethyl)-5-(4-pyridyl)-1H-pyrazolo[3,4-b]pyridine4-(6-chloropyridin-3-yl)-6-(4-fluorophenyl)-5-(4-pyridyl)-1H-pyrazolo[3,4-b]pyridine; 4-(3,4-dichlorophenyl)-1-ethyl-6-(4-fluorophenyl)-5-(4-pyridyl)pyrazolo[3,4-b]pyridine6-(4-fluorophenyl)-4-(1-methylpiperidin-4-yl)-5-(4-pyridyl)-1H-pyrazolo[3,4-b]pyridine3-amino-6-(4-fluorophenyl)-5-(2-methylsulfanylpyrimidin-4-yl)-1H-pyrazolo[3,4-b]pyridine6-(4-fluorophenyl)-5-(2-methylsulfanylpyrimidin-4-yl)-1H-pyrazolo[3,4-b]pyridine4,6-diphenyl-5-(4-pyridyl)-2-[2-(tetrahydropyran-2-yloxy)ethyl]pyrazolo[3,4-b]pyridine6-(4-fluorophenyl)-4-(2-furyl)-2-methyl-5-(4-pyridyl)pyrazolo[3,4-b]pyridine6-(4-fluorophenyl)-2-methyl-4-(1-methyl-1H-imidazol-4-yl)-5-(4-pyridyl)pyrazolo[3,4-b]pyridine6-(4-fluorophenyl)-5-(2-methylsulfanylpyrimidin-4-yl)-2-[2-(tetrahydropyran-2-yloxy)ethyl]pyrazolo[3,4-b]pyridine6-(4-fluorophenyl)-5-(2-methylsulfanylpyrimidin-4-yl)-2-[3-(tetrahydropyran-2-yloxy)propyl]pyrazolo[3,4-b]pyridine4,6-bis(4-fluorophenyl)-5-(2-methylsulfanylpyrimidin-4-yl)-2-[3-(tetrahydropyran-2-yloxy)propyl]pyrazolo[3,4-b]pyridine4-(5-bromothien-2-yl)-6-(4-fluorophenyl)-2-methyl-5-(4-pyridyl)-1H-pyrazolo[3,4-b]pyridine6-(4-fluorophenyl)-2-methyl-5-(2-methylsulfanylpyrimidin-4-yl)pyrazolo[3,4-b]pyridine5-(2-chloropyridin-4-yl)-4,6-bis(4-fluorophenyl)-2-methylpyrazolo[3,4-b]pyridine; 6-(4-fluorophenyl)-4-(2-phenylethyl)-5-(4-pyridyl)-2-[3-(tetrahydropyran-2-yloxy)propyl]pyrazolo[3,4-b]pyridine4-(6-chloropyridin-3-yl)-6-(4-fluorophenyl)-5-(4-pyridyl)-2-[3-(tetrahydropyran-2-yloxy)propyl]pyrazolo[3,4-b]pyridine4-(6-chloropyridin-3-yl)-6-(4-fluorophenyl)-2-methyl-5-(4-pyridyl)pyrazolo[3,4-b]pyridine5-(2-methylsulfanylpyrimidin-4-yl)-2-[3-(tetrahydropyran-2-yloxy)propyl]-6-(3-trifluoromethylphenyl)pyrazolo[3,4-b]pyridine6-(4-fluorophenyl)-2-methyl-5-(4-pyridyl)-4-[5-(3-pyridyl)thien-2-yl]pyrazolo[3,4-b]pyridine2[4,6-diphenyl-5-(4-pyridyl)pyrazolo[3,4-b]pyridin-2-yl]ethanol3-[5-(2-methylsulfanylpyrimidin-4-yl)-6-(3-trifluoromethylphenyl)pyrazolo[3,4-b]pyridin-2-yl]propan-1-ol2-[6-(4-fluorophenyl)-5-(2-methylsulfanylpyrimidin-4-yl)pyrazolo[3,4-b]pyridin-2-yl]ethanol3-[6-(4-fluorophenyl)-5-(2-methylsulfanylpyrimidin-4-yl)pyrazolo[3,4-b]pyridin-2-yl]propan-1-ol3-[4,6-bis(4-fluorophenyl)-5-(2-methylsulfanylpyrimidin-4-yl)pyrazolo[3,4-b]pyridin-2-yl]propan-1-ol3-[6-(4-fluorophenyl)-4-(2-phenylethyl)-5-(4-pyridyl)pyrazolo[3,4-b]pyridin-2-yl]propan-1-ol3-[4-(6-chloropyridin-3-yl)-6-(4-fluorophenyl)-5-(4-pyridyl)pyrazolo[3,4-b]pyridin-2-yl]propan-1-ol6-(4-fluorophenyl)-2-methyl-5-(2-methylsulfonylpyrimidin-4-yl)pyrazolo[3,4-b]pyridine3-[5-(2-methylsulfonylpyrimidin-4-yl)-6-(3-trifluoromethylphenyl)pyrazolo[3,4-b]pyridin-2-yl]propan-1-ol2-[6-(4-fluorophcnyl)-5-(2-methylsulfonylpyrimidin-4-yl)pyrazolo[3,4-b]pyridin-2-yl]ethanol3-[6-(4-fluorophenyl)-5-(2-methylsulfonylpyrimidin-4-yl)pyrazolo[3,4-b]pyridin-2-yl]propan-1-ol3-[4,6-bis(4-fluorophenyl)-5-(2-methylsulfonylpyrimidin-4-yl)pyrazolo[3,4-b]pyridin-2-yl]propan-1-olN-cyclopropylmethyl-[4-[5-[3-(trifluoromethyl)phenyl]-1H-pyrazolo[3,4-b]pyridin-5-yl]pyrimidin-2-yl]amine(1 S)-3-[5-[2-(1-phenylethylamino)pyrimidin-4-yl]-6-(3-trifluoromethylphenyl)pyrazolo[3,4-b]pyridin-2-yl]propan-1-olN-cyclopropylmethyl-[4-[6-(4-fluorophenyl)-2-methyl-pyrazolo[3,4-b]pyridin-5-yl]pyrimidin-2-yl]amine2-[5-[2[(cyclopropylmethyl)amino]pyrimidin-4-yl]-6-(4-fluorophenyl)pyrazolo[3,4-b]pyridin-2-yl]ethanol3-[5-[2-(cyclopropylmethyl)amino]pyrimidin-4-yl]-6-(4-fluorophenyl)pyrazolo[3,4-b]pyridin-2-yl]propan-1-ol3-[5-[2-[(cyclopropylmethyl)amino]pyrimidin-4-yl]-4,6-bis(4-fluorophenyl)pyrazolo[3,4-b]pyridin-2-yl]propan-1-ol4-[4-[4,6-bis(4-fluorophenyl)-2-methylpyrazolo[3,4-b]pyridin-5-yl]pyridin-2-ylamino]benzenesulfonamide4,6-bis(4-fluorophenyl)-5-(4-pyridyl)pyrazolo[3,4-b]pyridin-3-ol6-(4-fluorophenyl)-4-(3H-imidazol-4-yl)-5-(4-pyridyl)-1H-pyrazolo[3,4-b]pyridine6-(4-fluorophenyl)-4-(1H-pyrazol-3-yl)-5-(4-pyridyl)-1H-pyrazolo[3,4-b]pyridine3-[6-(4-fluorophenyl)-5-(4-pyridyl)-1H-pyrazolo[3,4-b]pyridin-4-yl]phenol4-cyclopropyl-6-(4-fluorophenyl)-5-(4-pyridyl)-1H-pyrazolo[3,4-b]pyridine6-(4-fluorophenyl)-4-(5-methylfuran-2-yl)-5-(4-pyridyl)-1H-pyrazolo[3,4-b]pyridine4-(5-bromofuran-2-yl)-6-(4-fluorophenyl)-5-(4-pyridyl)-1H-pyrazolo[3,4-b]pyridine4-(4-benzyloxyphenyl)-6-(4-fluorophenyl)-5-pyrimidin-4-yl-1H-pyrazolo[3,4-b]pyridine4-(4-benzyloxyphenyl)-6-(4-fluorophenyl)-5-(2-methylsulfanylpyrimidin-4-yl)-1H-pyrazolo[3,4-b]pyridine6-(4-fluorophenyl)-4-propyl-5-(4-pyridyl)-1H-pyrazolo[3,4-b]pyridine4-(3-benzyloxyphenyl)-6-(4-fluorophenyl)-5-(4-pyridyl)-1H-pyrazolo[3,4-b]pyridine5-(2-chloropyridin-4-yl)-6-(4-fluorophenyl)-1H-pyrazolo[3,4-b]pyridine4-[6-(4-fluorophenyl)-5-(4-pyridyl)-1H-pyrazolo[3,4-b]pyridin-4-yl]butan-1-ol4-benzyl-6-(4-fluorophenyl)-5-(4-pyridyl)-1H-pyrazolo[3,4-b]pyridine4-(4-benzyloxyphenyl)-6-(4-fluorophenyl)-5-(4-pyridyl)-1H-pyrazolo[3,4-b]pyridine4,6-bis(4-fluorophenyl)-5-pyrimidin-4-yl-1H-pyrazolo[3,4-b]pyridine[(2S)-2-[4,6-bis(4-fluorophenyl)-5-(4-pyridyl)pyrazolo[3,4-b]pyridin-2-yl]ethyl]pyrrolidine-2-carboxamide2-[2-(4,6-diphenyl-5-(4-pyridyl)pyrazolo[3,4-b]pyridin-2-yl)ethylamino]ethanol6-(4-fluorophenyl)-2-methyl-4-(3-pyridyl)-5-(4-pyridyl)pyrazolo[3,4-b]pyridine6-(4-fluorophenyl)-3-methyl-5-(2-methylsulfanylpyrimidin-4-yl)-1H-pyrazolo[3,4-b]pyridine3-amino-5-(2-methylsulfanylpyrimidin-4-yl)-6-phenyl-1H-pyrazolo[3,4-b]pyridine5-(2-methylsulfanylpyrimidin-4-yl)-6-phenyl-1H-pyrazolo[3,4-b]pyridine6-(4-fluorophenyl)-4-methyl-5-(2-methylsulfanylpyrimidin-4-yl)-1H-pyrazolo[3,4-b]pyridine5-(2-methoxypyrimidin-4-yl)-6-(3-trifluoromethylphenyl)-1H-pyrazolo[3,4-b]pyridine; N-[2-[4,6-(diphenyl)-5-(4-pyridyl)pyrazolo[3,4-b]pyridin-2-yl]ethyl]acetamideN-[3-[4,6-bis(4-fluorophenyl)-5-(4-pyridyl)pyrazolo[3,4-b]pyridin-2-yl]propyl]acetamideN-[2-(4,6-diphenyl-5-(4-pyridyl)pyrazolo[3,4-b]pyridin-2-yl)ethyl]-N-(2-hydroxyethyl)acetamideN-[2-[4,6-bis(4-fluorophenyl)-5-(4-pyridyl)pyrazolo[3,4-b]pyridin-2-yl]ethyl]propionamideN-[3-[4,6-bis(4-fluorophenyl)-5-(4-pyridyl)pyrazolo[3,4-b]pyridin-2-yl]propyl]methanesulfonamide5-(2-aminopyrimidin-4-yl)-6-(3-trifluoromethylphenyl)-1ry-pyrazolo[3,4-b]pyridineN-[5-(2-methylsulfanylpyrimidin-4-yl)-6-(3-trifluoromethylphenyl)-1H-pyrazolo[3,4-b]pyridin-3-yl]acetamideN-cyclopropylmethyl-1-[4-[3-benzyloxycarbonylamino-6-(3-trifluoromethylphenyl)-1H-pyrazolo[3,4-b]pyridin-5-yl]pyrimidin-2-yl]amineN-[2-[4,6-bis(4-fluorophenyl)-5-(4-pyridyl)pyrazolo[3,4-b]pyridin-2-yl]ethyl]-2-hydroxyacetamideN-[2-[4,6-bis(4-fluorophenyl)-5-(4-pyridyl)pyrazolo[3,4-b]pyridin-2-yl]ethyl]piperidine-4-carboxamideN-[2-[4,6-bis(4-fluorophenyl)-5-(4-pyridyl)pyrazolo[3,4-b]pyridin-2-yl]

ethyl]-2-(methylamino)acetamideN-[2-[4,6-bis(4-fluorophenyl)-5-(4-pyridyl)pyrazolo[3,4-b]pyridin-2-yl]ethyl]-2-(2-hydroxyethylamino)acetamideN-[2-[4,6-bis(4-fluorophenyl)-5-(4-pyridyl)pyrazolo[3,4-b]pyridin-2-yl]ethyl]nicotinamide4-(4-benzyloxyphenyl)-6-(4-fluorophenyl)-2-methyl-5-4-pyridyl)pyrazolo[3,4-b]pyridine6-(4-fluorophenyl)-5-(2-methylsulfanylpyrimidin-4-yl)-2-methylpyrazolo[3,4-bjpyridine6-(4-fluorophenyl)-2,4-dimethyl-5-(4-pyridyl)pyrazolo[3,4-b]pyridine4-(4-benzyloxyphenyl)-6-(4-fluorophenyl)-2-methyl-5-(2-methylsulfanylpyrimidin-4-yl)pyrazolo[3,4-b]pyridine2-(1-benzylpyrrolidin-2-ylmethyl)-4,6-bis(4-fluorophenyl)-5-(4-pyridyl)pyrazolo[3,4-b]pyridine4-(4-benzyloxyphenyl)-6-(4-fluorophenyl)-2-methyl-5-pyrimidin-4-ylpyrazolo[3,4-b]pyridine6-(4-fluorophenyl)-2-methyl-4-(5-methylfuran-2-yl)-5-(4-pyridyl)pyrazolo[3,4-b]pyridine4-(5-bromofuran-2-yl)-6-(4-fluorophenyl)-2-methyl-5-(4-pyridyl)pyrazolo[3,4-b]pyridine6-(4-fluorophenyl)-2-methyl-4-propyl-5-(4-pyridyl)pyrazolo[3,4-b]pyridine4-(3-benzyloxyphenyl)-6-(4-fluorophenyl)-2-methyl-5-(4-pyridyl)pyrazolo[3,4-b]pyridine6-(4-fluorophenyl)-2-methyl-4-(2-phenylethyl)-5-(4-pyridyl)pyrazolo[3,4-b]pyridine5-(2-chloropyridin-4-yl)-6-(4-fluorophenyl)-2-methylpyrazolo[3,4-b]pyridine4-benzyl-6-(4-fluorophenyl)-2-methyl-5-(4-pyridyl)pyrazolo[3,4-b]pyridine4-[6-(4-fluorophenyl)-2-methyl-5-(4-pyridyl)pyrazolo[3,4-b]pyridin-4-yl]butan-1-ol; 4-[6-(4-fluorophenyl)-2-methyl-5-(4-pyridyl)pyrazolo[3,4-b]pyridin-4-yl]phenolN-[6-(4-fluorophenyl)-5-(2-methylsulfanylpyrimidin-4-yl)-1H-pyrazolo[3,4-b]pyridin-3-yl]acetamideN-[5-[2-[(cyclopropylmethyl)amino]pyrimidin-4-yl]-6-(4-fluorophenyl)-1H-pyrazolo[3,4-b]pyridin-3-yl]acetamide3-[6-(4-fluorophenyl)-4-(2-furyl)-5-(4-pyridyl)pyrazolo[3,4-b]pyridin-2-yl]propan-1-ol2-[4-(4-benzyloxyphenyl)-6-(4-fluorophenyl)-5-(4-pyridyl)pyrazolo[3,4-b]pyridin-2-yl]ethanol3-[4-(4-benzyloxyphenyl)-6-(4-fluorophenyl)-5-(4-pyridyl)pyrazolo[3,4-b]pyridin-2-yl]propan-1-ol3-[6-(4-fluorophenyl)-4-(5-methylfuran-2-yl)-5-(4-pyridyl)pyrazolo[3,4-b]pyridin-2-yl]propan-1-ol3-[4-cyclopropyl-6-(4-fluorophenyl)-5-(4-pyridyl)pyrazolo[3,4-b]pyridin-2-yl]propan-1-ol3-[4-(5-bromothien-2-yl)-6-(4-fluorophenyl)-5-(4-pyridyl)pyrazolo[3,4-b]pyridin-2-yl]propan-1-ol3-[6-(4-fluorophenyl)-4-propyl-5-(4-pyridyl)pyrazolo[3,4-b]-pyridin-2-yl]propan-1-ol3-[4,6-bis(4-fluorophenyl)-5-pyrimidin-4-ylpyrazolo[3,4-b]pyridin-2-yl]propan-1-ol3-[4-(3-benzyloxyphenyl)-6-(4-fluorophenyl)-5-(4-pyridyl)pyrazolo[3,4-b]pyridin-2-yl]propan-1-ol3-[4-benzyl-6-(4-fluorophenyl)-5-(4-pyridyl)pyrazolo[3,4-b]pyridin-2-yl]propan-1-ol(1 S)—N-(1-phenylethyl)-[4-[6-(4-fluorophenyl)-3-methyl-1H-pyrazolo[3,4-b]pyridin-5-yl]pyrimidin-2-yl]amineN-cyclopropylmethyl-[4-[6-(4-fluorophenyl)-3-methyl-1H-pyrazolo[3,4-b]pyridin-5-yl]pyrimidin-2-yl]amine1-[4-[6-(4-fluorophenyl)-2-methylpyrazolo[3,4-b]pyridin-5-yl]pyrimidin-2-ylamino]propan-2-olN-cyclopropylmethyl-[4-[6-phenyl-1H-pyrazolo[3,4-b]pyridin-5-yl]pyrimidin-2-yl]amine2-[4-[6-(4-fluorophenyl)-2-methylpyrazolo[3,4-b]pyridin-5-yl]pyrimidin-2-ylamino]propan-1-ol4-[4-[6-(4-fluorophenyl)-2-methyl-pyrazolo[3,4-b]pyridin-5-yl]pyrimidin-2-ylamino]butan-1-ol (1 S)—N-(1-phenylethyl)-[4-[6-phenyl-1H-pyrazolo[3,4-b]pyridin-5-yl]pyrimidin-2-yl]amineN-(3-methoxypropyl)-[4-[6-(3-trifluoromethylphenyl)-1H-pyrazolo[3,4-b]pyridin-5-yl]pyrimidin-2-yl]amine3-[4-[6-(3-trifluoromethylphenyl)-1H-pyrazolo[3,4-b]pyridin-5-yl]pyrimidin-2-ylamino]propan-1-ol3-[4-[6-(4-fluorophenyl)-2-(3-hydroxypropyl)pyrazolo[3,4-b]pyridin-5-yl]pyrimidin-2-ylamino]propan-1-olN-ethyl-[4-[6-(3-trifluoromethylphenyl)-1H-pyrazolo[3,4-b]pyridin-5-yl]pyrimidin-2-yl]amineN-benzyl-[4-[6-(3-trifluoromethylphenyl)-1H-pyrazolo[3,4-b]pyridin-5-yl]pyrimidin-2-yl]amine4-[5-[2-[(cyclopropylmethyl)amino]pyrimidin-4-yl]-6-(4-fluorophenyl)-2-methylpyrazolo[3,4-b]pyridin-4-yl]phenol4-[6-(4-fluorophenyl)-2-(3-hydroxypropyl)-5-(4-pyridyl)pyrazolo[3,4-b]pyridin-4-yl]phenol4-[6-(4-fluorophenyl)-2-methyl-5-pyrimidin-4-ylpyrazolo[3,4-b]pyridin-4-yl]phenol3-[6-(4-fluorophenyl)-2-(3-hydroxypropyl)-5-(4-pyridyl)pyrazolo[3,4-b]pyridin-4-yl]phenol3-[6-(4-fluorophenyl)-2-methyl-5-(4-pyridyl)pyrazolo[3,4-b]pyridin-4-yl]phenol4,6-bis(4-fluorophenyl)-5-(4-pyridyl)-2-(pyrrolidin-2-ylmethyl)pyrazolo[3,4b]pyridine4-[4-[6-(4-fluorophenyl)-2-methylpyrazolo[3,4-b]pyridin-5-yl]pyridin-2-ylamino]benzenesulfonamideN-[5-[2-[(cyclopropylmethyl)amino]pyrimidin-4-yl]-6-(4-fluorophenyl)-1H-pyrazolo[3,4-b]pyridin-3-yl]acetamide 7-oxide; and N-[6-(4-fluorophenyl)-5-(4-pyridyl)-1H-pyrazolo[3,4-b]pyridin-3-yl]isonicotinamide; or a salt, solvate or prodrug thereof.

Examples of other p38 MAP kinase inhibitors include substituted pyridyls such as those disclosed in US 2003/0139462 A.

Further p38 MAP kinase inhibitors are those disclosed in U.S. Pat. No. 6,610,688 B.

A quinazoline derivative can also function as a p38 MAP kinase inhibitor. Examples of quinazoline derivatives as p38 MAP kinase inhibitors are disclosed in U.S. Pat. Nos. 6,541,477 B, 6,184,226 B, 6,509,363 B and 6,635,644 B.

Aryl ureas and heteroaryl analogues can also function as p38 MAP kinase inhibitors. Examples of the aryl ureas and heteroaryl analogues as p38 MAP kinase inhibitors are disclosed in U.S. Pat. No. 6,344,476 B. WO 99/32110 A describes hetero ring-ureas as p38 MAP kinase inhibitors. WO 99/32463 A describes urea compounds inhibiting p38 kinase. WO 98/52558 A describes urea compounds for p38 kinase inhibition. WO 99/00357 A describes a method for using urea compounds as p38 kinase inhibitors. WO 99/58502 A describes urea compounds as p38 kinase inhibitors.

A substituted imidazole compound and a substituted triazole compound can also function as p38 inhibitors. Such compounds are disclosed in U.S. Pat. Nos. 6,560,871 B and 6,599,910 B respectively.

Specific examples of p38 MAP kinase inhibitors include 2-(4-Chlorophenyl)-4-(fluorophenyl)-5-pyridin-4-yl-1,2-dihydropyrazol-3-one, RWJ-67657 (RW Johnson Pharmaceutical Research Institute); RDP-58 (Sangstat Medical); Scios-469 (talmapimod) (Scios, J&J); MKK3/MKK6 inhibitor (Signal Research Division); SB-210313 analogue, SB-220025 (Aventis), SB-238039, HEP-689, SB-203580 (Leo), SB-239063 (R. W. Johnson), SB-239065, SB-242235 (SmithKline Beecham Pharmaceuticals); VX-702 and VX-745 (Vertex Pharmaceuticals); AMG-548 (Amgen); Astex p38 kinase inhibitor (Bayer); BIRB-796 (Doramapimod) (Boehringer Ingelheim Pharmaceuticals); RO 4402257 (Pamapimod) (Roche, Palo Alto); Celltech p38 MAP kinase inhibitor (CeltechGroup plc.); FR-167653 (Fujisawa Pharmaceutical); SB-681323 (Dilmapimod) (GlaxoSmithKline) and SB-281832 (GlaxoSmithKline plc, Scios); MAP kinase inhibitor of LEO Pharmaceuticals (LEO Pharma A/S); Merck & Co. p38 MAP kinase inhibitor (Merck research Laboratories); SC-040 and SC-XX906 (Monsanto); Novartis adenosine A3 antagonists (Novartis AG); p38 MAP kinase inhibitor (Novartis Pharma AG); CP-64131 (Pfizer); CNI-1493 (Picower Institute for Medical Research); RPR-200765A (Phone-Poulenc Rorer); and Roche p38 MAP kinase inhibitor and Ro-320-1195 (Roche Bioscience), AIK-3, AKP-001 (ASKA Pharma), Antibiotic LL Z1640-2, ARRY-614, ARRY-797, AS-1940477, AVE-9940, AZD-7624, BCT-197, BIRB-1017BS, BMS-582949, CAY10571, CBS-3595, CCT-196969, CCT-241161, CDP-146, CGH 2466, CHR-3620, Chlormethiazole edisylate, CM PD-1, Doramapimod, EO 1428, FY-101C, FX-005, GSK-610677 (GlaxoSmithKline), HE-3286, HSB-13, JX 401, KC-706 (Kemia), KC-706 (ITX-5061) (iTherX Inc.), LEO-15520, LEO-1606, Losmapimod (GlaxoSmithKline), LP-590, LY-30007113, LY2228820, M L 3403, OX-27-NO, NP-202, pexmetinib, PF-03715455 (Pfizer), PH-797804 (Pfizer), PS-540446, ralimetinib, regorafenib, RO-3201195, RWJ 67657, RWJ-67657, SB 202190 (Leo), SB 203580 (Pfizer), SB 203580 hydrochloride (Pfizer), SB202190, SB202190 hydrochloride (Roche), SB-681323 (Tanabe Seiyaku), SB-856553, SC-80036, SCD-282, SCIO-323, SCIO-469, SD-06, semapimod, SKF 86002, SX 011, SYD-003, TA-5493, TAK 715 (Takeda Pharma), Tie2 Kinase Inhibitor (Tanabe Pharma), TOP-1210, TOP-1630, UR-13870 (Bristol-Myers Squibb), UR-13870 (Palau Pharma) and VGX-1027.

In some embodiments, the p38 MAP kinase inhibitor may be selected from 8-(2,6-difluorophenyl)-2-(1,3-dihydroxypropan-2-ylamino)-4-(4-fluoro-2-methylphenyl)pyrido[2,3-d]pyrimidin-7-one (Dilmapimod), GSK-610677 and 6-[5-(cyclopropylcarbamoyl)-3-fluoro-2-methylphenyl]-N-(2,2-dimethylpropyl)pyridine-3-carboxamide (Losmapimod).

In one embodiment, the p38 MAP kinase inhibitor may be 5-[(2-chloro-6-fluorophenyl)acetylamino]-3-(4-fluorophenyl)-4-(4-pyrimidinyl)isoxazole (AKP-001).

In another embodiment, the p38 MAP kinase inhibitor may be KC-706.

In another embodiment, the p38 MAP kinase inhibitor may be (1-[5-tert-butyl-2-(3-chloro-4-hydroxyphenyl)pyrazol-3-yl]-3-[[2-[[3-[2-(2-hydroxyethylsulfanyl)phenyl]-[1,2,4]triazolo[4,3-a]pyridin-6-yl]sulfanyl]phenyl]methyl]urea) (PF-03715455).

In another embodiment, the p38 MAP kinase inhibitor may be (3-[3-bromo-4-[(2,4-difluorophenyl)methoxy]-6-methyl-2-oxopyridin-1-yl]-N,4-dimethylbenzamide) (PH-797804).

In another embodiment, the p38 MAP kinase inhibitor may be 2-methoxy-1-{4-[(4-{3-[5-(tert-butyl)-2-(p-tolyl)-2H-pyrazol-3-yl]ureido}-1-naphthyloxy)methyl]-2-pyridylamino}-1-ethanone (RV-568):

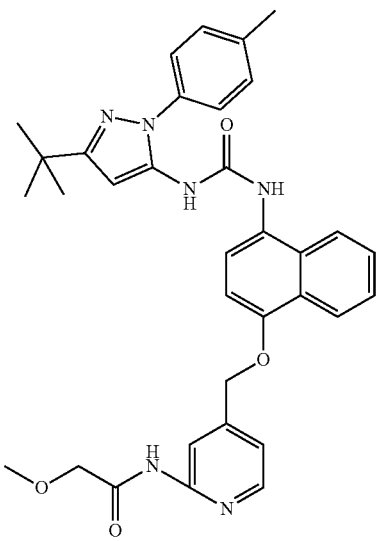

Alternatively, the p38 MAP kinase inhibitor may be 2-methoxy-1-[4-(4-{3-[5-(tert-butyl)-2-(p-tolyl)-2H-pyrazol-3-yl]ureido}-1-naphthyloxy)-2-pyridylamino]-1-ethanone:

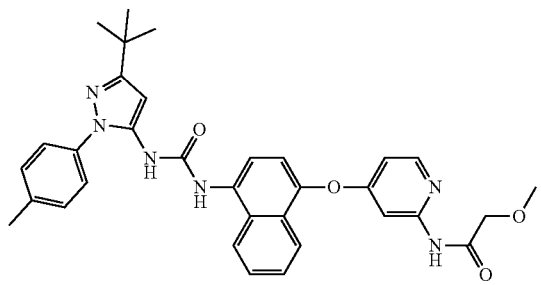

In another embodiment, the p38 MAP kinase inhibitor may be 4,6-bis(p-fluorophenyl)-2-methyl-5-(4-pyridyl)-1,2,7-triaza-2H-indene (UR-13870):

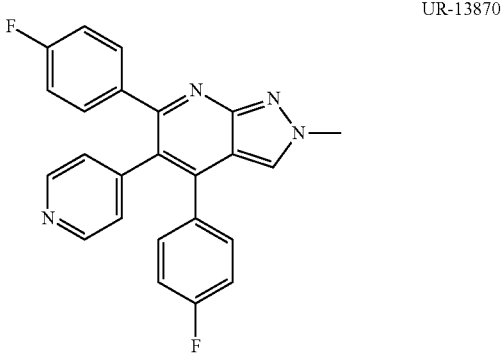 [SMILES: Cn1cc2c(-c3ccc(F)cc3)c(-c3ccncc3)c(-c3ccc(F)cc3)nc2n1]

In another embodiment, the p38 MAP kinase inhibitor may be RV-7031.

The present invention is not limited to the specific p38 MAPK inhibitors recited above. A candidate compound may be tested for p38 MAPK inhibitory activity using a suitable enzyme inhibition assay of the kind known to those skilled in the art. For example, the enzyme inhibitory activity of a compound may be determined by fluorescence resonance energy transfer (FRET), as described in the examples below. Other suitable assays are described in Lee, et al., 2000.

The use of a p38 MAP kinase inhibitor in accordance with the present invention aims to attenuate the inflammatory response in a patient with severe influenza, rather than ablate it, with the objective of blunting the damaging effects of the out-of-control inflammation, whilst preserving its protective and disease pro-resolution effects. Total ablation of inflammation would be likely to promote mortality in severe influenza, whereas attenuation of this explosive process should provide protection against the damaging effects caused by excess inflammatory responses whilst preserving the host's essential innate defence activities. The present invention therefore aims to "re-balance the system" rather than knock out components in their entirety.

The p38 MAPK inhibitor may be administered systemically or non-systemically, such as orally, or topically, including epidermally, bucally, intranasally or via inhalation (aerosol), or both intranasally and via inhalation or parenterally (e.g. intravenously, subcutaneously) or in combination topically and parenterally.

As used herein "topically" includes non-systemic administration. This includes the application of a compound externally to the epidermis or the buccal cavity and/or the instillation of such a compound into the ear, eye and nose.

As used herein "systemic administration" refers to oral, intravenous, intraperitoneal and intramuscular administration, subcutaneous intranasal, intra-rectal or intravaginal.

It will be recognized by those skilled in the art that the optimal quantity and spacing of individual dosages of a p38 MAPK inhibitor will be determined by the nature and extent of the condition being treated, the form, route and site of administration, and the particular patient being treated, and that such optimums can be determined by conventional techniques. It will also be appreciated by one of skill in the art that the optimal course of treatment, i.e. the number of doses of a p38 MAPK inhibitor given per day for a defined number of days, can be ascertained by those skilled in the art using conventional course of treatment determination tests. However, in view of its key signalling role, targeting p38 MAP kinase may result in unwanted side effects. In order to minimise any such side effects, the p38 MAP kinase inhibitor may be administered to a patient in accordance with the present invention for a maximum period of 1-5 days, preferably 1-3 days. In some embodiments, the p38 MAP kinase inhibitor may be administered for just one or two days. Once-a-day treatment may also be preferred to minimise any deleterious side effects.

In yet another aspect of the present invention there is provided a pharmaceutical composition for use in the treatment or prevention of severe influenza in a human patient, the composition comprising a p38 MAPK inhibitor, optionally in combination with one or more pharmaceutically acceptable diluents or carriers. Diluents and carriers may include those suitable for parenteral, oral, topical, mucosal and rectal administration.

The pharmaceutical composition of the invention may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The composition may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). A formulation for parenteral administration may contain as excipients sterile water or saline, alkylene glycols such as propylene glycol, polyalkylene glycols such as polyethylene glycol, oils of vegetable origin, hydrogenated naphthalenes and the like. A formulation for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

A composition suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. A liquid composition may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). A liquid composition may be encapsulated in, for example, gelatin to provide a unit dosage form.

A solid oral dosage form may include tablets, two-piece hard shell capsules and soft elastic gelatin (SEG) capsules. A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material may comprise a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

In some embodiments, composition of the invention may be administered topically to the lung. In some embodiments, therefore the composition of the invention may comprise a p38 MAPK inhibitor optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane, dichlorotetrafluoromethane, and dichlorodifluoromethane. Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a pressured metered dose inhaler (pMDI) or a dry-powder formulation. A dry powder formulation will contain the p38 MAPK inhibitor in finely divided form, typically with a mass mean diameter (MMAD) of 1-10 microns. The formulation will typically contain a topically acceptable diluent such as lactose, usually of large particle size e.g. a mass mean diameter (MMAD) of 100 vim or more. Example dry powder delivery systems include SPINHALER, DISKHALER, TURBOHALER, DISKUS and CLICKHALER.

BRIEF DESCRIPTION OF THE DRAWINGS

FIG. 1 illustrates the identification of signalling pathways.

FIG. 2 illustrates the mapping the activity of genes in IL-1, TNFα and IL-6 stimulated pathways. These cytokines are produced by influenza virus infected cells and found to be increased in the blood of people infected with influenza, particularly those hospitalised with severe influenza. The hatched lines indicate gene expression levels with lines sloping from top right to bottom left indicating upregulation (e.g. TNF-α), and lines sloping from top left to bottom right (e.g. LBP) indicating down-regulation; genes that are both upregulated and down-regulated are indicated by cross-hatching. The line spacing represents the intensity of up- or down-regulation, with more densely packed lines indicating greater activity. The maps were generated using IPA. A "route" through a pathway is defined as a single contiguous connection of proteins that extend from the plasma membrane through to the nucleus.

FIG. 3 shows an example of scoring a route through the IL-6 pathway of FIG. 2.

FIG. 4 shows three key cell types involved in the pathology of severe influenza.

FIG. 5 is a schematic of influenza 'soup' production and electrogenerated chemiluminescence analysis in human epithelial cells. Infected cell "soups" contain key cytokines found in clinical samples.

FIG. 6 shows Western blotting of phosphorylated P38 and HSP27 in response to viral soup application and effects of P38 inhibition in epithelial cells. Electrogenerated chemiluminescence analysis of inflammatory cytokine production in response to viral soup application, and effects of P38 inhibition in epithelial cells.

FIG. 7 shows Western blotting of phosphorylated HSP27 in response to viral soup application and effects of P38 inhibition in endothelial cells. Electrogenerated chemiluminescence analysis of inflammatory cytokine production in response to viral soup application, and effects of P38 inhibition in endothelial cells.

FIG. 8 shows Western blotting of phosphorylated HSP27 in response to viral soup application and effects of P38 inhibition in immune cells. Electrogenerated chemiluminescence analysis of inflammatory cytokine production in response to viral soup application, and effects of P38 inhibition in immune cells. Cell viability of immune cells in response to increasing concentrations of P38 inhibitor.

FIG. 9 shows electrogenerated chemiluminescence analysis of inflammatory cytokine production in response to LPS, CD-3 and viral soup application. Effects of P38 inhibition on viral soup induced inflammatory cytokine in immune cells.

FIG. 10 shows the effects of p38 and MEK inhibitors on IP10 production by HUVECs stimulated with 70% HBEC viral soup. Secreted cytokine levels were assayed by electrogenerated chemiluminescence. Statistical significance was calculated using one-way ANOVA with Dunnett's multiple comparison post hoc test.

FIG. 11 shows compound effects on IL-1b production from immune cells. Each point on the dot plot represents an individual experiment. Statistical significance was calculated using one-way ANOVA with Dunnett's multiple comparison post hoc test.

FIG. 12. shows compound effects on TNFa production from immune cells. Each point on the dot plot represents an individual experiment. Statistical significance was calculated using one-way ANOVA with Dunnett's multiple comparison post hoc test.

FIG. 13 shows compound effects on IP10 production from endothelial cells. Each point on the dot plot represents an individual experiment. Statistical significance was calculated using one-way ANOVA with Dunnett's multiple comparison post hoc test.

FIG. 14 shows compound effects on IL8 production from endothelial cells. Each point on the dot plot represents an individual experiment. Statistical significance was calculated using one-way ANOVA with Dunnett's multiple comparison post hoc test.

FIG. 15 shows the cytokine levels in 28 healthy volunteers infected with influenza virus (samples collected at Day −1 to Day 28, hollow dots) and 30 individuals hospitalised with severe influenza (stippled dots). Blood samples from the severe patients were collected between 24 and 72 hours after admission to hospital. The statistical significance of differences in cytokine levels between the infected healthy volunteers (D2 and D3) and the hospitalised patients (influenza A or B) was calculated using the Mann-Whitney U test.

EXAMPLES

Example 1: Identification of p38 MAPK by Transcriptomic Analysis

Bioinformatics analysis of transcriptomic data from blood samples collected from human volunteers and patients infected with influenza was used to map the signalling pathways activated in the human host response to influenza infection in both uncomplicated (mild and moderate) and severe influenza (see PHE Guidance on Use of Anti-Viral Agents for the Treatment and Prophylaxis of Seasonal Influenza (2015-16), version 6.0, September 2015). Human viral challenge studies were carried out and transcriptomic data from those studies were used for mapping the former, while transcriptomic data from a field-based sampling study (Hoang, L. T. et al., 2014) were used for mapping the latter. Comparison of signalling pathways identified by comparing both datasets enabled the identification of signalling pathways that are very active in severe influenza versus mild and moderate influenza. Further analysis of individual pathway components identified p38 MAPK as a key "node" in a number of these active pathways.

Healthy human volunteers were intranasally challenged with influenza A/Wisconsin/67/2005 (H3N2) (Zaas, A. K. et al., Gene expression signatures diagnose influenza and other symptomatic respiratory viral infection in humans, Cell Host Microbe, 2009; 17:207-217 and Davenport, E. E. et al., Transcriptomic profiling facilitates classification of response to influenza challenge, J. Mol. Med., 2015; 93:105-114) or with influenza A/Perth/16/2009 (H3N2) (internal study, not published). PAXgene™ samples of whole blood were collected from the volunteers at various time points for subsequent transcriptome analysis. Methods for influenza A/Wisconsin/67/2005 (H3N2) viral challenge, case definitions, sample collection, RNA purification and microarray analysis are as detailed in Zaas et al., 2009 and Davenport et al., 2015. Methods for influenza A/Perth/16/2009 (H3N2) viral challenge, case definitions and sample collection were as described for the Wisconsin strain except RNA purification and microarray analysis using Affymetrix HGU133 Plus 2.0 arrays were performed by Almac. (Information about Almac can be retrieved from the Internet Archive Wayback Machine, at web*archive*org, from the archive of 17 Mar. 2016 of the site at domain www*almacgroup*com.) Methods for recruiting patients with severe influenza, blood sample collection, RNA purification and microarray analysis are as detailed in Hoang et al., 2014.

Microarray data files for the Zaas et al., 2009, Davenport et al., 2015 and Hoang et al., 2014 studies were downloaded from the Gene Expression Omnibus (GEO) database using the accession numbers GSE52428, GSE61754 and GSE61821, respectively. Microarray data (.CEL) files for the unpublished study were downloaded from Almac and stored locally for bioinformatics analysis. All four transcriptomic datasets were processed and analysed using the R (version 3.0.2.) integrated suite of software facilities for data manipulation, calculation and graphical display. Quality assessment of raw microarray data was performed using statistical methods standard in the art (e.g. Heber, S. and Sick, B., Quality assessment of affymetrix genechip data, Omics, 2006; 10:358-368). Affymetrix datasets were normalised using the Robust Multi-array Average (RMA) method and Illumina datasets were normalised using the Lumi package. Both packages were executed in the R environment. To facilitate annotation of probe-sets and gene names, Affymetrix chip definition files (version 17.1.0) were downloaded from the BrainArray website, and Illumina chip definition files (illuminaHumanv4.db) were downloaded from the Bioconductor website.

(Information about GEO can be retrieved from the Internet Archive Wayback Machine, at web*archive*org, from the archive of 22 Jun. 2016 of the site at domain www*ncbi*nlm*nih*gov, along the path /geo. Information about the R suite can be retrieved from the Wayback Machine from the archive of 23 Jun. 2016 of the site at domain www*R-project*org. Information about normalising affymetrix datasets using the RMA method can be retrieved from the site at domain www*bioconductor*org, along the path /packages/3.3/bioc/manuals/affy/man/affy.pdf. Information about normalising Illumina datasets using the Lumi package can be retrieved from the site at www*bioconductor*org, along the path /packages/3.3/bioc/manuals/lumi/man/lumi.pdf. Relevant information from the BrainArray website can be retrieved from the Wayback Machine from the archive of 23 Jun. 2016 of the site at brainarray*mbni*med*umich*edu, along the path /Brainarray/Database/CustomCDF/17.1.0/ensg.asp. Relevant information about the Illumina chip definition files from the Bioconductor website can be retrieved from the Wayback Machine from the archive of 9 Dec. 2015 of the site at bioconductor*org, along the path packages/release/data/annotation/html/illuminaHumanv4.db.html.)

The latter files were used with microarray data from Davenport et al., 2015 and Hoang et al., 2014.

Normalised Zaas et al., 2009, Davenport et al., 2015 and Perth datasets were individually merged with the Hoang et al., 2014 dataset using the COMBAT module in the InSilicoMerging package in Bioconductor. Differential gene expression analysis on merged data sets was carried out using the limma package in R (Information about the COMBAT module can be retrieved from the Internet Archive Wayback Machine, at web*archive*org, from the archive of 5 Sep. 2015 of the site at domain www*bioconductor*org, along the path /packages/release/bioc/html/inSilicoMerging.html. Information about the limma package can be retrieved from the site at www*bioconductor*org, along the path /packages/3.3/bioc/vignettes/limma/inst/doc/usersguide.pdf.) For pairwise comparisons only data from infected volunteers in the Zaas et al., 2009, Davenport et al., 2015 and Perth datasets were used, equating to 11, 14 and 5 subjects, respectively. From the Hoang et al., 2014 dataset only data for the three H3N2-infected severe influenza patients in the data set were used. For each merged data set two pairwise comparisons were performed to identify genes that were upregulated relative to baseline levels after infection with virus and then further upregulated in the severe patient samples:

Perth: day −1 vs day 3 and; day 3 vs Hoang et al., 2014 severe.

Zaas et al., 2009: day −1 vs 60 hours and; 60 hours vs Hoang et al., 2014 severe.

Davenport et al., 2015: day 0 vs 48 hours and; 48 hours vs Hoang et al., 2014 severe.

To maximise the number of upregulated genes that could be mapped to pathways, all genes showing fold-changes >0 were identified. Each of the 6 resulting gene lists were analysed through the use of QIAGEN's Ingenuity® Pathway Analysis (IPA®, QIAGEN Redwood City; information about IPA® can be retrieved from the Internet Archive Wayback Machine, at web*archive*org, from the archive of 21 Oct. 2013 of the site at domain www*ingenuity*com). This resulted in the identification of 650 signalling pathways which were reduced to 353 after the removal of 297 metabolic pathways. FIG. 1 summarises this process.

Figure 2:
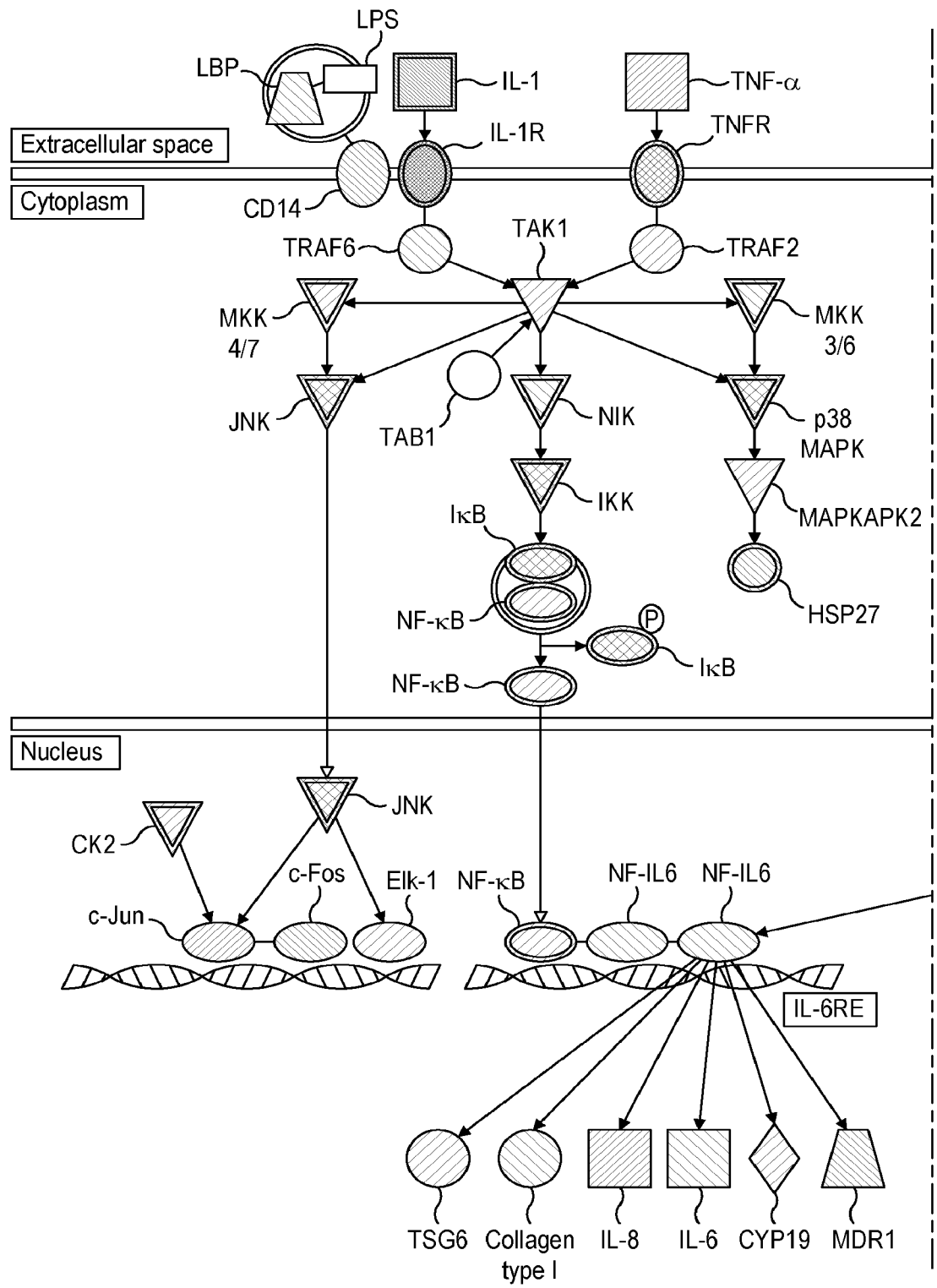
Figure 2:
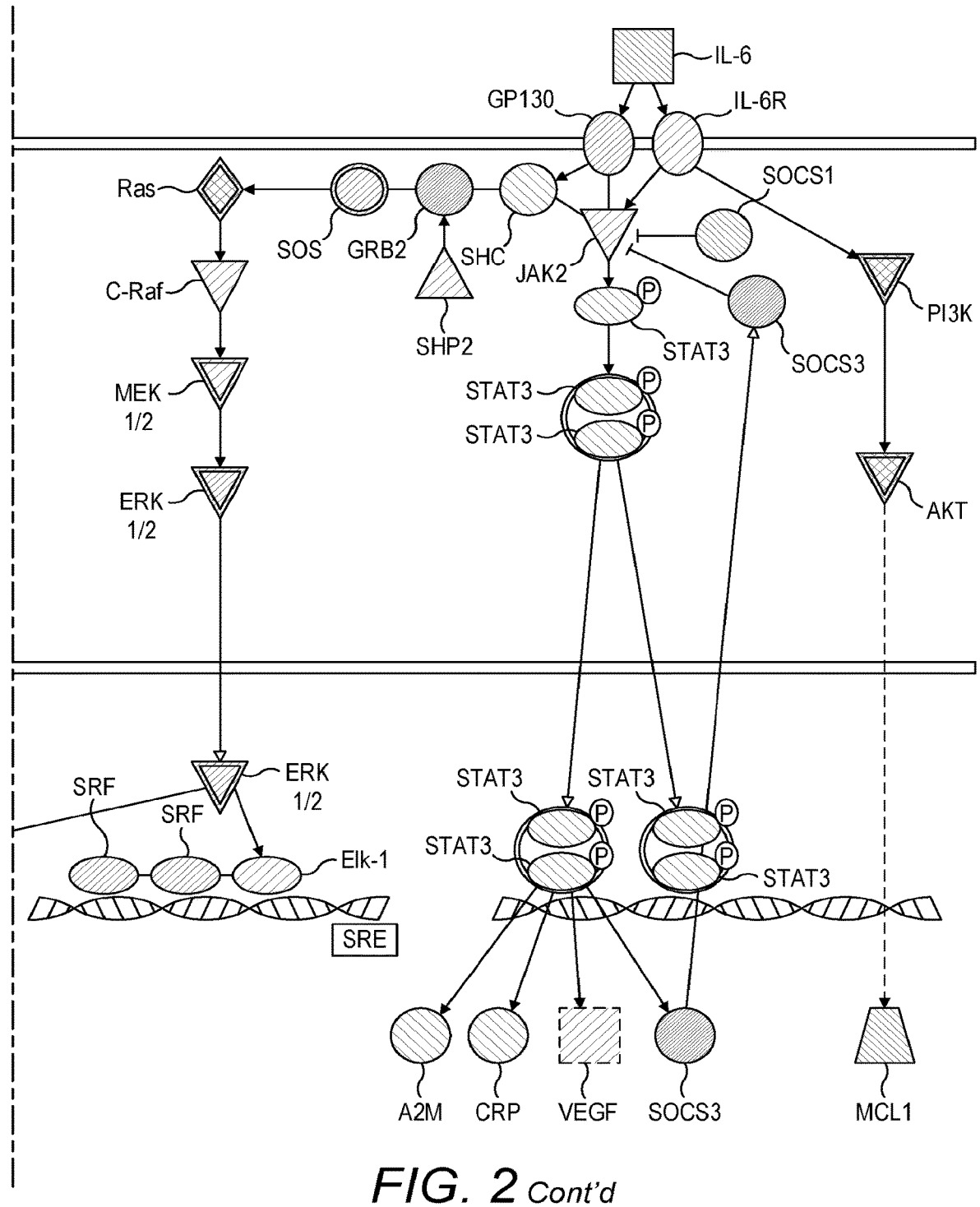

In order to interrogate the relevance of each of these signalling pathways to the pathogenesis of severe influenza, a manual scoring approach was devised to identify very active "routes" within these pathways in the complicated versus the "uncomplicated" influenza datasets. In this context "routes" are defined as contiguous connections of proteins in a canonical pathway that extend from the plasma membrane through to the nucleus. As a result, a canonical pathway may have a number of different routes through it. Using this scoring approach, routes within IPA canonical pathways were mapped directionally from the plasma membrane to the nucleus and the 'overlay' function in IPA was used to show gene activity. To illustrate this process an example of three pathways identified using this method is shown in FIG. 2.

Figure 3:
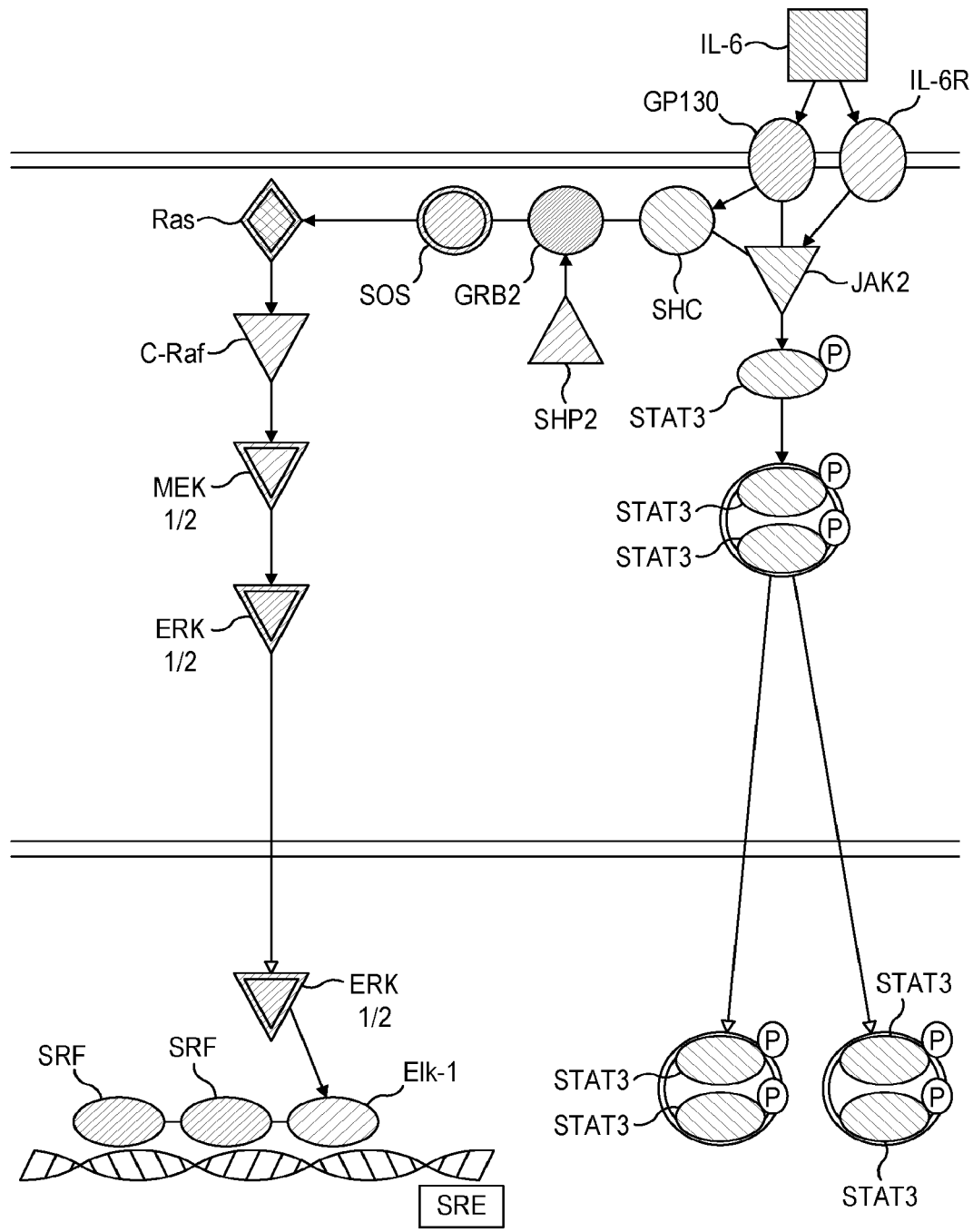
Figure 4:
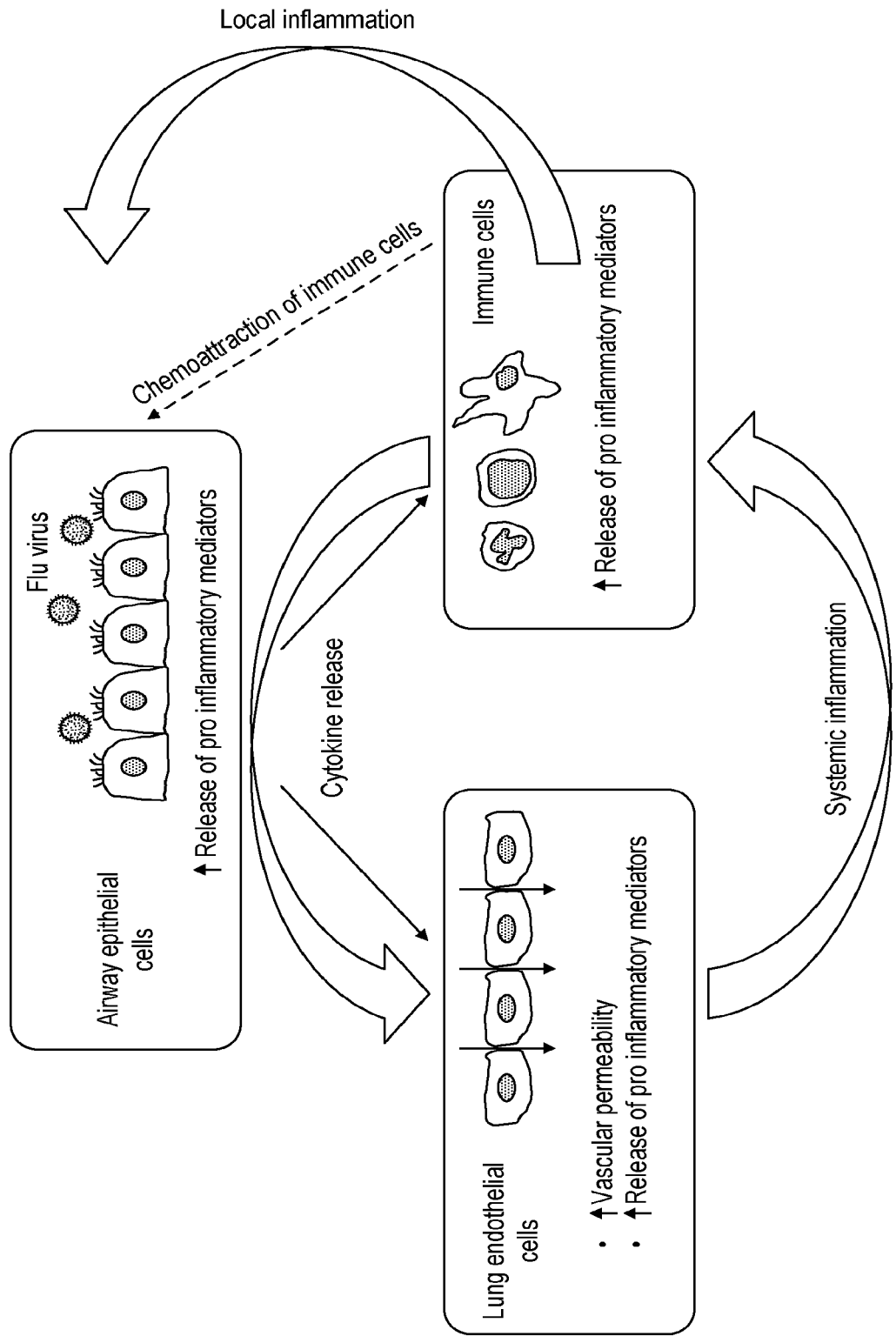

Individual routes in the identified 353 pathways were manually scored for gene activity as exemplified in FIG. 3 for a route through the IL-1 canonical pathway in which:

TABLE 1

| Pathway | Route | Nodes Up-regulated | Nodes not up-regulated |
|---|---|---|---|
| IL-6 signalling | IL6R + GP130-SHC-GRB2-SOS-Ras-cRAF-MEK-ERK-ELK + SRF | 81% | SHC-Ras |

In all, 491 routes showing ≥75% up-regulated nodes were identified (exemplified in Table 2 below). Of these, 95 routes containing >3 nodes were identified in which 100% of all the nodes in the route were upregulated in the Hoang et al., 2014 severe influenza dataset versus baseline (D-1 or D0) in the Zaas et al., 2009, Davenport et al., 2015 and Perth datasets (Table 3). Twenty-four of these 95 routes were shown to be ≥75% upregulated compared with pathways derived from the mild and moderate H3N2 and H1N1 influenza datasets from Hoang et al., 2014 (H3N2 and H1N1—mild and moderate) and Zaas et al., 2009 (H1N1—D-1 and 60 h; Table 4).

Inspection of the 95 routes highlighted a number of potentially targetable nodes from which p38MAPK was chosen because of its well characterised role in inflammation and the availability of high quality clinically tested small molecule inhibitors for use in in vitro and ex vivo studies.

TABLE 2

An example of route scoring analysis.

| Pathway | Route | Nodes | Nodes↑ (%) | ↓Nodes |
|---|---|---|---|---|
| NFKB | growth factor receptors-RAS-RAF-MEKK1-IKKa-NFKB2-RELB-lymphogenesis | 10 | 92 | IKKB |
| NFKB | IL-1R/TLR-MYD88-TYRAP-IRAP-IRAK-TRAF6-TAK1-IKKa-IKBP65-P65NFKB-P65NFKB-inflammation | 8 | 93 | IKKB |
| Role of JAK1 and JAK3 in cytokine signalling | IL21Ralpha/IL2Rgamma-JAK3-STAT1/3/5* | 4 | 100 | |
| PI3K-AKT signalling RTK | Integrin-PINCH-ILK-PI3K-PP2A-AKT-CRAF-MEK1/2-ERK1/2-P70S6K-cell growth | 9 | 89 | |
| PI3K-AKT signalling RTK | Integrin-PINCH-ILK-PI3K-PP2A-AKT-CRAF-MEK1/2-ERK 1/2-P70S6K-cell growth | 9 | 89 | |
| PI3K-AKT signalling integrin | Integrin-PINCH-ILK-PI3K-PP2A-AKT-CRAF-MEK1/2-ERK1/2-P70S6K-cell growth | 9 | 78 | |
| NFKB | TNF-TANK-TRAF-FADD-RIP-MAP3K3-IKKa-IKBP65-P65NFKB-inflammation | 7 | 87.5 | TNF-R/IKKB |
| CNTF signalling | (CNTFR-LIFR-GP130)-JAK1/2-SHP2-GRB2-SOS-RAS-CRAF-MEK1/2-ERK1/2-P()RSK-gene expression | 10 | 90 | SHP2 |
| CNTF signalling | (CNTFR-LIFR-GP130)-TYK2-STAT1/3-gene expression | 3 | 100 | |
| role of JAK in IL-6 type cytokine signalling | (GP130-OSMR)-intermediate signalling-ERK1/2-p38MAPK-JNK-signalling | 4 | 100 | |
| role of JAK in IL-6 type cytokine signalling | (GP130-OSMR)-JAK2-STAT1/3/5-gene expression | 3 | 100 | |
| role of JAK in IL-6 type cytokine signalling | (GP130-OSMR)-STAT1/3-gene expression | 2 | 100 | |
| HER-2 signalling in breast cancer | (HER1/HER2)-GRB2-SOS-RAS-(CYCLIND1-CDK6-CYCLINE-p27KIP1)-cell cycle progression and proliferation | 5 | 80 | HER1-HER2 |
| HER-2 signalling in breast cancer | (HER1/HER2)-PI3K-AKT-CYCLIND1-cell cycle progression | 4 | 75 | HER1-HER2 |
| role of JAk1, JAK2 and TYK2 in interferon signalling | (IFNAR1-IFNAR2)-TYK2-STAT2-STAT1-gene expression | 4 | 100 | |
| IL-9 signalling | (IL-9R-IL2R)-JAK3-IRS1/2-PI3K-PI3ksignalling | 5 | 100 | |

TABLE 3

Ninety-five routes containing 100% upregulated nodes in the Hoang et al., 2014 severe influenza dataset versus the Zaas et al., 2009, Davenport et al., 2015 and Perth baseline datasets.

| Pathway | Route | Number of Nodes |
|---|---|---|
| Acute myeloid leukemia signalling | FLT3-GRB2-SOS-RAS-RAF-MEK-ERK1/2-cell proliferation | 7 |
| Gaq signalling | GqR-Ga/b/y-PYK2-PI3K-AKT-IKK-NFkB* | 7 |
| p38 MAPK signalling | TNFR/fas-TRADD/FAD-TRAF2-Ask1-MKK4-P38MAKa-CHOP-transcription | 7 |
| p38 MAPK signalling | TNFR/fas-TRADD/FAD-TRAF2-Ask1-MKK4-P38MAKa-ELK1-transcription | 7 |
| p38 MAPK signalling | TNFR/fas-TRADD/FAD-TRAF2-Ask1-MKK4-P38MAPKa-MEF2 | 7 |
| SAPK/JNK signalling | TRADD/RIP/FADD-TRAF2-GCKs-MEKK1-MKK4/7-JNK-ELK-1* | 7 |
| Sertoli cell sertoli cell junction signalling | CLDN-ZO2-factin-actinin alpha-tubulin-KEAP1-Myo7a-junction dynamics | 7 |
| HIF1a signalling | RTK-PI3K-AKT-HIF1a-ARNT-ET1-vascular tone* | 6 |
| HIF1a signalling | RIK-PI3K-AKT-HIF1a-ARM-MMPs-ECM regulation* | 6 |
| IL6 signalling | TNFR-TRAF2-TAK1-MKK4/7-JNK-ELK1* | 6 |
| Protein Kinase A signalling | PKAr/PKAc-RAP1-BRAF-MEK1/2-ERK1/2-ELK1* | 6 |
| SAPK/JNK signalling | TRADD/RIP/FADD-TRAF2-ASK1-MKK4/7-JNK-ELK-1* | 6 |

TABLE 3-continued

Ninety-five routes containing 100% upregulated nodes in the Hoang et al., 2014 severe influenza dataset versus the Zaas et al., 2009, Davenport et al., 2015 and Perth baseline datasets.

| Pathway | Route | Number of Nodes |
|---|---|---|
| ERK5 signalling | SRC-MEKK2/3-MEK5-ERK5-SAP1* | 5 |
| Glucocorticoid Receptor signalling | CYTOKINE RECEPTOR-TRAF2-TAK1-MKK4/7-P38MAPK-STABILIZATION OF MRNA, TRANSLATION* | 5 |
| Growth Hormone signalling | GHR-JAK2-ERK1/2-CEBPA* | 5 |
| Growth Hormone signalling | GHR-JAK2-ERK1/2-P90RSK-SRF/ELK1* | 5 |
| HIF1a signalling | RTK-PI3K-AKT-HIF1a-ARNT-GLUT* | 5 |
| HIF1a signalling | RTK-PI3K-AKT-HIF1a-ARNT-VEGF* | 5 |
| IL-22 signalling | IL22R1/2-TYK2-STAT1/3/5-SOCS3* | 5 |
| IL-8 | CXCR1/2-PI3K-Akt-AP1-IntegrinAlphavBeta3 (Chemotaxis) | 5 |
| IL-8 | CXCR1/2-Ras-Raf-MEK1/2-ERK1/2-(Neutrophil Degranulation) | 5 |
| leptin sigalling in obesity | LEPR-JAK2-STAT3-(SOCS3-POMC)-aMSH-anorexia | 5 |
| Paxillin signalling | Integrina/b-FAK-GRB2-SOS-Ras-ERK/MAPK* | 5 |
| Role of RIG like receptors in antiviral innate immunity | dsRNA-RIG1-IPS1-rRAF3-rBK1-IRF7-(IFNa-MDA5/LGP2/R1G1)* | 5 |
| Role of RIG like receptors in antiviral innate immunity | MDA5-IPS1-TRAF3-TBK1-IRF7-(IFNa-MDA5/LGP2/RIG1)* | 5 |
| Role of RIG like receptors in antiviral innate immunity | TRIM25-RIG1-IPS1-TRAF3-IRF7-(IFNa-MDA5/LGP2/RIG1)* | 5 |
| CD40 signalling | CD40-JAK3-STAT3-ICAM1* | 4 |
| ceramide signalling | EDG-SPHK-NFKB-AP1-activation of inflammatory genes | 4 |
| ceramide signalling | SMPD-(ceramide)-PI3K-AKT-apoptosis * | 4 |
| Eicosanoid signalling | PLA2-ALOX5-LTA4h-LTB4R-chemotaxis/proliferation/allergic asthma/angiogenesis/ | 4 |
| G alpha I signalling | GiCOUPLED RECEPTOR-Galphai/Gbcta/Ggamma-SRC-STAT3* | 4 |
| Germ Cell-Sertoli Cell Junction signalling | TGFbetaR-RAS-MEK1/2-ERK1/2-actin depolymerisation* | 4 |
| GM-CSF signalling | GMCSFRA-HCK-PI3K-AKT-cell survival/cell proliferation* | 4 |
| GM-CSF signalling | GMCSFRA-JAK2-STAT3-(BCLXL-CYCLIND1)* | 4 |
| G-Protein Coupled Receptor signalling | Gicoupled receptor-GALPHAi/0-SRC-STAT3 * | 4 |
| IGF-1 signalling | IGF1R-JAK1/2-STAT3-SOCS3* | 4 |
| IL-8 | CXCR1/2-JNK-NFkB-ICAM-1 | 4 |
| IL-8 | CXCR1/2-PI3K-MEK1/2-ERK1/2-(Neutrophil Degranulation) | 4 |
| IL-8 | CXCR1/2-Rho-NFkB-ICAM-1 | 4 |
| JAK/STAT | cytokine receptor-JAK-STAT-(CFOS-IL6-SOCS-BCLXL)* | 4 |
| MSP-RON signalling pathway | RON-PI3K-PKC zeta-F-ACTIN-phagocytic activity in macrophages* | 4 |
| PI3K signalling in B Lymphocytes | IL4R-IRS-P85/PI3K-P110/PI3K-NFKB | 4 |
| PPARα/RXRα Activation | ADIPOR-AMPK-P38MAPK-PPARalpha | 4 |
| Production of nitric oxide and ROS in macrophages | TLR2/4-PI3K-AKT-NFKB-Inos | 4 |
| Production of nitric oxide and ROS in macrophages | TLR2/4-MKK4/-JNK-AP1 | 4 |
| RAR activation | IL-3Ra/b-JAK2-STAT5-RAR/RXR* | 4 |
| Role of MAPK signalling in the Pathogenesis of Influenza | ASK-1-MKK4/7-JNK-CASP3-APOPTOSIS | 4 |
| Role of RIG like receptors in antiviral innate immunity | dsRNA-R1G1-IPS1-TRAF3-IRF7-(IFNa-MDA5/LGP2/RIG1)* | 4 |
| Role of RIG like receptors in antiviral innate immunity | MDA5-IPS1-TRAF3-IRF7-(IFNa-MDA5/LGP2/RIG1)* | 4 |
| signalling by Rho Family GTPases | Integrin-ARHGEF-RHO-FAK-cytoskeletal reorganisation* | 4 |
| signalling by Rho Family GTPases | Integrin-ARHGEF-RHO-PKNI-cell trafficking* | 4 |
| Sphingosine-1-phosphate signalling | SIPR(2/3/4)-GAI-PI3K-AKT-CELL SURVIVAL* | 4 |
| Tec Kinase signalling | Integrin-FAK-TEC KINASE-(FAK, PKC, PAK, VAV, FACTIN, RHOGTPASE, NFKB, JNK, STAT-TFII-1*) | 4 |
| Tec Kinase signalling | TCR-SRC-TEC KINASE-(FAK, PKC, PAK, VAV, FACTIN, RHOGTPASE, NFKB, JNK, STAT-TFII-1*) | 4 |

TABLE 3-continued

Ninety-five routes containing 100% upregulated nodes in the Hoang et al., 2014 severe influenza dataset versus the Zaas et al., 2009, Davenport et al., 2015 and Perth baseline datasets.

| Pathway | Route | Number of Nodes |
|---|---|---|
| Acute myeloid leukemia signalling | FLT3-STAT3/5-PIM1-regulates apoptosis | 3 |
| Antioxidant action of vitamin C | CSF2Ralpha/beta-JAK2-STAT5-gene expression* | 3 |
| CNTF signalling | (CNTFR-LIFR-GP130)-TYK2-STAT1/3-gene expression* | 3 |
| Dendritic Cell Maturation | LTbctaR-IKK-RELB/NFKB-cross presentation | 3 |
| EPHRIN RECEPTOR signalling | EPHA-JAK2-STAT3-CELL PROLIFERATION* | 3 |
| EPHRIN RECEPTOR signalling | EPHB-PI3KG-AKT-CELL MIGRATION, CELL PROLIFERATION | 3 |
| EPHRIN RECEPTOR signalling | INTEGRIN-MEK1/2-ERK1/2-AXON GUIDANCE,CELL PROLIFERATION* | 3 |
| FcyRIIB signalling in B lymphocytes | FCyR-BTK-JNK-apoptosis* | 3 |
| Glucocorticoid Receptor signalling | CYTOKINE RECEPTOR-JAK2-STAT1* | 3 |
| Glucocorticoid Receptor signalling | CYTOKINE RECEPTOR-JAK3-STAT3/5* | 3 |
| GNRH signalling | GnRHR-Gai-NfkB | 3 |
| IL-12 signalling and Production in Macrophages | TLR4-p38/MAPK-IL12 | 3 |
| IL-3 signalling | IL3Ralpha/beta-JAK1/2-STAT1/3/5/6-gene expression* | 3 |
| IL6 signalling | GP130 (IL6R)-JAK2-STAT3-gene expression* | 3 |
| IL-8 | CXCR1-PLD-NADPH oxidase-(Superoxide production-Respiratory Burst) | 3 |
| IL-8 | CXCR1-G Protein alpha/beta/gamma-PI3Ky-(Chemotaxis-Respiratory Burst)* | 3 |
| LPS stimulated MAPK signalling | TLR4-IKK-IKB-NFKB-gene expression* | 3 |
| mTOR signalling | Nutrients-RHEB-mTORc2-AKT-PI3K/AKT signalling* | 3 |
| mTOR signalling | Nutrients-RHEB-mTORc2-AKT-(Rho/PKC)-actin organisation | 3 |
| PDGF signalling | PDGFRa/b-SPHK-CRK-mitogenesis* | 3 |
| Protein Kinase A signalling | PKA-PHK-PYG-glycolysis* | 3 |
| Regulation of cellular mechanics by calpain protease | CNG-CALPAIN-RB | 3 |
| role of JAK in IL-6 type cytokine signalling | (GP130-OSMR)-JAK2-STAT1/3/5-gene expression* | 3 |
| Role of JAK2 in Hormone-like cytokine signalling | GHR-JAK2-IRS-PI3K/AKT SIGNALLING* | 3 |
| Role of JAK2 in Hormone-like cytokine signalling | GHR-JAK2-STAT1/3-GENE EXPRESSION* | 3 |
| Role of JAK2 in Hormone-like cytokine signalling | GHR-JAK2-STATS-GENE EXPRESSION* | 3 |
| Role of Macrophages, Fibroblasts and Endothelial Cells in Rheumatoid Arthritis | GP130-JAK2-STAT3-gene expression* | 3 |
| Role of Pattern Recognition Receptors in Recognition of Bacteria and Viruses | NALP3-casp1-IL1b* | 3 |
| Role of Pattern Recognition Receptors in Recognition of Bacteria and Viruses | NOD1-Casp1-IL1b* | 3 |
| Role of PI3K/AKT signalling in the Pathogenesis of Influenza | PI3K-AKT-IKB, NFKB | 3 |
| Role of tissue factor in cancer | PAR2-ERK1/2-HBEGF-angiogenesis | 3 |
| Role of tissue factor in cancer | PAR2-ERK1/2-VEGFa-angiogenesis | 3 |
| Role of tissue factor in cancer | PAR2-p38/MAPK-uPar-tumour invasion | 3 |
| Role of tissue factor in cancer | PAR2-p38/MAPK-IL-1b-angiogenesis | 3 |
| Role of tissue factor in cancer | PAR2-p38/MAPK-VEGFa-angiogenesis | 3 |
| STAT3 pathway | cytokine receptors-TYK2/JAK2-STAT3-transcription-immune response-proliferation-survival* | 3 |
| STAT3 pathway | GFR-JAK2/SRC-STAT3-transcription-immune response-proliferation-survival * | 3 |
| Synaptic long term depression | AMPAR-Lyn-PKC-Phosphorylation* | 3 |
| Tec Kinase signalling | FCeR1-TEC kinase-(FAK, PKC, PAK, VAV, FACTIN, RHOGTPASE, NFKB, JNK, STAT-TFII-1*) | 3 |
| Tec Kinase signalling | TLR4-TEC kinase-(FAK, PKC, PAK, VAV, FACTIN, RHOGTPASE, NFKB, JNK, STAT-TFII-1*) | 3 |

TABLE 4

Comparison of route scores between H3N2 and H1N1.

| Pathway | Route | H3N2 | | | | H1N1 | | | |
| --- | --- | --- | --- | --- | --- | --- | --- | --- | --- |
| | | Severe vs Baseline H3N2 | Severe vs Peak H3N2 | Severe vs Mild H3N2 | Severe vs Moderate H3N2 | Severe vs Baseline H1N1 | Severe vs Peak H1N1 | Severe vs Mild H1N1 | Severe vs Moderate H1N1 |
| Growth Hormone signaling | GHR-JAK2-ERK1/2-CEBPA* | 100.00 | 93.33 | 100.00 | 100 | 75 | 75 | 75 | 75 |
| PPARα/RXRα Activation | ADIPOR-AMPK-P38MAPK-PPARalpha-REGULATION of growth hormone genes | 100.00 | 100.00 | 100.00 | 100 | 100 | 100 | 100 | 75 |
| GM-CSF signaling | GMCSFRA-HCK-PI3K-AKT-cell survival/cell proliferation* | 100.00 | 100.00 | 100.00 | 100 | 100 | 100 | 100 | 100 |
| Sphingosine-1-phosphate signaling | SIPR(2/3/4)-GAI-PI3K-AKT-CELL SURVIVAL* | 100.00 | 100.00 | 100.00 | 100 | 100 | 100 | 100 | 100 |
| ceramide signaling | SMPD-(ceramide)-PI3K-AKT-apoptosis* | 100.00 | 100.00 | 100.00 | 100 | 100 | 100 | 100 | 100 |
| IL-8 | CXCR1/2-PI3K-MEK1/2-ERK1/2-(Neutrophil Degranulation) | 100.00 | 93.33 | 100.00 | 100 | 75 | 75 | 100 | 100 |
| Paxillin signaling | Integrina/b-FAK-GRB2-SOS-Ras-ERK/MAPK* | 100.00 | 100.00 | 100.00 | 100 | 100 | 100 | 100 | 100 |
| Tec Kinase signaling | FCeR1-TEC kinase-(FAK, PKC, PAK, VAV, FACTIN, RHOGTPASE, NFKB, JNK, STAT-TFII-1*) | 100.00 | 100.00 | 100.00 | 100 | 100 | 100 | 100 | 100 |
| Tec Kinase signaling | TCR-SRC-TEC KINASE-(FAK, PKC, PAK, VAV, FACTIN, RHOGTPASE, NFKB, JNK, STAT-TFII-1*) | 100.00 | 100.00 | 100.00 | 100 | 100 | 100 | 100 | 100 |
| Tec Kinase signaling | TLR4-TEC kinase-(FAK, PKC, PAK, VAV, FACTIN, RHOGTPASE, NFKB, JNK, STAT-TFII-1*) | 100.00 | 100.00 | 100.00 | 100 | 100 | 100 | 100 | 100 |
| signaling by Rho Family GTPases | Integrin-ARHGEF-RHO-PKNI-celltrafficking* | 100.00 | 100.00 | 100.00 | 100 | 75 | 75 | 75 | 75 |
| Regulation of cellular mechanics by calpain protease | CNG-CALPAIN-RB | 100.00 | 100.00 | 100.00 | 100 | 100 | 100 | 100 | 100 |
| Tec Kinase signaling | Integrin-FAK-TEC KINASE-(FAK, PKC, PAK, VAV, FACTIN, RHOGTPASE, NFKB, JNK, STAT-TFII-1*) | 100.00 | 100.00 | 100.00 | 100 | 100 | 100 | 100 | 100 |
| Acute myeloid leukemia signaling | FLT3-GRB2-SOS-RAS-RAF-MEK-ERK1/2-cell proliferation | 100.00 | 100.00 | 100.00 | 85.71 | 100 | 100 | 100 | 100 |
| signaling by Rho Family GTPases | Integrin-ARHGEF-RHO-FAK-cytoskeletal reorganisation* | 100.00 | 95.23 | 100.00 | 100 | 100 | 100 | 100 | 100 |
| IL-8 | CXCR1/2-Ras-Raf-MEK1/2-ERK1/2-(Neutrophil Degranulation) | 100.00 | 91.67 | 100.00 | 100 | 80 | 80 | 100 | 100 |
| JAK/STAT | cytokine receptor-JAK-STAT-(CFOS-IL6-SOCS-BCLXL)* | 100.00 | 91.67 | 100.00 | 100 | 75 | 75 | 100 | 100 |
| MSP-RON signaling pathway | RON-PI3K-PKC zeta-F-ACTIN-phagocytic activity in macrophages* | 100.00 | 91.67 | 100.00 | 100 | 75 | 100 | 75 | 75 |
| Germ Cell-Sertoli Cell Junction signaling | TGFbetaR-RAS-MEK1/2-ERK1/2-actin depolymerisation* | 100.00 | 91.67 | 100.00 | 100 | 100 | 100 | 100 | 100 |
| Role of MAPK signaling in the Pathogenesis of Influenza | ASK-1-MKK4/7-JNK-CASP3-APOPTOSIS | 100.00 | 83.33 | 100.00 | 100 | 75 | 75 | 75 | 75 |
| Role of PI3K/AKT signaling in the Pathogenesis of Influenza | PI3K-AKT-IKB, NFKB | 100.00 | 77.78 | 100.00 | 100 | 100 | 100 | 75 | 75 |
| Protein Kinase A signaling | PKAr/PKAc-RAP1-BRAF-MEK1/2-ERK1/2-ELK1* | 100.00 | 100.00 | 83.33 | 83.33 | 100 | 83.33 | 83.33 | 83.33 |
| IL-8 | CXCR1/2-PI3K-Akt-AP1-IntegrinAlphavBeta3 (Chemotaxis) | 100.00 | 80.55 | 80.00 | 100 | 75 | 80 | 100 | 100 |
| Production of nitric oxide and ROS in macrophages | TLR2/4-MKK4/7-JNK-AP1 | 100.00 | 91.67 | 75.00 | 100 | 100 | 100 | 100 | 100 |

Figure 5:
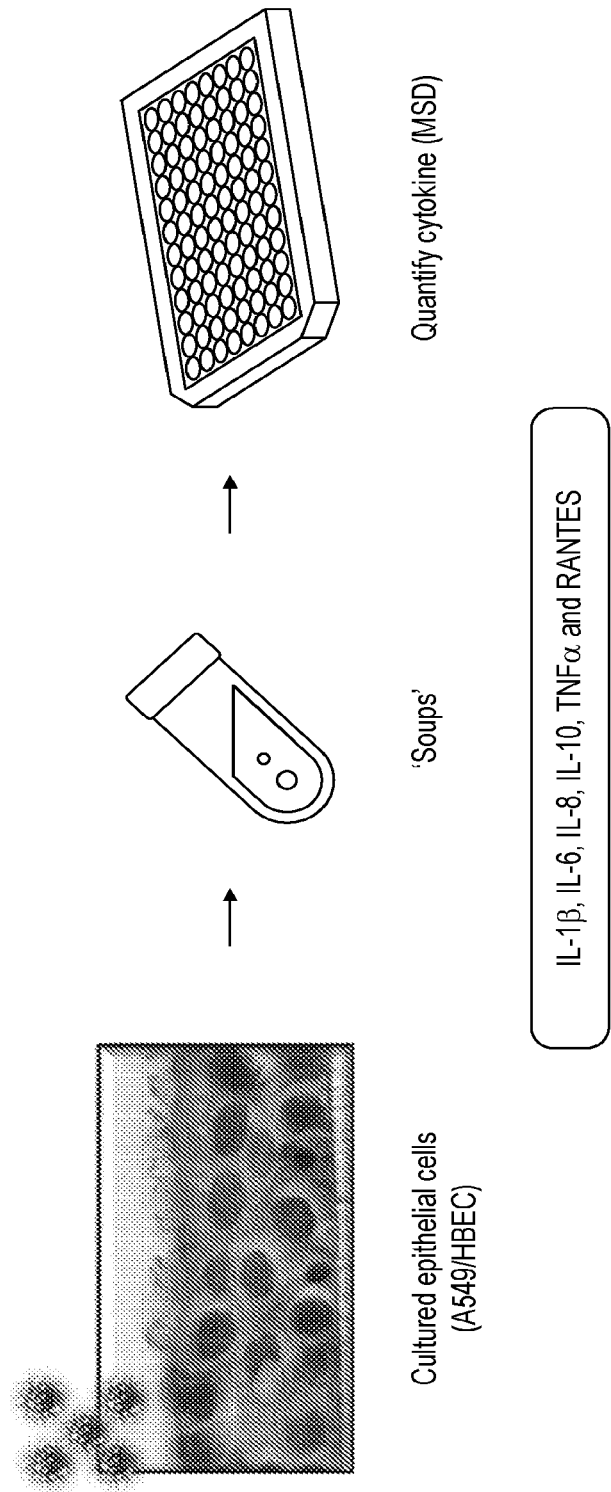

Example 2: Effects of p38MAPK Inhibition on Inflammatory Mediator Release in Key Cell Types Relevant to Severe Influenza Two p38 MAPK inhibitors were used in in vitro and ex vivo experiments: 1) PH797804, an ATP-competitive highly potent, selective and metabolically stable inhibitor of p38 (Hope HR1, et al., Anti-inflammatory properties of a novel N-phenyl pyridinone inhibitor of p38 mitogen-activated protein kinase: preclinical-to-clinical translation, *Pharmacol. Exp. Ther.,* 2009 (December); 331(3): 882-95); and 2) Dilmapimod (SB-681323—Betts JC1, et al., Gene expression changes caused by the p38 MAPK inhibitor dilmapimod in COPD patients: analysis of blood and sputum samples from a randomized, placebo-controlled clinical trial, *Pharmacol. Res. Perspect.,* 2015 (February); 3(1): e00094). The structures of these compounds are as follows:

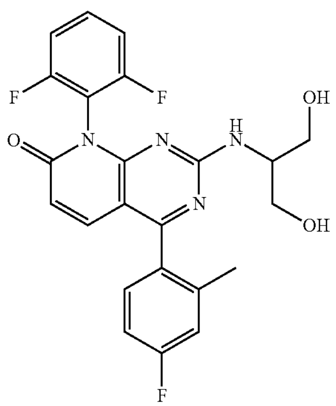

Dilmapimod

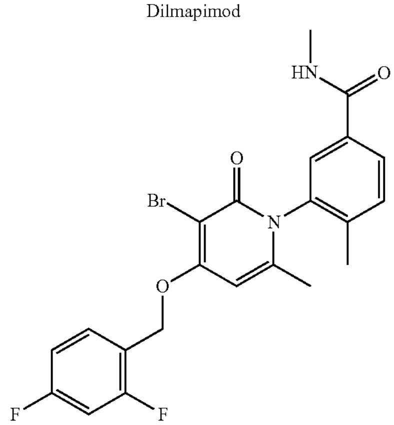

PH797804

Experimental testing of p38MAPK inhibition was carried out in three cell types that are key players in the pathology of severe influenza: epithelial; endothelial; and immune cells (FIG. 4).

Epithelial Cells

A549 cells (adenocarcinoma human alveolar basal epithelial cells) or HBEC (Human Bronchial Epithelial Cells) were infected with A/Perth/16/2009(H3N2) virus from which viral conditioned media (or 'viral soup') was collected. In the experiments described here, the application of viral soup either back onto epithelial cells or onto the other cell types of interest (endothelial and immune) was performed in order to simulate the action of inflammatory mediators that are produced from Influenza infected epithelial cells.

For infection, high titre stocks of Influenza (H3N2) virus were produced by infection of MDCK-RVL cells (available from ATCC as MDCK (NBL-2) (ATCC® CCL-34), derived from a kidney of an apparently normal adult female cocker spaniel, September, 1958, by S. H. Madin and N. B. Darby. The line is hyperdiploid, and there is a bi-modal chromosome number distribution. There are no consistent identifiable marker chromosomes. One normal X chromosome is present in most spreads. The cells are positive for keratin by immunoperoxidase staining). MDCK-RVL cells were plated in T175 flask and allowed to grow to 85-90% confluence. The next day, cells were washed twice with infection media. The Influenza A/Perth/16/2009 (H3N2) stock was removed from −80° C. and thawed on ice. The cells were infected with virus stock at 0.01 MOI for one hour in infection media. At the end of incubation period, unbound virus was removed from the cells. The cells were washed once with infection media and overlaid with infection media and allowed to incubate for 48 hours in 37° C. at 5% CO2/air incubator. After incubation, the flasks were frozen at −80° C. for a day. Next day, the flasks were thawed at room temperature and virus supernatant was centrifuged (2000 g, 10 min) and pooled together. The virus stock was aliquoted and stored at −80° C.

Viral "soups" were prepared using the A549 cell line and primary human bronchial epithelial cells (HBECs). For the preparation of A549 soups cells were plated in a T175 flask and allowed to grow to obtain 85-90% confluence. The cells were washed twice with infection media. The Influenza A/Perth/16/2009 (H3N2)-WGC stock was removed from −80° C. and thawed on ice. The cells were infected with virus stock at 0.01 MOI for one hour in infection media. The unbound virus was removed from the cells at the end of the incubation period and cells were washed once with infection media before overlaying with infection media. The cells were incubated for 48 hours in 37° C. at 5% CO2/air incubator. After incubation, the media ('viral soup') was collected from all flasks, centrifuged (2000 g, 10 min) and pooled together. The viral soup was aliquoted and stored at −80° C. For the preparation of HBEC soups cells were passaged (P-3 or P-4) in T-175 flasks and infected with Influenza A/Perth/16/2009 (H3N2)-WGC stock at 0.01 MOI for one hour in HBECS infection media. Following incubation, the virus was removed and cells were washed with HBECS growth medium. The cells were then overlaid with HBECS infection medium, for 48 hours in 37° C. at 5% $CO_2$/air incubator. At the end of incubation period, the HBEC viral soup was processed in a similar way to the A549 soup.

Viral growth kinetics were optimised for generating viral soups. To determine multistep growth curves, A549 cells or HBECs were infected with virus at an MOI of 0.01 TCID50/cell at 37° C. for one hour. Following incubation, the cells were washed and overlaid with respective infection media. The samples were harvested for viral titre and measurement of cytokines at various time points for 72 hours. The viral titres were obtained by TCID50 on MDCK cells.

Prior to experimental testing both A549 and HBEC soup preparations were evaluated by electrogenerated chemiluminescence for the presence of inflammatory mediators using methods as recommended by the vendor (https://web.archive.org/web/20160522190937/https://www.mesoscale.com/). Both soup preparations were found to contain elevated levels of the following cytokines (IL1-β, IL-6, IL-8, IL-10, TNFα and RANTES; FIG. 5).

In vitro data were generated from A549 cells to test the effect of A549 viral soup application on p38 activation as measured by western blotting of the phosphorylation status of p38MAPK itself and downstream signalling target, HSP27. For western blotting confluent cells were washed in PBS and lysed in RIPA with protease inhibitor (Sigma-P8340), phosphatase inhibitor cocktails 2 and 3 (Sigma P5726 and P0044) and phosphatase inhibitors Na3VO4 and NaF on ice. Protein concentrations were determined using the Pierce BCA Protein Assay Kit and equal concentrations of each sample created in 4× Laemmli sample buffer (BIO-RAD 161-0747) with 2-mercaptoethanol. Samples were run on a 12% gel and then transferred on to nitrocellulose. Membranes were blocked using 5% milk powder, then probed for phospho-HSP27 (Ser82) (D1H2F6) XP® Rabbit (CST #9709) or HSP27 (G31) Mouse (CST #2402). Secondary antibodies used were Peroxidase AffiniPure Goat Anti-Rabbit or Mouse IgG (H+L) (Jackson Immuno Research Laboratories 111-035-003). Membranes were stripped for re-probing using Restore™ PLUS Western Blot Stripping Buffer (Life technologies #46430). The membranes were treated with Amersham ECL Prime Western Blotting Detection Reagent (GE/Amersham #RPN2232) and imaged using ChemiDoc™ Touch Imaging System (BIO-RAD). Analysis was performed using the Image Lab software.

Figure 6:
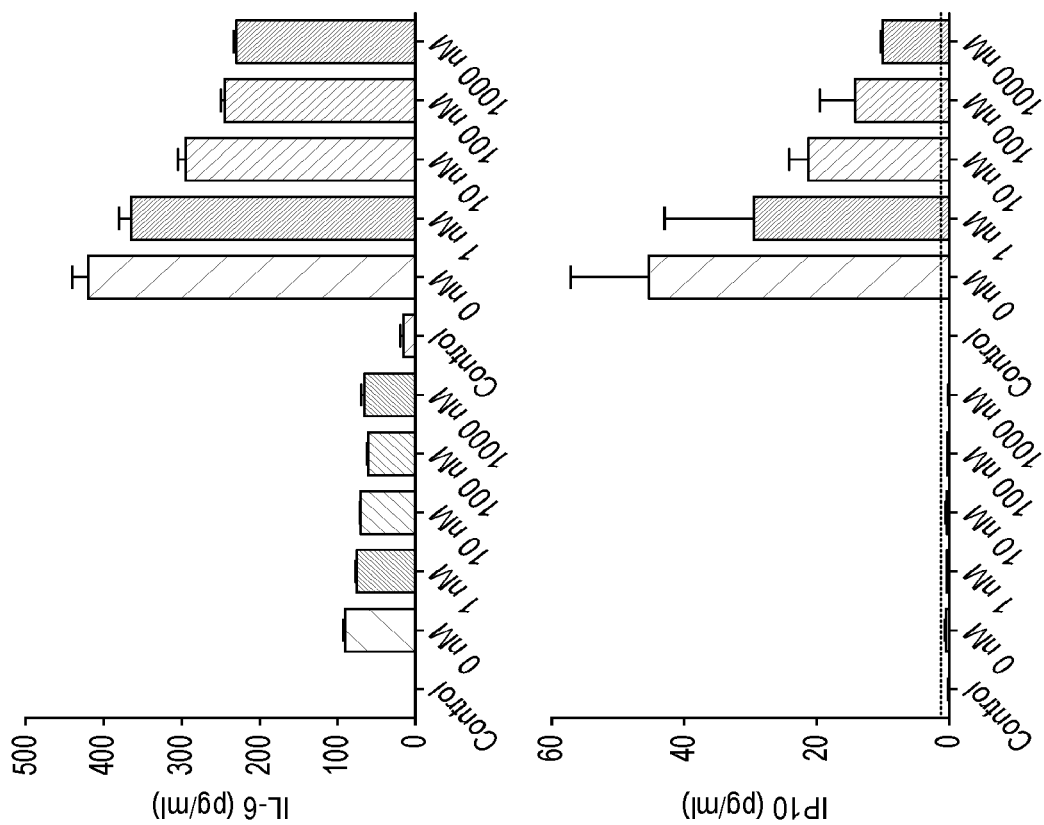
Figure 6:
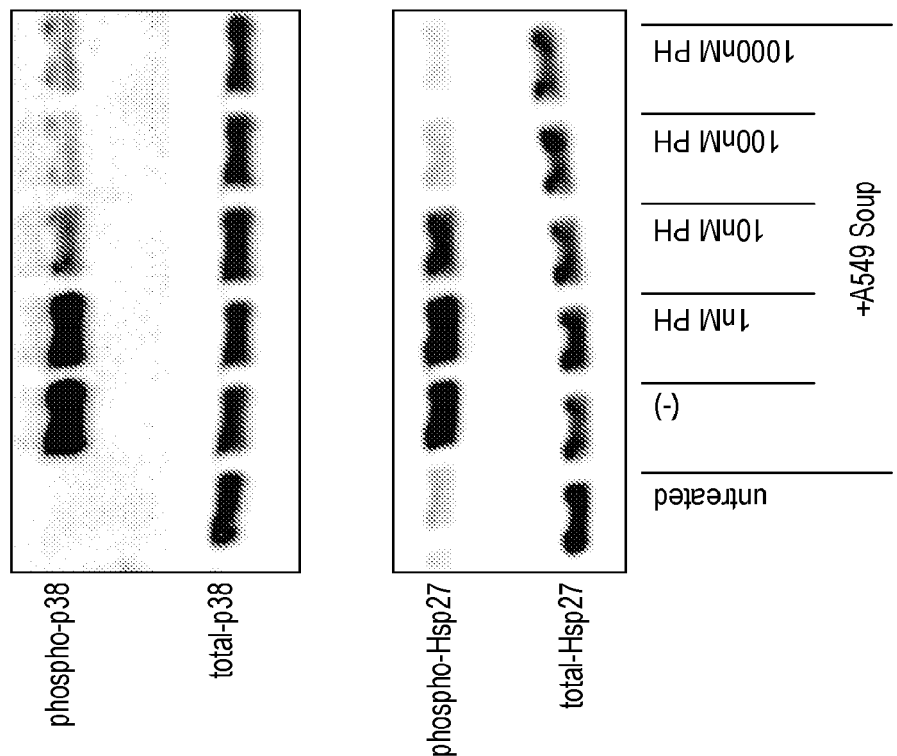

Induction of phosphorylation on both of these enzymes was detected indicating that p38MAPK is activated following application of A549 viral soup (FIG. 6). Furthermore, incubation with p38 MAPK inhibitors (Dilmapimod and PH 797804) was shown to dose dependently inhibit the induction of both p38MAPK and HSP27 phosphorylation by our A549 viral soup, confirming that this induction is a p38MAPK dependent process within these epithelial cells.

The effect of A549 viral soup on inflammatory cytokine production in A549 cells as measured by electrogenerated chemiluminescence was also explored. As shown in FIG. 6, A549 soup was found to induce the production of key inflammatory cytokines (IL-6 and IP-10) to a greater extent compared with control uninfected A549 soup. Application of the two p38 MAPK inhibitors on A549 cells prior to A549 viral soup application significantly attenuated release of both IL-6 and IP-10 (FIG. 6). These data demonstrate that the release of inflammatory mediators in response to A549 viral soup application on A549 cells is a p38MAPK dependent process.

Endothelial Cells

The application of HBEC viral soup on to Human Umbilical Vein Endothelial Cells (HUVECs) was performed in order to simulate the interaction of inflammatory mediators that are produced from Influenza infected epithelial cells onto endothelial cells.

In vitro data were generated from HUVEC cells to test the effect of HBEC viral soup application on p38 activation as measured by western blotting of the phosphorylation status of the p38MAPK downstream signalling target, HSP27. Induction of phosphorylation on HSP27 was detected indicating that p38MAPK is activated following application of HBEC viral soup (FIG. 5). Furthermore, pre-incubation with p38 MAPK inhibitors (Dilmapimod and PH 797804) was shown to dose dependently inhibit the induction of HSP27 phosphorylation by the HBEC viral soup, confirming that this induction is a p38MAPK dependent process within these endothelial cells.

Figure 7:
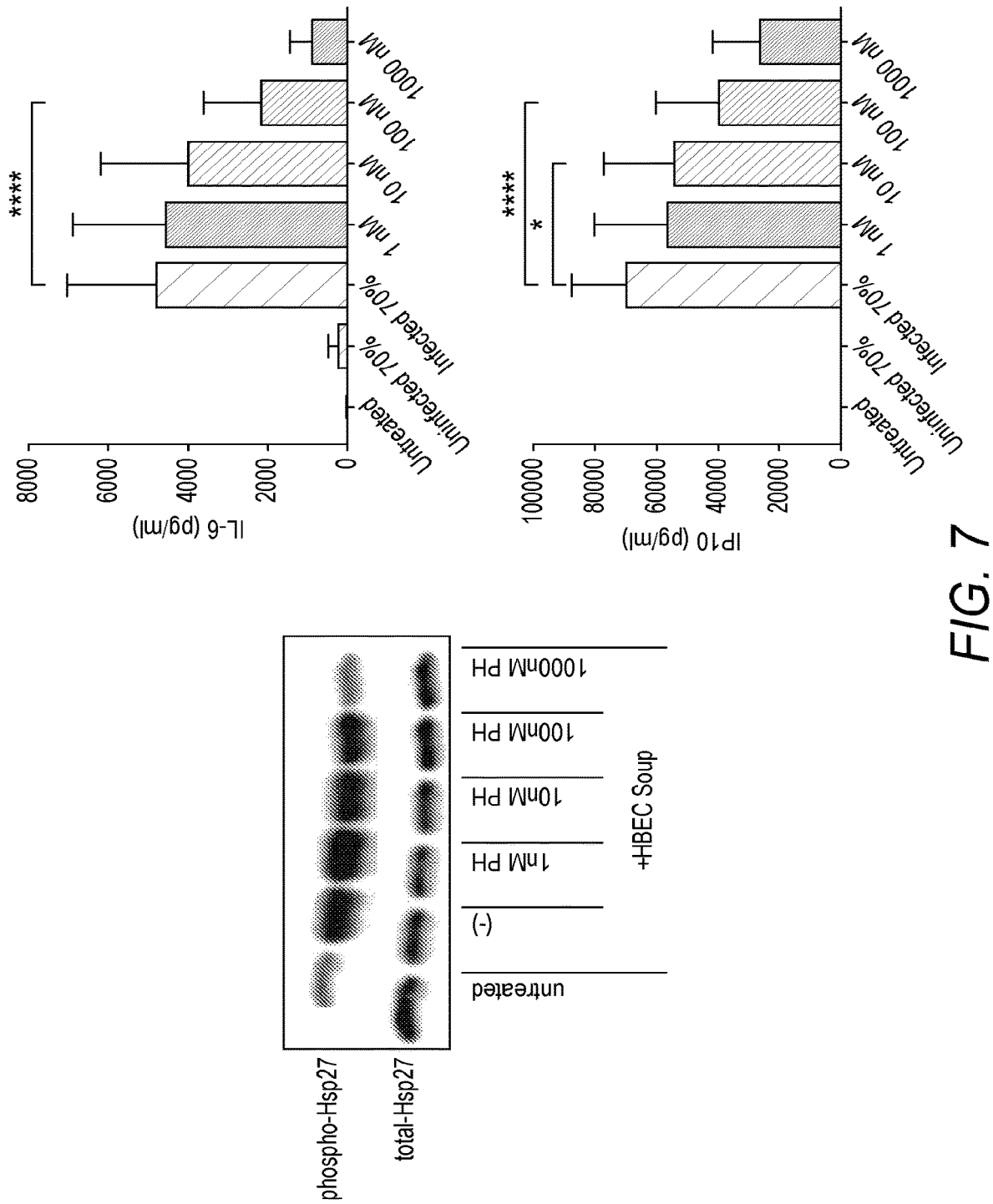

The effect of HBEC viral soup on inflammatory cytokine production in HUVEC cells as measured by electrogenerated chemiluminescence (see methods) was also explored. As shown in FIG. 5, HBEC viral soup was found to induce the production of key inflammatory cytokines (IL-6 and IP-10) to a greater extent compared with control HBEC uninfected soup. Incubation of HUVEC cells with the two p38 MAPK inhibitors prior to HBEC viral soup application was found to significantly attenuate the HBEC viral soup induced release of both IL-6 and IP-10 (FIG. 7). These data demonstrate that the release of inflammatory mediators in response to HBEC viral soup application in HUVEC endothelial cell is a p38MAPK dependent process.

Immune Cells

The application of A549 viral soup onto human Peripheral Blood Mononuclear Cells (PBMCs) was performed in order to simulate the interaction of inflammatory mediators that are produced from Influenza infected epithelial cells onto immune cells. PBMCs were isolated according to the manufacturers recommendations (Bøyum, A., Separation of leucocytes from blood and bone marrow, *Scand. J. Clin. Lab. Invest.*, 1968, 21, suppl. 97).

Figure 8:
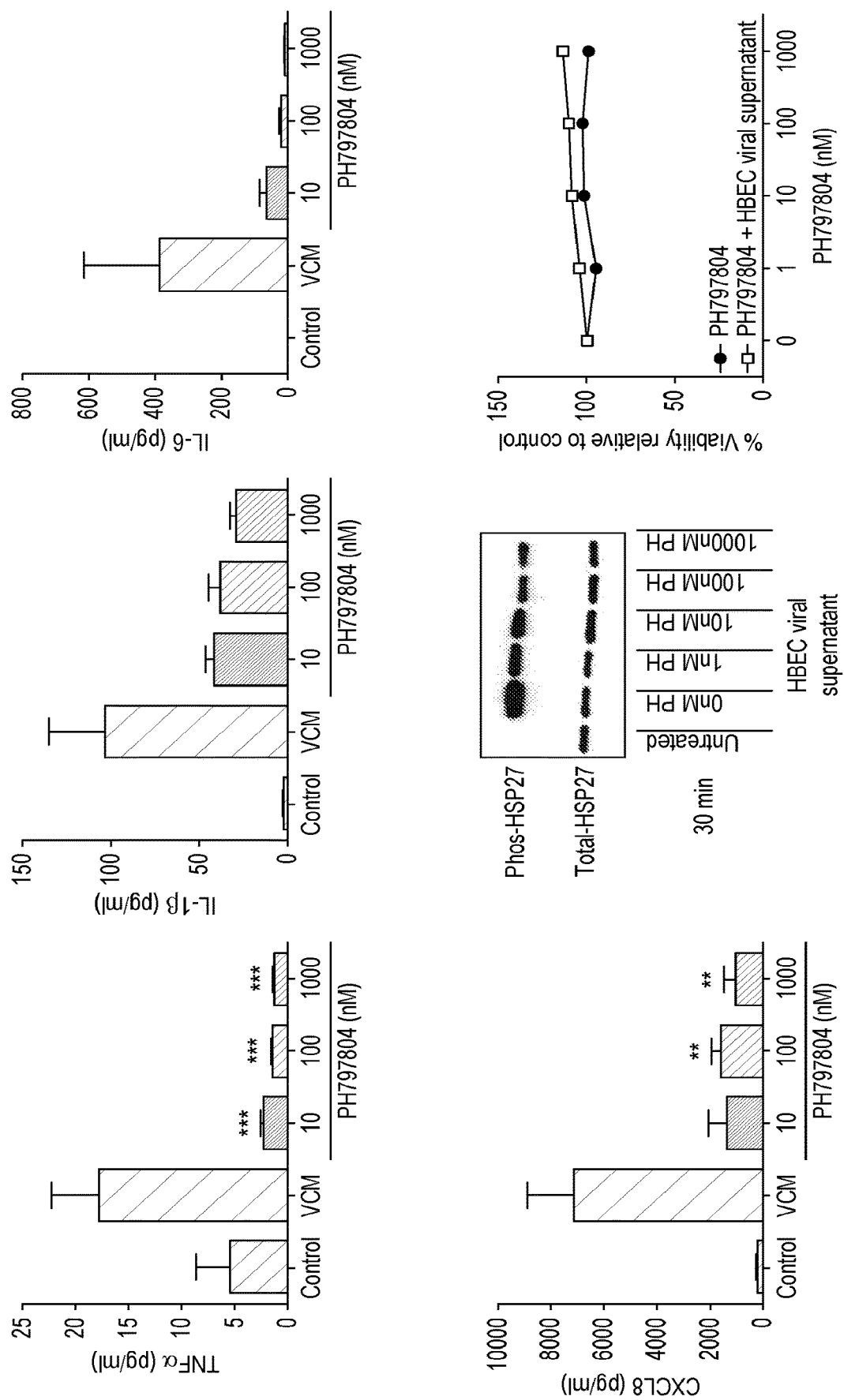

Ex vivo data were generated from immune cells to test the effect of A549 viral soup application on p38 activation as measured by Western blotting (see above for method) of the phosphorylation status of the p38MAPK downstream signalling target, HSP27. Induction of phosphorylation on HSP27 was detected, indicating that p38MAPK is activated following application of A549 viral soup (FIG. 8). Furthermore, pre-incubation with p38 MAPK inhibitors (Dilmapimod and PH 797804) was shown to dose dependently inhibit the induction of HSP27 phosphorylation by the A549 viral soup, confirming that this induction is a p38MAPK dependent process within these immune cells (FIG. 8).

The effect of A549 viral soup on inflammatory cytokine production in immune cells as measured by electrogenerated chemiluminescence (see above) was also explored. As shown in FIG. 8, A549 viral soup was found to induce the production of key inflammatory cytokines (TNFα, IL-6 and CXCL8) to a greater extent compared with control A549 uninfected soup. Pre-incubation of p38 MAPK inhibitors (Dilmapimod and PH 797804) on immune cells prior to A549 viral soup application was found to significantly attenuate the A549 viral soup induced release of TNFα, IL-1-β, IL-6 and CXCL8 (FIG. 8). These data demonstrate that the release of inflammatory mediators in response to A549 viral soup application in immune cells is a p38MAPK driven process.

Figure 9:
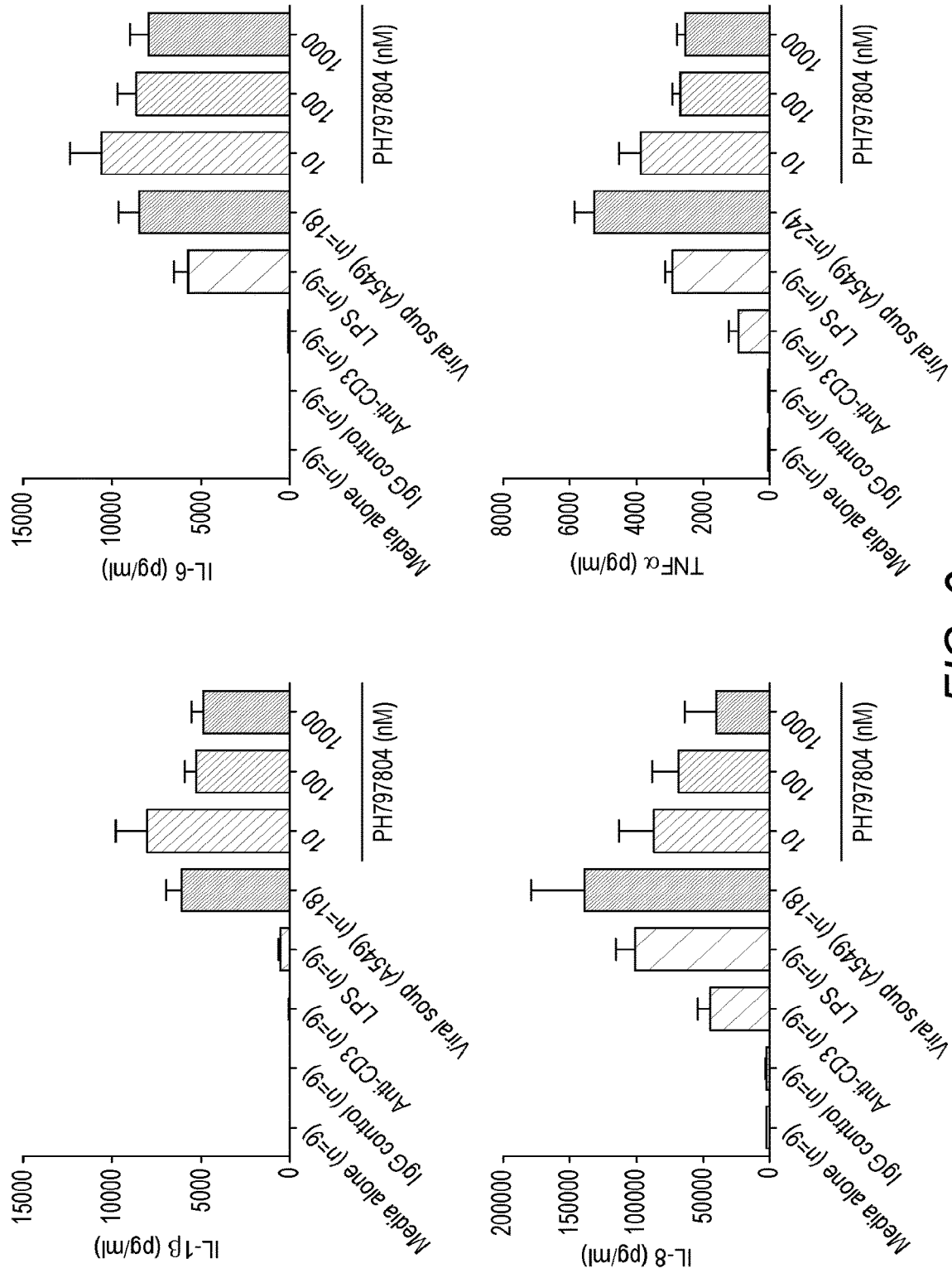

Additional ex vivo data were generated from immune cells whereby the induction of inflammatory mediators in response to A549 viral soup was compared to known inflammatory stimulants (anti-CD3 and LPS). The induction of TNFα, IL-1-β, IL-6 and IL-8 by A549 viral soup was found to be greater compared with these known inflammatory stimulants (FIG. 9).

Example 3: p38 MAPK Inhibitory Activity

The enzyme inhibitory activity of a compound may be determined by fluorescence resonance energy transfer (FRET) using synthetic peptides labelled with both donor and acceptor fluorophores (Z-LYTE, Invitrogen).

Recombinant, phosphorylated p38 MAPK gamma (MAPK12:Millipore) is diluted in HEPES buffer, mixed with the candidate compound at desired final concentrations and incubated for two hours at room temperature. The FRET peptide (2 µM) and ATP (100 µM) are next added to the enzyme/compound mixture and incubated for one hour. Development reagent (protease) is added for one hour prior to detection in a fluorescence microplate reader. The site-specific protease only cleaves non-phosphorylated peptide and eliminates the FRET signal. Phosphorylation levels of each reaction are calculated using the ratio of coumarin emission (donor) over fluorescein emission (acceptor) with high ratios indicating high phosphorylation and low ratios, low phosphorylation levels. The percentage inhibition of each reaction is calculated relative to non-inhibited control, and the 50% inhibitory concentration ($IC_{50}$ value) then calculated from the concentration-response curve.

For p38 MAPK alpha (MAPK14: Invitrogen), enzyme activity is evaluated indirectly by determining activation/phosphorylation of the down-stream molecule, MAPKAP-K2. The p38 MAPK a protein is mixed with its inactive target MAPKAP-K2 (Invitrogen) and the candidate compound for two hours at room temperature. The FRET peptide (2 µM), which is a phosphorylation target for MAPKAP-K2, and ATP (10 µM) are then added to the enzymes/compound mixture and incubated for one hour. Development reagent is then added and the mixture incubated for one hour before detection by fluorescence completed the assay protocol.

Example 4: P38MAPK Inhibition (p38i) Versus Inhibition of Other Potential Targets As indicated in Example 1 above, a number of targetable nodes in the 95 pathway routes highlighted by transcriptomic and bioinformatics were identified. The compound profiling experiments in Example 2 show that p38i is effective in reducing the production of inflammatory mediator release in cell types relevant to the pathology of severe influenza. This was found not to be the case for 9 other nodes that were examined: PI3K, MEK, ERK, JNK, JAK/STAT, PKC, SRC, BtK and mTor. Drug inhibition of none of these 9 nodes gave an inhibition profile as effective as p38i in epithelial, endothelial and immune cells.

Figure 10:
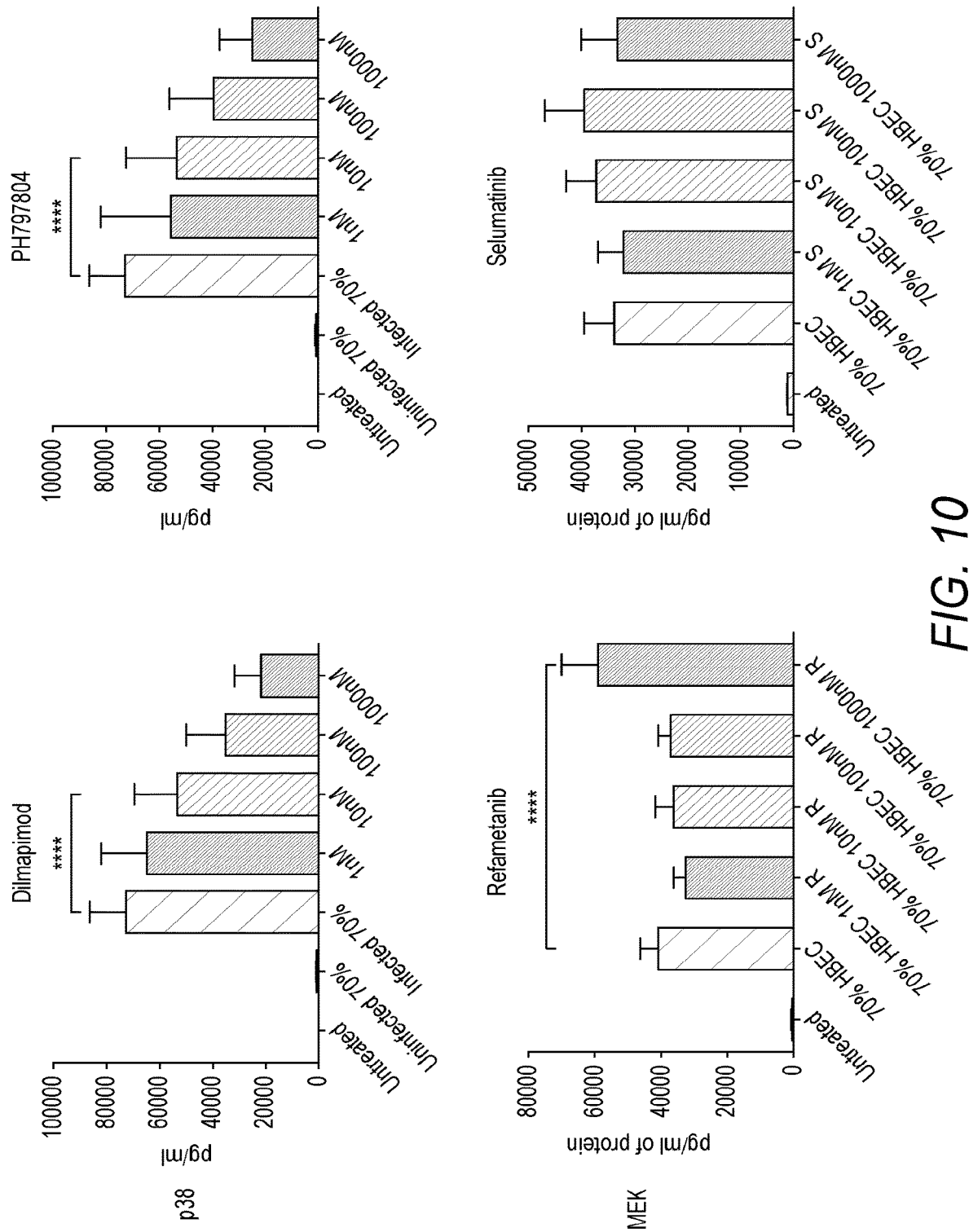

By way of example, data comparing p38i versus mitogen-activated protein kinase kinase (MEK) inhibition (MEKi) by MEK inhibitors Refametinib (Iverson C et al., RDEA119/BAY 869766: a potent, selective, allosteric inhibitor of MEK1/2 for the treatment of cancer. *Cancer Res.,* 2009; 69: 6839-6847) and Selumetinib (Huynh H et al., Targeted inhibition of the extracellular signal-regulated kinase pathway with AZD6244 (ARRY-142886) in the treatment of hepatocellular carcinoma, *Molecular Cancer Therapeutics,* 2007; 6:138-146) are presented in FIG. 10 of the accompanying drawings.

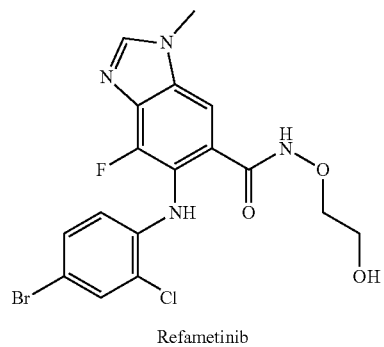

Refametinib

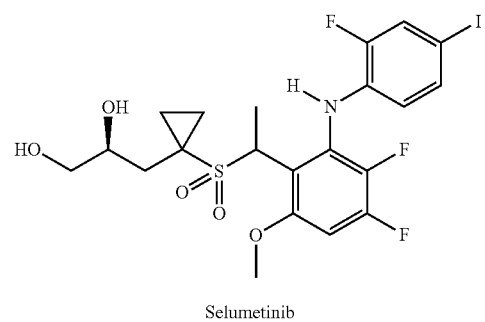

Selumetinib

Neither Refametinib nor Selumetinib showed dose-dependent inhibition of IP10 production in endothelial cells stimulated with HBEC viral soup and actually appeared to increase levels of IP10 at higher drug concentrations (see FIG. 10).

A number of potential drug targets have been proposed for severe influenza (e.g. Liu Q et al., 2015 and Fedson D S, 2009). p38i was also compared versus drug compounds for a selection of these proposed targets.

For these experiments, PH797804 was benchmarked versus corticosteroid (methyl prednisolone), macrolide (Azithromycin), PPAR agonist (Pioglitazone), PDE4 inhibitor (Roflumilast), NFκB inhibitor (EVP4593) and statin (Pravastatin) at four drug concentrations (1 nM, 10 nM, 100 nM and 1000 nM) in endothelial cells (HUVECs stimulated with HBEC viral soup), or immune cells (PBMCs plus granulocytes stimulated with A549 viral soup as described in Example 2 above).

The effects of drug compound administration on IP-10, IL-8 and MCP-1 production from endothelial cells and on IL-1β, IL-6, IL-8 and TNF-α production from immune cells was assayed using electrogenerated chemiluminescence. In immune cells, corticosteroid and macrolide drug treatment showed dose-dependent inhibition of all four assayed cytokines, whereas p38i showed dose-dependent inhibition of only three of the four. The inhibitory profile of the other drugs tested was variable and did not match that of corticosteroid, macrolide, or p38i. The results are summarised in Table 5 below.

TABLE 5

Comparison of inhibitory effects of drug compounds for literature-proposed targets for severe influenza versus p38i. PBMCs plus granulocytes were isolated as described in Example 2 and stimulated with A549 viral soup. Secreted cytokine levels were assayed by electrogenemted chemiluminescence and IC50 and iMax values were calculated from the dose responses using non-linear regression fit using a scientific 2D graphing and statistics software package (GraphPad PRISM ® version 6.07 software). Where data did not show a dose-dependent inhibition, the IC50 and iMax values were not calculated (empty boxes).

|  | p38 inhibitor PH797804 | | Corticosteroid Methyl Prednisolone | | Macrolide Azithromycin | | PPAR agonist Pioglitazone | | PDE4 inhibitor Roflumilast | | NFkB inhibitor QNZ (EVP4593) | | Statin Pravastatin | |
| --- | --- | --- | --- | --- | --- | --- | --- | --- | --- | --- | --- | --- | --- | --- |
|  | IC50 (nM) | iMax (%) | IC50 (nM) | iMax (%) | IC50 (nM) | iMax (%) | IC50 (nM) | iMax (%) | IC50 (nM) | iMax (%) | IC50 (nM) | iMax (%) | IC50 (nM) | iMax (%) |
| IL1B | 9.7 | 79% | 8.4 | 77% | 0.5 | 50% |  |  |  |  |  |  |  |  |
| IL8 | 2.3 | 87% | 8.4 | 90% | 0.8 | 46% | 0.1 | 37% | 0.09 | 31% | 0.2 | 47% |  |  |
| TNFa | 3.9 | 91% | 20.2 | 79% | 86.9 | 63% |  |  | 10.8 | 74% | 43.6 | 37% |  |  |
| IL6 |  |  | 36.6 | 57% | 119 | 45% | 0.02 | 41% |  |  |  |  |  |  |

Figure 11:
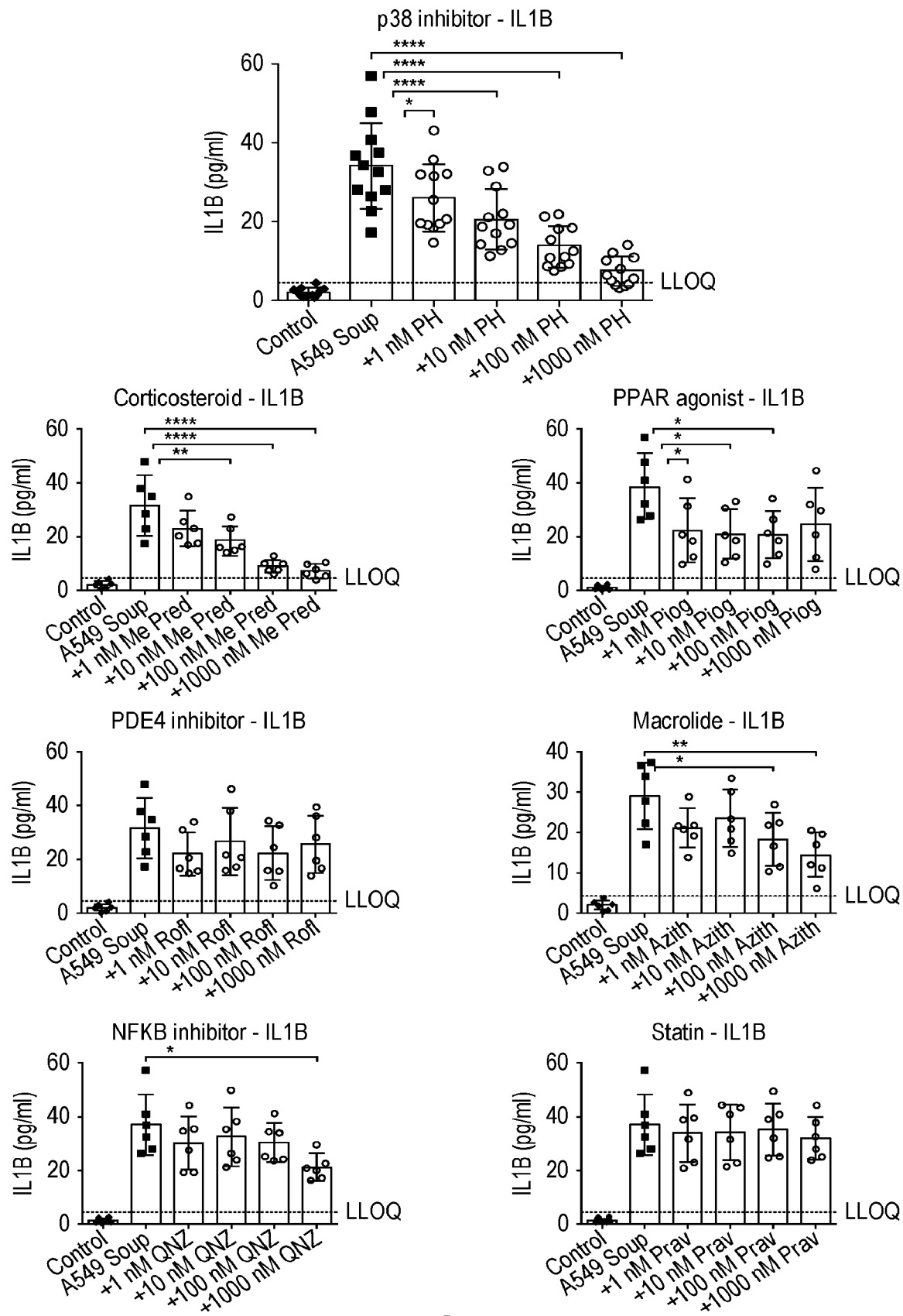
Figure 12:
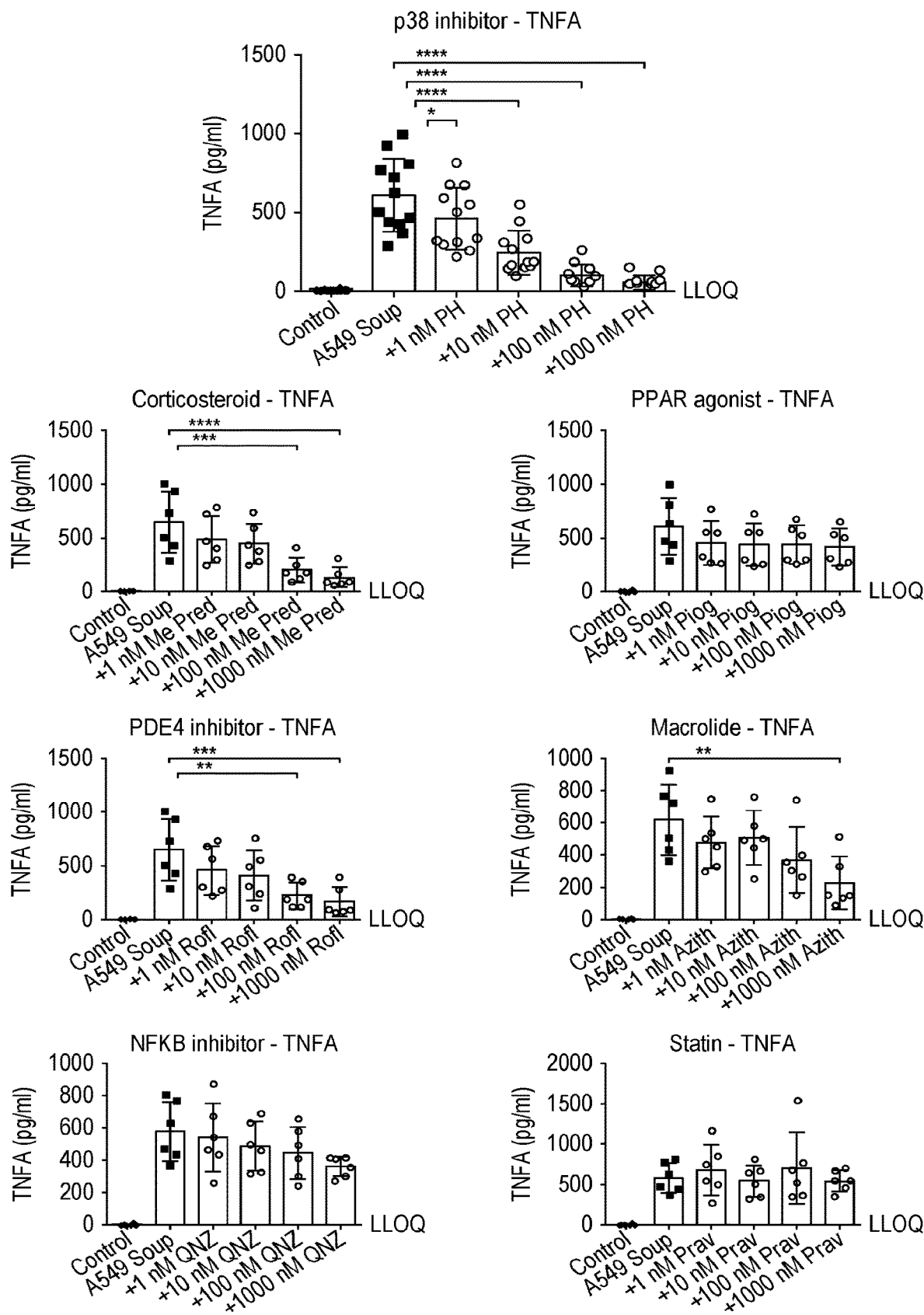

The inhibition plots for IL1-b and TNFα for the compounds tested are shown in FIGS. 11 and 12.

With endothelial cells, in contrast to immune cells, only p38 and NFκB inhibitors showed dose-dependent inhibition of the three cytokines assayed. None of the other drugs tested showed a comparable inhibitory effect. The results are summarised in Table 6 below.

TABLE 6

Comparison of inhibitory effects of drug compounds for literature-proposed targets for severe influenza versus p38i. HUVEC cells were stimulated with HBEC viral soup. Secreted cytokine levels were assayed by electrogenerated chemiluminescence and IC50 and iMax values were calculated from the dose responses using non-linear regression fit with a scientific 2D graphing and statistics software package (GraphPad PRISM ® version 6.07 software). Where data did not show a dose-dependent inhibition, the IC50 and iMax values were not calculated.

|  | p38 inhibitor PH797804 | | Corticosteroid Methyl Prednisolone | | Macrolide Azithromycin | | PPAR agonist Pioglitazone | | PDE4 inhibitor Roflumilast | | NFkB inhibitor QNZ (EVP4593) | | Statin Pravastatin | |
| --- | --- | --- | --- | --- | --- | --- | --- | --- | --- | --- | --- | --- | --- | --- |
|  | IC50 (nM) | iMax (%) | IC50 (nM) | iMax (%) | IC50 (nM) | iMax (%) | IC50 (nM) | iMax (%) | IC50 (nM) | iMax (%) | IC50 (nM) | iMax (%) | IC50 (nM) | iMax (%) |
| IP10 | 7.5 | 88% |  |  |  |  |  |  |  |  | 3.3 | 72% | 78 | 35% |
| IL8 | 28.9 | 86% |  |  |  |  |  |  |  |  | 6.5 | 60% |  |  |
| MCP1 | 13.1 | 36% |  |  |  |  |  |  |  |  | 3.84 | 44% |  |  |

Figure 13:
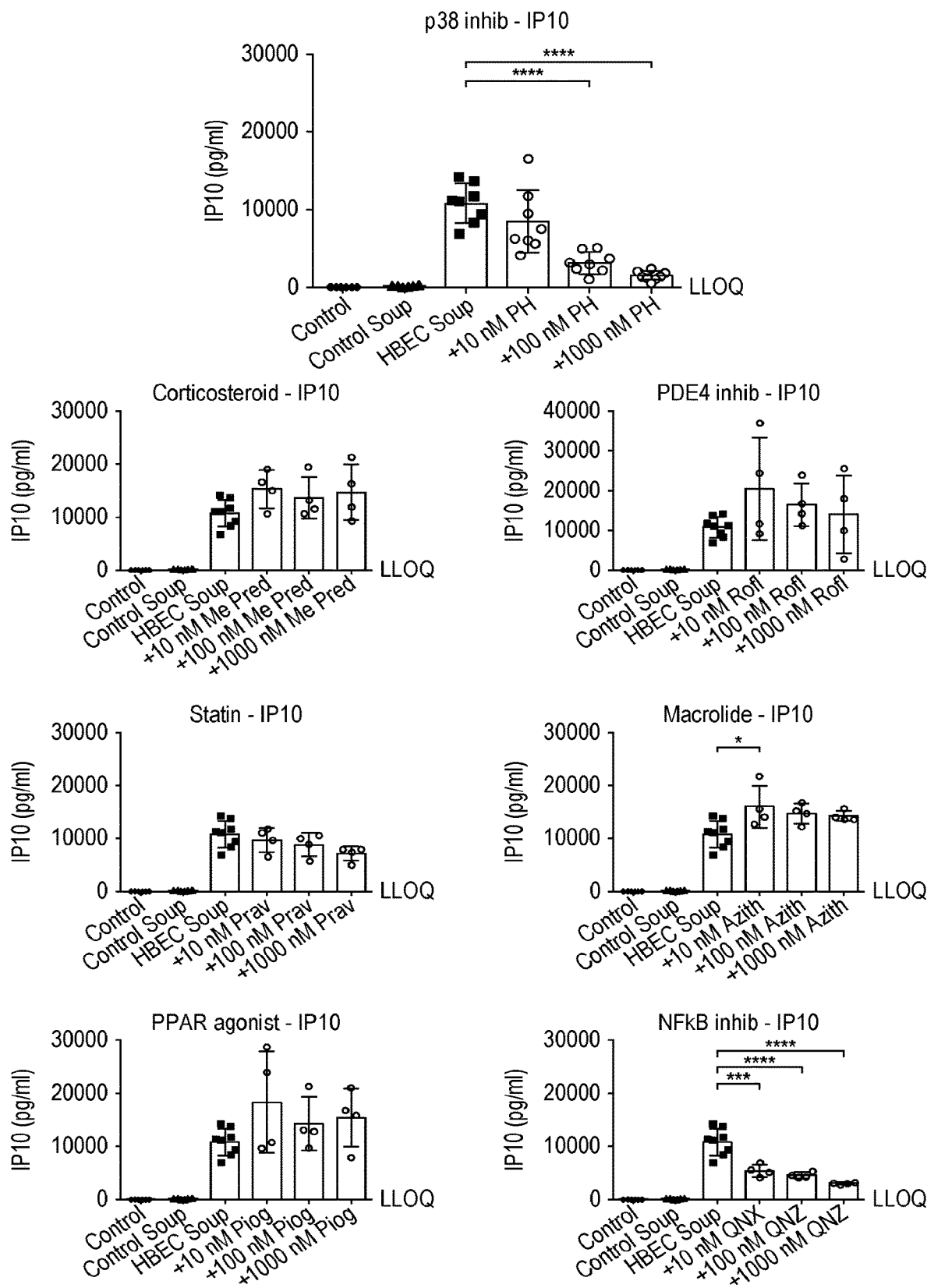
Figure 14:
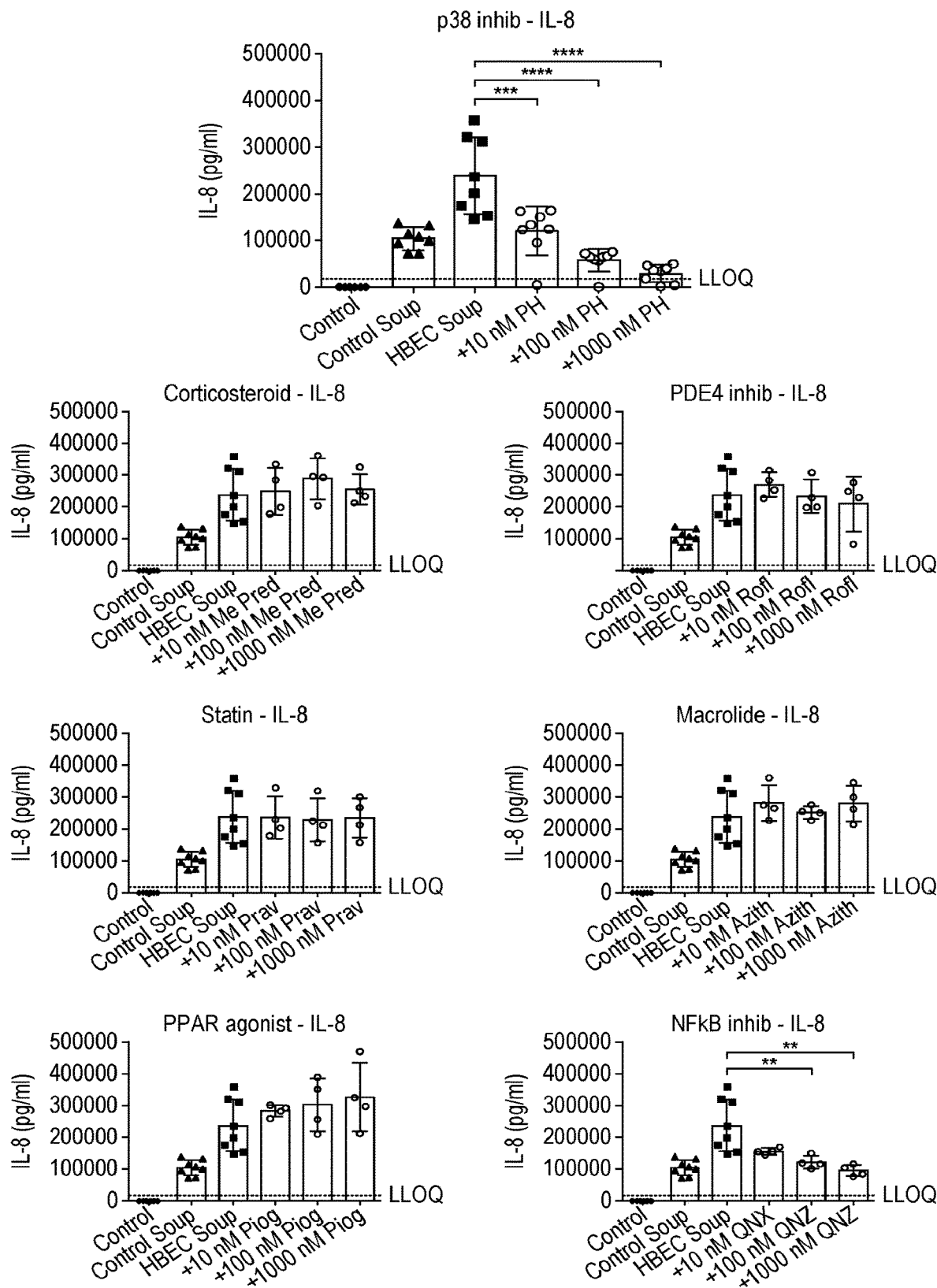

The inhibition plots for IP10 and IL8 are shown in FIGS. 13 and 14.

Based on the results obtained in the immune cell experiments, the superiority of p38i versus the other drugs was unexpected, especially methyl prednisolone, which is used routinely in clinical settings to treat a range of inflammatory diseases (e.g. asthma) and is commonly prescribed for severe influenza, although there is uncertainty over their potential benefit or harm (Rodrigo C et al., Corticosteroids as adjunctive therapy in the treatment of influenza, *Cochrane Database of Systematic Reviews*, 2016, Issue 3. Art. No.: CD010406. DOI:10.1002/14651858.CD010406.pub2]. NFκB is downstream of p38, so the inhibition profile seen is not unexpected.

Figure 15:
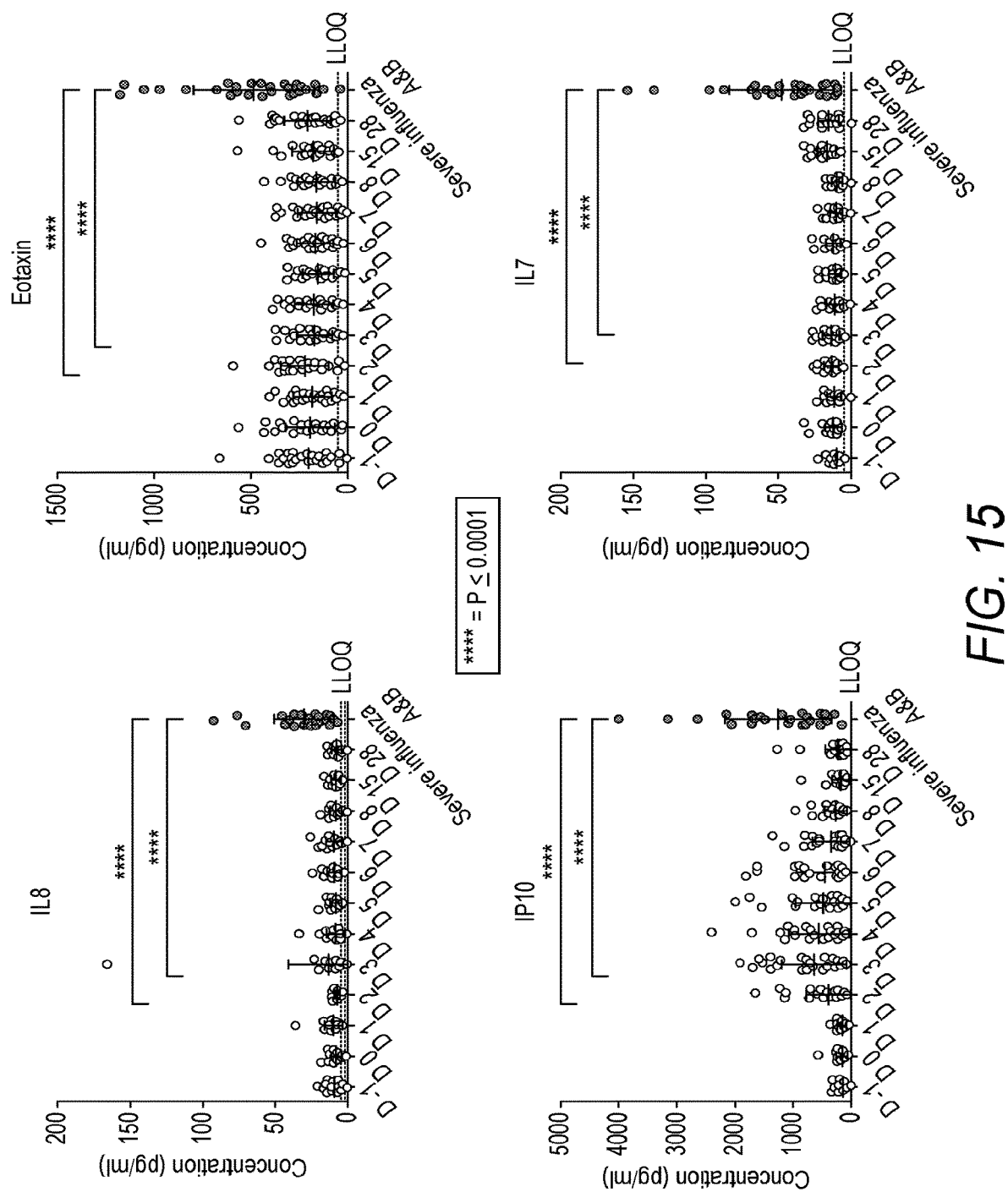

Example 5: Levels of a Number of Cytokines in Serum from Patients Hospitalised for Severe Influenza were Significantly Raised Relative to Influenza-Infected Individuals without Severe Influenza Cytokine levels in serum samples from 30 subjects hospitalised with severe influenza during the 2015 influenza season and from 28 healthy subjects infected after intranasal inoculation with influenza A/1-I3N2 Perth/16/2009 virus were assayed using electrogenerated chemiluminescence. In the case of the former, a serum sample prepared from a blood sample collected 24-72 hours after the subject was admitted to hospital was analysed. In the case of the latter, serum was analysed from blood samples collected at 12 pre-determined intervals (Day −1 to Day 28). Eight cytokines were observed to be significantly raised in the hospitalised versus the infected healthy subjects: IL-8, IL-7, IL-16, Eotaxin, IP10, MCP1, MCP4 and VEGF. The results for four of these are shown in FIG. 15.

The results show that the hospitalised subjects are distinguishable from the healthy infected subjects in terms of their serum cytokine profiles.

ABBREVIATIONS

ATP Adenosine triphosphate
Btk Bruton's tyrosine kinase
ERK Extracellular signal-regulated kinases)
GSK Glaxo Smith-Kline
HBEC Human bronchial epithelial cells
HSP27 Heat shock protein 27
HUVEC Human vascular endothelial cells
IC50 Half maximal inhibitory concentration
iMax Maximal inhibition (as a %)
IL1-b Interleukin 1 beta
IL-6 Interleukin 6
IL-8 Interleukin 8
IPA Ingenuity Pathways Analysis
JAK/STAT Janus kinase/signal transducer and activator of transcription JNK c-Jun N-terminal kinase
MCP-1 Monocyte chemotactic protein-1
MDCK Madin Darby canine kidney
MEK Mitogen-activated protein kinase kinase
MEKi MEK inhibition (by drug)
mTOR Mechanistic target of rapamycin
NFκB Nuclear factor kappa-light-chain-enhancer of activated B cells
P38 MAPK P38 Mitogen-activated protein kinases
P38i p38 inhibition (by drug)
PBMC Peripheral blood mononuclear cells
PDE4 Phosphodiesterase 4
PKC Protein kinase
PPAR Peroxisome proliferation-activated receptor
SRC Src kinase
TNFα Tumour necrosis factor alpha

The invention claimed is:

1. A method of treating a human patient at risk of severe influenza after an immune response has been triggered, said method comprising administering to the patient a p38 MAP kinase inhibitor, wherein the p38 MAP kinase inhibitor inhibits the release of pro-inflammatory mediators from endothelial cells and inhibits the release of pro-inflammatory cytokines from immune cells.

2. The method of claim 1, wherein the patient has exhibited one or more symptoms of influenza infection for more than two days and has at least one symptom selected from tachypnoea, hypoxemia, cardiopulmonary insufficiency and radiological pulmonary infiltrates.

3. The method of claim 1, wherein the patient has exhibited one or more symptoms of influenza infection for more than two days and requires hospitalization in view of the influenza infection.

4. The method of claim 1, wherein the patient has exhibited one or more symptoms of influenza infection for more than two days and has at least one symptom selected from tachypnoea, hypoxemia, cardiopulmonary insufficiency and radiological pulmonary infiltrates and requires hospitalization in view of the influenza infection.

5. The method of claim 1, wherein said severe influenza is characterised by hypercytokinemia.

6. The method of claim 5, wherein said hypercytokinemia involves elevated levels of at least one of the following cytokines: TNF α, IL-6, IL-8, and IP10.

7. The method of claim 1, wherein the p38 MAP kinase inhibitor is administered in an amount effective to inhibit the release of IP10 from endothelial cells.

8. The method of claim 1, wherein the p38 MAP kinase inhibitor exhibits dose-dependent inhibition of cytokines released from endothelial cells.

9. The method of claim 1, wherein said symptoms or signs of hypoxemia or cardiopulmonary insufficiency include at least one of dyspnoea, tachypnoea, cyanosis, low blood pressure, and hypoxia.

10. The method of claim 9, wherein tachypnoea designates respiratory rate >30 for ages ≥12 years, rate >40 for ages 6 to 12 years, rate ≥45 for ages 3 to 6 years, and rate >50 for ages 1 to 3 years.

11. The method of claim 1, wherein said severe influenza is characterised by at least one of comorbidity with a lower respiratory disorder without radiological pulmonary infiltrates, symptoms or signs suggesting CNS, symptoms or signs suggesting peripheral neuromuscular disorders, severe dehydration, fatigue, lethargy, evidence of sustained viral infection, invasive secondary bacterial infection, a lower respiratory tract disorder, inflammation, mono-organ failure, multi-organ failure, and septic shock.

12. The method of claim 1, wherein the patient is one of the following: an infant, an elderly person, and a pregnant woman.

13. The method of claim 1, wherein the patient is immunocompromised or has one or more underlying comorbidities.

14. The method of claim 13, wherein said one or more underlying comorbidities are selected from COPD, severe genetic anaemia, asthma, diabetes, chronic hepatic or renal insufficiency, obesity, and a cardiovascular disorder or condition.

15. The method of claim 1, which comprises administering the p38 MAP kinase inhibitor to the patient for a maximum period of 1-5 days.

16. The method of claim 1, which comprises administering the p38 MAP kinase inhibitor to the patient once a day.

17. The method of claim 1, wherein the p38 MAP kinase inhibitor is selected from 2-(4-Chlorophenyl)-4-(fluorophenyl)-5-pyridin-4-yl-1,2-dihydropyrazol-3-one; 4-[4-(4-Fluorophenyl)-1-(3-phenylpropyl)-5-(4-pyridinyl)-1H-imidazol-2-yl]-3-butyn-1-ol; (2R)-2-[[(2R)-2-amino-5-(diaminomethylideneamino)pentanoyl]amino]-N-[(2R)-1-[(2R)-1-[(2R)-1-[(2R)-1-[(2R)-1-[2-[(2R)-1-amino-3-(4-hydroxyphenyl)-1-oxopropan-2-yl]amino]-2-oxoethyl]amino]-1-oxohexan-2-yl]amino]-1-oxohexan-2-yl]amino]-1-oxohexan-2-yl]amino]-5-(diaminomethylideneamino)-1-oxopentan-2-yl]amino]-1-oxohexan-2-yl]amino]-1-oxohexan-2-yl]hexanamide; 2-[6-chloro-5-[(2R,5S)-4-[(4-fluorophenyl)methyl]-2,5-dimethylpiperazine-1-carbonyl]-1-methylindol-3-yl]-N,N-dimethyl-2-oxoacetamide; 6-[(6R)-2-(4-fluorophenyl)-6-(hydroxymethyl)-4,5,6,7-tetrahydropyrazolo[1,5-a]pyrimidin-3-yl]-2-(2-methylphenyl)pyridazin-3-one; 4-[3-[4-(4-fluorophenyl)-5-pyridin-4-ylimidazol-1-yl]propyl]morpholine, 4-[5-(4-fluorophenyl)-3-piperidin-4-ylimidazol-4-yl]pyrimidin-2-amine; 4-[5-(4-fluorophenyl)-3-piperidin-4-ylimidazol-4-yl]pyridine; 4-[4-(4-fluorophenyl)-2-(4-methylsulfinylphenyl)-1H-imidazol-5-yl]pyridine; 4-[4-(4-fluorophenyl)-5-(2-methoxypyrimidin-4-yl)imidazol-1-yl]cyclohexan-1-ol; 4-[5-(4-fluorophenyl)-3-piperidin-4-ylimidazol-4-yl]-2-methoxypyrimidine; 6-(N-carbamoyl-2,6-difluoroanilino)-2-(2,4-difluorophenyl)pyridine-3-carboxamide; 5-(2,6-dichlorophenyl)-2-(2,4-difluorophenyl)sulfanylpyrimido[1,6-b]pyridazin-6-one; 2-[[(2S)-2-amino-3-phenylpropyl]amino]-3-methyl-5-naphthalen-2-yl-6-pyridin-4-ylpyrimidin-4-one; 1-[5-tert-butyl-2-(4-methylphenyl)pyrazol-3-yl]-3-[4-(2-morpholin-4-ylethoxy)naphthalen-1-yl]urea; 6-(2,4-difluorophenoxy)-2-(1,5-dihydroxypentan-3-ylamino)-8-methylpyrido[2,3-d]pyrimidin-7-one; 1-[7-(4-fluorophenyl)-8-pyridin-4-yl-3,4-dihydro-1H-pyrazolo[5,1-c][1,2,4]triazin-2-yl]-2-phenylethane-1,2-dione; 8-(2,6-difluorophenyl)-2-(1,3-dihydroxypropan-2-ylamino)-4-(4-fluoro-2-methylphenyl)pyrido[2,3-d]pyrimidin-7-one; 2-[4-(4-fluorophenyl)-5-(2-phenoxypyrimidin-4-yl)imidazol-1-yl]propane-1,3-diol; N,N'-bis[3,5-bis[(E)-N-(diaminomethylideneamino)-C-methylcarbonimidoyl]phenyl]decanediamide; [2-[4-(4-fluorophenyl)-5-pyridin-4-yl-1H-imidazol-2-yl]-5-methyl-1,3-dioxan-5-yl]-morpholin-4-ylmethanone; methanesulfonic acid; [5-amino-1-(4-fluorophenyl)pyrazol-4-yl]-[3-[(2S)-2,3-dihydroxypropoxy]phenyl]methanone; 2-(2-chloro-6-fluorophenyl)-N-[3-(4-fluorophenyl)-4-pyrimidin-4-yl-1,2-oxazol-5-yl]acetamide; [(2R,3S,4R,5R,6R)-5-[[2-(aminomethylideneamino)acetyl]-methylamino]-3-hydroxy-2-(hydroxymethyl)-6-[(7-hydroxy-5-methyl-4-oxo-3a,6,7,7a-tetrahydro-1H-imidazo[4,5-c]pyridin-2-yl)amino]oxan-4-yl]carbamate; 1-[5-tert-butyl-2-(4- methylphenyl)pyrazol-3-yl]-3-[5-fluoro-2-[1-(2-hydroxyethyl)indazol-5-yl]oxyphenyl]methyl]urea; 5-(2,4-difluorophenoxy)-N-[2-(dimethylamino)ethyl]-1-(2-methylpropyl)indazole-6-carboxamide; N-cyclopropyl-3-fluoro-4-methyl-5-[3-[1-[2-[2-(methylamino)ethoxy]phenyl]cyclopropyl]amino]-2-oxopyrazin-1-yl]benzamide; 3-[5-amino-4-(3-cyanobenzoyl)pyrazol-1-yl]-N-cyclopropyl-4-methylbenzamide; 4-[5-(cyclopropylcarbamoyl)-2-methylanilino]-5-methyl-N-propylpyrrolo[2,1-f][1,2,4]triazine-6-carboxamide; 4-[4-(4-fluorophenyl)-2-(4-methylsulfonylphenyl)-1H-imidazol-5-yl]pyridine; N-[4-[5-(4-fluorophenyl)-3-methyl-2-methylsulfinylimidazol-4-yl]pyridin-2-yl]acetamide; 1-(5-tert-butyl-2-phenylpyrazol-3-yl)-3-[2-fluoro-4-[(3-oxo-4H-pyrido[2,3-b]pyrazin-8-yl)oxy]phenyl]urea, 1-(5-tert-butyl-2-phenylpyrazol-3-yl)-3-[2-methylsulfanyl-4-[(3-oxo-4H-pyrido[2,3-b]pyrazin-8-yl)oxy]phenyl]urea; 4-(3,4-Dichlorophenyl)-5-(4-pyridinyl)-2-thiazolamine dihydrochloride; 5-(2-chloroethyl)-4-methyl-1,3-thiazole; ethane-1,2-disulfonic acid; 2'-Fluoro-N-(4-hydroxyphenyl)-[1,1'-biphenyl]-4-butanamide; [4-(2-amino-4-bromoanilino)-2-chlorophenyl]-(2-methylphenyl)methanone; (E)-3-[4-(imidazol-1-ylmethyl)phenyl]prop-2-enoic acid; 17alpha-ethynyl-5-androstene-3beta, 7beta, 17beta-triol; (Z)-6-amino-2-(3',5'-dibromo-4'-hydroxybenzylidene)-2H-benzo[b][1,4]oxazin-3 (4H)-one; (4-benzylpiperidin-1-yl)-(2-methoxy-4-methylsulfanylphenyl)methanone; 6-[5-(cyclopropylcarbamoyl)-3-fluoro-2-methylphenyl]-N-(2,2-dimethylpropyl)pyridine-3-carboxamide; 5-[2-tert-butyl-4-(4-fluorophenyl)-1H-imidazol-5-yl]-3-(2,2-dimethylpropyl)imidazo[4,5-b]pyridin-2-amine; methanesulfonic acid; 4-[5-(4-fluorophenyl)-2-methylsulfanyl-1H-imidazol-4-yl]-N-(1-phenylethyl)pyridin-2-amine; 2-(3,4-dihydroxyphenyl)-3-hydroxychromen-4-one; 1-[5-tert-butyl-2-(3-chloro-4-hydroxyphenyl)pyrazol-3-yl]-3-[2-[3-[2-(2-hydroxyethylsulfanyl)phenyl]-[1,2,4]triazolo[4,3-a]pyridin-6-yl]sulfanyl]phenyl]methyl]urea; 3-[3-bromo-4-[(2,4-difluorophenyl)methoxy]-6-methyl-2-oxopyridin-1-yl]-N,4-dimethylbenzamide; 5-[2-tert-butyl-4-(4-fluorophenyl)-1H-imidazol-5-yl]-3-(2,2-dimethylpropyl)imidazo[4,5-b]pyridin-2-amine; 4-[4-[4-chloro-3-(trifluoromethyl)phenyl]carbamoylamino]-3-fluorophenoxy]-N-methylpyridine-2-carboxamide; [5-amino-1-(4-fluorophenyl)pyrazol-4-yl]-[3-[(2S)-2,3-dihydroxypropoxy phenyl]methanone, 4-[4-(4-fluorophenyl)-5-pyridin-4-yl-1H-imidazol-2-yl]phenol; 4-[4-(4-fluorophenyl)-2-(4-methylsulfinylphenyl)-1H-imidazol-5-yl]pyridine hydrochloride; 4-[4-(4-fluorophenyl)-5-pyridin-4-yl-1H-imidazol-2-yl]phenol hydrochloride; 1-[4-[3-(4-chlorophenyl)-4-pyrimidin-4-yl-1H-pyrazol-5-yl]piperidin-1-yl]-2-hydroxyethanone; N,N'-bis[3,5-bis[(E)-N-(diaminomethylideneamino)-C-methylcarbonimidoyl]phenyl]decanediamide, 6-(4-fluorophenyl)-5-pyridin-4-yl-2,3-dihydroimidaz[2,1-b][1,3]thiazole; 2-[6-chloro-5-[4-[(4-fluorophenyl)methyl]piperidine-1-carbonyl]-1-methylindol-3-yl]-N,N-dimethyl-2-oxoacetamide; [5-amino-1-(4-fluorophenyl)pyrazol-4-yl]-[3-(2,3-dihydroxypropoxy)phenyl]methanone; N-[4-[2-ethyl-4-(3-methylphenyl)-1,3-thiazol-5-yl]pyridin-2-yl]benzamide; 4-[4-(6-methoxynaphthalen-2-yl)-2-(4-methylsulfinylphenyl)-1H-imidazol-5-yl]pyridine; 4,6-bis(p-fluorophenyl)-2-methyl-5-(4-pyridyl)-1,2,7-triaza-2H-indene; and 2-(3-phenyl-4,5-dihydro-1,2-oxazol-5-yl)acetic acid.

18. The method of claim 1, wherein the p38 MAP kinase inhibitor is selected from 8-(2,6-difluorophenyl)-2-(1,3-dihydroxypropan-2-ylamino)-4-(4-fluoro-2-methylphenyl)pyrido[2,3-d]pyrimidin-7-one, (E)-3-[4-(imidazol-1-ylmethyl)phenyl]prop-2-enoic acid; 6-[5-(cyclopropylcarbamoyl)-3-fluoro-2-methylphenyl]-N-(2,2-dimethylpropyl)pyridine-3-carboxamide, 5-[(2-chloro-6-fluorophenyl)acetylamino]-3-(4-fluorophenyl)-4-(4-pyrimidinyl)isoxazole, 1-[5-tert-butyl-2-(3-chloro-4-hydroxyphenyl)pyrazol-3-yl]-3-[2-[3-[2-(2-hydroxyethylsulfanyl)phenyl]-[1,2,4]triazolo[4,3-a]pyridin-6-yl]sulfanyl]phenyl]methyl]urea, 3-[3-bromo-4-[(2,4-difluorophenyl)methoxy]-6-methyl-2-oxopyridin-1-yl]-N,4-dimethylbenzamide, 2-methoxy-1-{4-[(4-{3-[5-(tert-butyl)-2-(p-tolyl)-2H-pyrazol-3-yl]ureido}-1-naphthyloxy)methyl]-2-pyridylamino}-1-ethanone, 2-methoxy-1-[4-(4-{3-[5-(tert-butyl)-2-(p-tolyl)-2H-pyrazol-3-yl]ureido}-1-naphthyloxy)-2-pyridylamino]-1-ethanone, and 4,6-bis(p-fluorophenyl)-2-methyl-5-(4-pyridyl)-1,2,7-triaza-2H-indene.

19. A method of treating hypercytokinemia characteristic of severe influenza, the method comprising administering to the patient a therapeutically effective amount of a p38 MAP kinase inhibitor; wherein the p38 MAP kinase inhibitor inhibits the release of pro-inflammatory mediators from endothelial cells and inhibits the release of pro-inflammatory cytokines from immune cells.

* * * * *